United States Patent [19]

Yanagisawa et al.

[11] Patent Number: 5,459,148
[45] Date of Patent: Oct. 17, 1995

[54] BIPHENYL DERIVATIVES AND THEIR USE FOR THE TREATMENT OF HYPERTENSION AND CARDIAC DISEASE

[75] Inventors: Hiroaki Yanagisawa; Yoshiya Amemiya; Takuro Kanazaki; Yasuo Shimoji; Hiroyuki Koike; Toshio Sada, all of Tokyo, Japan

[73] Assignee: Sankyo Company, Limited, Tokyo, Japan

[21] Appl. No.: 331,356

[22] Filed: Oct. 27, 1994

Related U.S. Application Data

[63] Continuation of Ser. No. 170,046, Dec. 17, 1993, abandoned.

[30] Foreign Application Priority Data

Dec. 17, 1992 [JP] Japan ................................. 5-337675

[51] Int. Cl.⁶ .................... A61K 31/415; A61K 31/435; C07D 233/90; C07D 471/04
[52] U.S. Cl. ..................... 514/303; 514/340; 514/352; 514/381; 514/394; 514/396; 514/397; 514/399; 546/276; 546/289; 546/297; 546/307; 546/310; 546/312; 546/118; 544/329; 548/253; 548/304.7; 548/306.4; 548/307.1; 548/310.1; 548/319.1; 548/333.5; 548/334.5; 548/341.5
[58] Field of Search ................... 546/276, 289, 546/297, 307, 310, 312, 118; 548/253, 304.7, 306.4, 307.1, 310.1, 319.1, 333.5, 334.5, 341.5; 544/329; 514/303, 340, 352, 381, 394, 396, 397, 399

[56] References Cited

U.S. PATENT DOCUMENTS 4,226,878  12/1980  Iizuka et al. ............................. 424/273
4,335,040  10/1982  Furukawa et al. ....................... 424/273

(List continued on next page.)

FOREIGN PATENT DOCUMENTS 7820091  12/1991  Australia .
8016391  1/1992   Australia .

(List continued on next page.)

OTHER PUBLICATIONS

Wong et al, "Nonpeptide Angiotensin II Receptor Antagonists, XI, Pharmacology of EXP 3174: An Active Metabolite of DuP 753, An Orally Active Antihypertensive Agent", (1990), 211–217, 255, *The Journal of Pharmacology and Experimental Therapeutics.*
*Merck Index,* 11th Edition, p. 855, No. 5319, Lenampicillin (1989).
*Chem. Abs.* 109:73432w of U.S. Pat. No. 4,812,462 (1988).
*Chem. Abs.* 114:164233b of EP 399732 (1991).
*Chem. Abs.* 114:228914j of EP 400835 (1991).
D. J. Carini et al, "Nonpeptide Angiotensin II Receptor Antagonists: The Discovery of a Series of N–(Biphenylmethyl)imidazoles as Potent, Orally Active Antihypertensives", *J. Med. Chem.*, vol. 34, No. 8, 1991, pp. 2525–2547.

*Primary Examiner*—Bernard Dentz
*Attorney, Agent, or Firm*—Frishauf, Holtz, Goodman, Langer & Chick

[57] ABSTRACT

Compounds of formula (I):

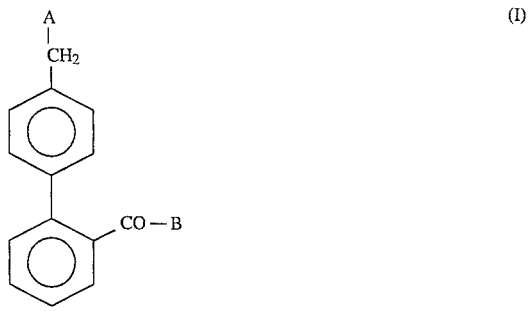

[wherein: A represents a group (IIa), (IIb) or (IIc):

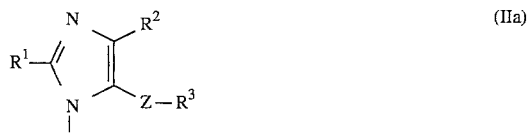

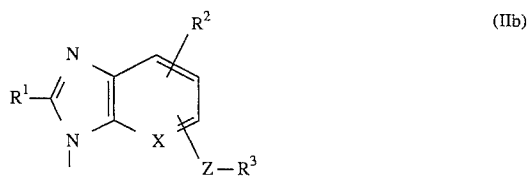

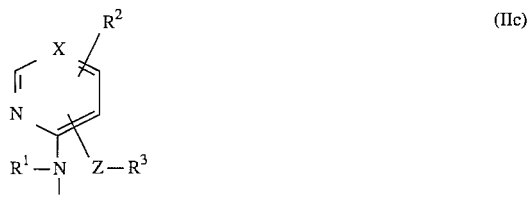

$R^1$ is alkyl, alkenyl, cycloalkyl or a group of formula $R^4$—Y—$R^5$—, where: $R^4$ is hydrogen, alkyl, or cycloalkyl, $R^5$ is a single bond or alkylene, and Y is oxygen, sulfur or imino group; $R^2$ is hydrogen, halogen, optionally substituted alkyl, optionally substituted alkenyl, optionally substituted cycloalkyl, hydroxy, amino, alkylamino, dialkylamino, formyl, alkylcarbonyl, alkoxy, alkylthio, cyano or nitro; $R^3$ is hydrogen, alkyl, carboxy, protected carboxy, carbamoyl or tetrazol-5-yl; X is of formula —CH=, —N= or —C(COOR⁶)=, where $R^6$ is hydrogen or a carboxy-protecting group; Z is a single bond, alkylene or vinylene; and B is carboxy, protected carboxy or tetrazol-5-yl]; and pharmaceutically acceptable salts and esters thereof have the ability to inhibit the action of angiotensin II and thus can be used for the treatment and prophylaxis of hypertension and cardiac diseases.

99 Claims, No Drawings

U.S. PATENT DOCUMENTS

| | | | |
|---|---|---|---|
| 4,340,598 | 7/1982 | Furukawa et al. | 548/342 |
| 4,342,693 | 8/1982 | Sakamoto et al. | 549/229 |
| 4,555,516 | 11/1985 | Cross et al. | 514/326 |
| 4,812,462 | 3/1989 | Blankley et al. | 514/303 |
| 4,816,463 | 3/1989 | Blankley et al. | 514/293 |
| 4,820,843 | 4/1989 | Aldrich et al. | 546/2 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |
| 4,916,129 | 4/1990 | Carini et al. | 514/235.2 |
| 5,015,651 | 5/1991 | Carini et al. | 514/381 |
| 5,039,814 | 8/1991 | Shuman et al. | 548/250 |
| 5,043,349 | 8/1991 | Carini et al. | 514/427 |
| 5,064,825 | 11/1991 | Chakravarty et al. | 514/221 |
| 5,081,127 | 1/1992 | Carini et al. | 514/359 |
| 5,089,626 | 2/1992 | King | 548/253 |
| 5,093,346 | 3/1992 | Carini et al. | 514/381 |
| 5,126,342 | 6/1992 | Chakravarty et al. | 514/235.8 |
| 5,128,355 | 7/1992 | Carini et al. | 514/381 |
| 5,137,902 | 8/1992 | Carini et al. | 514/381 |
| 5,138,069 | 8/1992 | Carini et al. | 548/253 |
| 5,140,037 | 8/1992 | Chiu et al. | 514/381 |
| 5,153,197 | 10/1992 | Carini et al. | 514/255 |
| 5,155,118 | 10/1992 | Carini et al. | 514/381 |
| 5,171,748 | 12/1992 | Roberts et al. | 514/381 |
| 5,177,097 | 1/1993 | Poss | 514/386 |
| 5,189,048 | 2/1993 | Carini et al. | 514/359 |
| 5,210,079 | 5/1993 | Carini et al. | 514/94 |
| 5,219,856 | 6/1993 | Olson | 514/252 |
| 5,225,414 | 7/1993 | Henning et al. | 514/258 |
| 5,236,928 | 8/1993 | Chakravarty | 514/275 |
| 5,236,943 | 8/1993 | Heitsch et al. | 514/397 |
| 5,252,753 | 11/1993 | Russell et al. | 548/252 |
| 5,254,546 | 10/1993 | Ardecky et al. | 514/225.8 |
| 5,260,322 | 11/1993 | Nakasima et al. | 514/341 |
| 5,266,583 | 11/1993 | Ohtawa | 514/381 |
| 5,294,716 | 3/1994 | Thomas et al. | 546/135 |
| 5,310,928 | 5/1994 | Lo et al. | 548/252 |
| 5,310,929 | 5/1994 | Ardecky et al. | 548/253 |
| 5,312,828 | 5/1994 | Finkelstein et al. | 514/381 |
| 5,354,867 | 10/1994 | Carini et al. | 548/252 |

FOREIGN PATENT DOCUMENTS

| | | |
|---|---|---|
| 28833 | 5/1981 | European Pat. Off. |
| 28834 | 5/1981 | European Pat. Off. |
| 0245637 | 11/1987 | European Pat. Off. |
| 0253310 | 1/1988 | European Pat. Off. |
| 0323841 | 7/1989 | European Pat. Off. |
| 324377 | 7/1989 | European Pat. Off. |
| 437103 | 12/1989 | European Pat. Off. |
| 392317 | 4/1990 | European Pat. Off. |
| 400974 | 5/1990 | European Pat. Off. |
| 380959 | 8/1990 | European Pat. Off. |
| 0392317 | 10/1990 | European Pat. Off. |
| 399731 | 11/1990 | European Pat. Off. |
| 485929 | 11/1990 | European Pat. Off. |
| 399732 | 11/1990 | European Pat. Off. |
| 401030 | 12/1990 | European Pat. Off. |
| 400835 | 12/1990 | European Pat. Off. |
| 0400974 | 12/1990 | European Pat. Off. |
| 475206 | 8/1991 | European Pat. Off. |
| 0461039 | 12/1991 | European Pat. Off. |
| 468372 | 1/1992 | European Pat. Off. |
| 465368 | 1/1992 | European Pat. Off. |
| 470794 | 2/1992 | European Pat. Off. |
| 480659 | 4/1992 | European Pat. Off. |
| 492105 | 7/1992 | European Pat. Off. |
| 0503785 | 9/1992 | European Pat. Off. |
| 505098 | 9/1992 | European Pat. Off. |
| 503162 | 9/1992 | European Pat. Off. |
| 550313 | 7/1993 | European Pat. Off. |
| 573218 | 12/1993 | European Pat. Off. |
| 578125 | 1/1994 | European Pat. Off. |
| 4036706A1 | 5/1992 | Germany |
| 57-98270 | 6/1982 | Japan |
| 3-58942 | 3/1991 | Japan |
| 6-87833 | 3/1994 | Japan |
| 6-73029 | 3/1994 | Japan |
| WO91/00277 | 1/1991 | WIPO |
| WO91/00281 | 1/1991 | WIPO |
| WO91/14367 | 10/1991 | WIPO |
| WO91/19715 | 12/1991 | WIPO |
| WO93/04059 | 3/1993 | WIPO |
| WO94/09778 | 5/1994 | WIPO |

BIPHENYL DERIVATIVES AND THEIR USE FOR THE TREATMENT OF HYPERTENSION AND CARDIAC DISEASE

This application is a continuation of application Ser. No. 08/170,046, filed Dec. 17, 1993, now abandoned.

BACKGROUND TO THE INVENTION

The present invention relates to a series of new biphenyl derivatives which have the ability to inhibit the action of angiotensin II (hereinafter abbreviated as AII) and which thus can be used for the treatment and prophylaxis of hypertension and cardiac diseases. The invention also provides methods and compositions using these new compounds as well as processes for their preparation.

It is known that the renin-angiotensin system provides one of the important mechanisms for maintaining the homeostasis of blood pressure in living animals. When blood pressure is reduced or the sodium ion concentration of the body fluids falls, this system is activated. As a result, the enzyme renin and angiotensin converting enzyme (hereinafter abbreviated, as is conventional, as "ACE") are activated and act on angiotensinogen, which is first decomposed by the renin to produce angiotensin I (hereinafter abbreviated as "AI"). This AI is then converted by ACE to AII. Since AII induces strong contractions of blood vessels and accelerates the secretion of aldosterone (a hormone which facilitates the storage of body fluids and sodium ions), the activation of the system results in an elevation of blood pressure. Inhibitors or suppressors of the renin-angiotension system, such as renin inhibitors, ACE inhibitors and AII antagonists, dilate blood vessels, cause reduced blood pressure and improve the circulatory function, which is the basis for the use of these agents in the treatment of heart diseases.

At present only ACE inhibitors are used clinically, although renin inhibitors and AII antagonists are under extensive investigation for such use. Of these, some peptide type AII antagonists, such as Saralasin, have been known for many years, whilst certain non-peptide type antagonists have recently been discovered (for example, as disclosed in European Patent Publications No. 28 833, 28 834, 245 637, 253 310 and 323 841 and in Japanese Patent Application Kokai No. Sho 57-98270 and Hei 3-63264). Most of the AII antagonists which have been found to have a comparatively strong activity have a (2'-carboxybiphenyl-4-yl)methyl group or a [2'-(tetrazol-5-yl)biphenyl-4-yl)methyl group in their molecule, for example, as disclosed in European Patent Publications No. 253 310 and 324 377, and in Japanese Patent Applications Kokai No. Hei 3-58942, Hei 3-63264 and Hei 3-95181.

The closest prior art, however, is believed to be European Patent Publication No. 545 912, assigned to the present assignees, which describes a series of 1-biphenylmethylimidazole derivatives having excellent AII antagonist activity, but which differ from the compounds of the present invention in several respects, principally in the nature of the substituents on the benzene ring of the biphenyl moiety which is not attached to the methylimidazole group.

However, the activities of these prior art compounds are still insufficient, and thus an AII antagonist having a stronger activity is desired for therapeutic use.

We have now discovered a limited series of biphenylmethyl derivatives having an excellent AII receptor antagonist activity, and which are therefore useful as anti-hypertensive drugs and for the therapy and prophylaxis of heart diseases.

BRIEF SUMMARY OF INVENTION

It is, therefore, an object of the present invention to provide a series of new biphenylmethyl derivatives.

It is a further object of the invention to provide such compounds having AII inhibitory activity.

Other objects and advantages of the present invention will become apparent as the description proceeds.

Thus, the present invention provides compounds of formula (I):

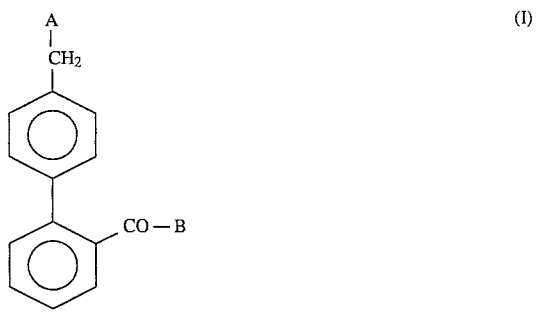

wherein:

A represents a group (IIa), (IIb) or (IIc):

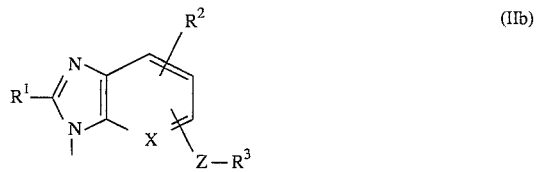

$R^1$ represents an alkyl group having from 1 to 6 carbon atoms, an alkenyl group having from 2 to 6 carbon atoms, a cycloalkyl group having from 3 to 8 ring carbon atoms or a group of formula $R^4—Y—R^5—$, where:

$R^4$ represents a hydrogen atom, an alkyl group having from 1 to 6 carbon atoms, or a cycloalkyl group having from 3 to 8 ring carbon atoms, $R^5$ represents a single bond or an alkylene group having from 1 to 4 carbon atoms, and Y represents an oxygen atom, a sulfur atom or an imino group (>NH);

$R^2$ represents a hydrogen atom, a halogen atom, an unsubstituted alkyl group having from 1 to 6 carbon atoms, an unsubstituted alkenyl group having from 2 to 6 carbon atoms, an unsubstituted cycloalkyl group having from 3 to 8 carbon atoms, a hydroxy group, an amino group, an alkylamino group having from 1 to 6 carbon atoms, a dialkylamino group in which each alkyl part has from 1 to 6 carbon atoms, a formyl group, an alkylcarbonyl group having from 2 to 7 carbon atoms, an alkoxy group having from 1 to 6 carbon atoms, an alkylthio group having from 1 to 6 carbon atoms, a cyano group, a nitro group, a substituted alkyl group which has from 1 to 6 carbon atoms and which is substituted by at least one substituent selected from the group consisting of substituents α defined below, a substituted alkenyl group which has from 2 to 6 carbon atoms and which is substituted by at least one substituent selected from the group consisting of substituents α defined below, or a substituted cycloalkyl group which has from 3 to 8 carbon atoms and which is substituted by at least one substituent selected from the group consisting of substituents α defined below;

$R^3$ represents a hydrogen atom, an alkyl group having from 1 to 6 carbon atoms, a carboxy group, a protected carboxy group, a carbamoyl group or a tetrazol-5-yl group;

X represents a group of formula —CH=, —N= or —C(COOR$^6$)=, where $R^6$ represents a hydrogen atom or a carboxy-protecting group;

Z represents a single bond, an alkylene group having from 1 to 4 carbon atoms or a vinylene group; and B represents a carboxy group, a protected carboxy group or a tetrazol-5-yl group;

said substituents α are selected from the group consisting of halogen atoms, hydroxy groups, amino groups, alkylamino groups having from 1 to 6 carbon atoms, dialkylamino groups in which each alkyl part has from 1 to 6 carbon atoms, formyl groups, alkylcarbonyl groups having from 2 to 7 carbon atoms, alkoxy groups having from i to 6 carbon atoms, alkylthio groups having from 1 to 6 carbon atoms, cyano groups and nitro groups;

and pharmaceutically acceptable salts and esters thereof.

The invention also provides a pharmaceutical composition for the treatment or prophylaxis of hypertension or of a cardiovascular disease, which comprises an effective amount of an anti-hypertensive agent in admixture with a pharmaceutically acceptable carrier or diluent, wherein the anti-hypertensive agent is selected from the group consisting of compounds of formula (I) and pharmaceutically acceptable salts and esters thereof.

The invention further provides a method for the treatment or prophylaxis of hypertension or of a cardiovascular disease in a mammal, e.g. a human being, which comprises administering an effective amount of an anti-hypertensive agent to said mammal, wherein the anti-hypertensive agent is selected from the group consisting of compounds of formula (I) and pharmaceutically acceptable salts and esters thereof.

The invention still further provides processes for the preparation of compounds of formula (I) and pharmaceutically acceptable salts and esters thereof, which are described in more detail hereafter.

DETAILED DESCRIPTION OF INVENTION

Where $R^1$, $R^2$, $R^3$ or $R^4$ represents an alkyl group, this may be a straight or branched chain group having from 1 to 6 carbon atoms, and examples include the methyl, ethyl, propyl, isopropyl, butyl, sec-butyl, t-butyl, isobutyl, pentyl, 2-methylbutyl, 3-methylbutyl, 2,2-dimethylpropyl, hexyl, 2-methylpentyl, 3-methylpentyl, 4-methylpentyl, 3,3-dimethylbutyl and 2-ethylbutyl groups. Preferably: $R^1$ represents an alkyl group having from 2 to 5 carbon atoms, particularly an ethyl, propyl or butyl group; and $R^2$ $R^3$ each represents a methyl, ethyl, isopropyl, t-butyl, isobutyl or 3,3-dimethylbutyl group; and $R^4$ represents an alkyl group having from 1 to 4 carbon atoms, particularly a methyl or ethyl group.

Where $R^2$ or substituent α represents an alkylamino group, a dialkylamino group, an alkylcarbonyl group, an alkoxy group, an alkylthio group or a substituted alkyl group, the or each alkyl part may be any one of those alkyl groups having from 1 to 6 carbon atoms exemplified above in relation to $R^1$ and is preferably such a group having from 1 to 4 carbon atoms. The methyl and ethyl groups are particularly preferred.

Specific examples of such mono- and di- alkylamino groups include the methylamino, ethylamino, propylamino, isopropylamino, butylamino, isobutylamino, sec-butylamino, t-butylamino, pentylamino, hexylamino, dimethylamino, diethylamino, dipropylamino, diisopropylamino, dibutylamino, diisobutylamino, di-t-butylamino, N-ethyl-N-methylamino, N-methyl-N-propylamino, N-ethyl-N-propylamino, N-methyl-N-isopropylamino, N-methyl-N-butylamino and N-methyl-N-t-butylamino groups.

Specific examples of such alkylcarbonyl groups having from 2 to 7 carbon atoms include the acetyl, propionyl, butyryl, isobutyryl, valeryl, isovaleryl, pivaloyl, hexanoyl and heptanoyl groups, of which the acetyl and propionyl groups are preferred.

Specific examples of such alkoxy groups having from 1 to 6 carbon atoms include the methoxy, ethoxy, propoxy, isopropoxy, butoxy, sec-butoxy, t-butoxy, isobutoxy, pentyloxy, 2-methylbutoxy, 3-methylbutoxy, 2,2-dimethylpropoxy, hexyloxy, 2-methylpentyloxy, 3-methylpentyloxy, 4-methylpentyloxy, 3,3-dimethylbutoxy and 2-ethylbutoxy groups, of which the methoxy and ethoxy groups are preferred.

Specific examples of such alkylthio groups having from 1 to 6 carbon atoms include the methylthio, ethylthio, propylthio, isopropylthio, butylthio, sec-butylthio, t-butylthio, isobutylthio, pentylthio, 2-methylbutylthio, 3-methylbutylthio, 2,2-dimethylpropylthio, hexylthio, 2-methylpentylthio, 3-methylpentylthio, 4-methylpentylthio, 3,3-dimethylbutylthio and 2-ethylbutylthio groups, of which the methylthio and ethylthio groups are preferred.

Where $R^2$ represents a substituted alkyl group, the alkyl group itself has from 1 to 6 carbon atoms and is substituted by at least one substituent selected from the group consisting of substituents α, defined above. There is no particular limitation on the number of such substituents, except such as may be imposed by the number of substitutable carbon atoms and possibly by steric constraints; the preferred number of substituents depends on the nature of the substituent. Thus, where the substituent is a halogen atom, the preferred number is from 1 to 5 (from 1 to 3, in the case of substituted methyl groups), more preferably from 2 to 5 (2 or 3, in the case of substituted methyl groups). In the case of the other substituents, a single substituent is preferred. Where there are two or more substituents, these may be the same or different. Examples of such substituents include: halogen atoms, such as the fluorine, chlorine, bromine and iodine atoms, of which the fluorine and chlorine atoms are preferred, the fluorine atom being most preferred; the hydroxy group; amino groups; alkylamino and dialkylamino groups, such as those exemplified above in relation to $R^2$; the formyl group; alkylcarbonyl, alkoxy and alkylthio groups, such as those exemplified above in relation to $R^2$;

the cyano group; and the nitro group. Examples of such substituted alkyl groups include the trifluoromethyl, pentafluoroethyl, heptafluoropropyl, hydroxymethyl, 1-hydroxyethyl, 2-hydroxyethyl, 1-hydroxy-1-methylethyl, 1-hydroxypropyl, 1-hydroxy-1-methylpropyl, 1-hydroxy-2-methylpropyl, 1-ethyl-1-hydroxypropyl, 1-hydroxy-2,2-dimethylpropyl, 2-ethyl-1-hydroxybutyl, 2-ethyl-1-hydroxypentyl, aminomethyl, 1-aminoethyl, 2-aminoethyl, 1-amino-1-methylethyl, 1-aminopropyl, 1-amino-1-methylpropyl, 1-amino-2-methylpropyl, 1-amino-1-ethylpropyl, N-methylaminomethyl, N-ethylaminomethyl, N,N-dimethylaminomethyl, N,N-diethylaminomethyl, formylmethyl, formylethyl, acetylmethyl, acetylethyl, propionylmethyl, butyrylmethyl, isobutyrylmethyl, methoxymethyl, 1-methoxyethyl, 2-methoxyethyl, 1-methoxy-1-methylethyl, 1-methoxypropyl, 1-methoxy-1-methylpropyl, 1-methoxy-2-methylpropyl, 1-ethyl-1-methoxypropyl, 1-methoxy-2,2-dimethylpropyl, 2-ethyl-1-methoxybutyl, methylthiomethyl, ethylthiomethyl, 1-methylthioethyl, 2-methylthioethyl, cyanomethyl, 1-cyanoethyl, 2-cyanoethyl, nitromethyl, 1-nitroethyl and 2-nitroethyl groups, of which we prefer the trifluoromethyl, pentafluoroethyl, hydroxymethyl, 1-hydroxyethyl, 1-hydroxy-1-methylethyl, 1-hydroxypropyl, 1-hydroxy-2-methylpropyl, 1-hydroxy-2,2-dimethylpropyl, aminomethyl, N-methylaminomethyl, N,N-dimethylaminomethyl, N,N-diethylaminomethyl, acetylmethyl, propionylmethyl, methoxymethyl and 1-methoxy-1-methylethyl groups.

Where $R^1$ or $R^2$ represents an unsubstituted alkenyl group or $R^2$ represents a substituted alkenyl group, this may be any alkenyl group having from 2 to 6 carbon atoms and my be a straight or branched chain group. Examples of such groups include the vinyl, allyl, 1-propenyl, isopropenyl, 1-butenyl, 2-butenyl, 2-methyl-1-propenyl, 1-pentenyl, 2-pentenyl, 3-methyl-2-butenyl and 1-hexenyl groups, of which those groups having from 2 to 4 carbon atoms are preferred and those having 3 or 4 carbon atoms are more preferred. In the case of $R^1$, we prefer alkenyl groups having 3 or 4 carbon atoms, particularly the 1-propenyl and 1-butenyl groups. In the case of $R^2$ we prefer alkenyl groups having 3 or 4 carbon atoms, particularly the isopropenyl and 2-methyl-1-propenyl groups.

Where $R^2$ represents a substituted alkenyl group, the substituent or substituents may be selected from the group consisting of substituents α, defined and exemplified above. As before, there is no particular limitation on the number of such substituents, except such as may be imposed by the number of substitutable carbon atoms and possibly by steric constraints, and the preferred number of substituents depends on the nature of the substituent. In this case, where the substituent is a halogen atom, the preferred number is from 1 to 3. In the case of the other substituents, a single substituent is preferred. Where there are two or more substituents, these may be the same or different. Examples of such substituted groups include the 2,2-difluorovinyl, 2,2-dichlorovinyl, 3-hydroxy-1-propenyl, 3-hydroxy-2-methyl-1-propenyl, 3-amino-1-propenyl, 3-amino-2-methyl-1-propenyl, 3-methylamino-1-propenyl, 3-methylamino-2-methyl-1-propenyl, 3-(N,N-dimethylamino)-1-propenyl, 3-(N,N-dimethylamino)-2-methyl-1-propenyl, 3-formyl-1-propenyl, 3-formyl-2-methyl-1-propenyl, 2-acetylvinyl, 2-propionylvinyl, 3-methoxy-1-propenyl, 3-methoxy-2-methyl-1-propenyl, 3-methylthio-1-propenyl, 3-methylthio-2-methyl-1-propenyl, 3-cyano-1-propenyl, 3-cyano-2-methyl-1-propenyl, 3-nitro-1-propenyl and 2-methyl-3-nitro-1-propenyl groups, of which we prefer the 2,2-difluorovinyl, 2,2-dichlorovinyl, 3-hydroxy-1-propenyl, 3-hydroxy-2-methyl-1-propenyl, 3-methoxy-1-propenyl and 3-methoxy-2-methyl-1-propenyl groups.

Where $R^1$, $R^2$ or $R^4$ represents a cycloalkyl group or $R^2$ represents a substituted cycloalkyl group, this may have from 3 to 8, preferably from 3 to 6, carbon atoms, and examples include the cyclopropyl, cyclobutyl, cyclopentyl, cyclohexyl, cycloheptyl and cyclooctyl groups, of which the cyclopropyl, cyclobutyl, cyclopentyl and cyclohexyl groups are preferred. In the case of $R^1$ and $R^4$, the cyclopropyl groups are preferred. In the case of $R^2$, the cyclopentyl and cyclohexyl groups are preferred.

Where $R^2$ represents a substituted cycloalkyl group, this may be any of the cycloalkyl groups exemplified above, preferably having from 3 to 6 ring carbon atoms and may be substituted by at least one substituent selected from the group consisting of substituents α, defined and exemplified above. As before, there is no particular limitation on the number of such substituents, except such as may be imposed by the number of substitutable carbon atoms and possibly by steric constraints, and the preferred number of substituents depends on the nature of the substituent. In this case, where the substituent is a halogen atom, the preferred number is from 1 to 3. In the case of the other substituents, a single substituent is preferred. Where there are two or more substituents, these may be the same or different. Examples of such substituted groups include the 1-chlorocyclopentyl, 1-chlorocyclohexyl, 1-hydroxycyclopropyl, 1-hydroxycyclobutyl, 1-hydroxycyclopentyl, 3-hydroxycyclopentyl, 1-hydroxycyclohexyl, 4-hydroxycyclohexyl, 1-hydroxycycloheptyl, 1-aminocyclopentyl, 1-aminocyclohexyl, 1-(methylamino)cyclopentyl, 1-(methylamino)cyclohexyl, 1-(N,N-dimethyl-amino)cyclopentyl, 1-(N,N-dimethylamino)cyclohexyl, 1-formylcyclopentyl, 1-formylcyclohexyl, 1-acetylcyclo-pentyl, 1-acetylcyclohexyl, 1-methoxycyclopropyl, 1-methoxycyclobutyl, 1-methoxycyclopentyl, 1-methoxycyclohexyl, 1-methylthiocyclopentyl, 1-methylthiocyclohexyl, 1-cyanocyclopentyl, 1-cyanocyclohexyl, 1-nitrocyclopentyl and 1-nitrocyclohexyl groups, of which we prefer the 1-hydroxycyclopentyl, 1-hydroxycyclohexyl, 1-methoxycyclopentyl and 1-methoxycyclohexyl groups.

Where $R^2$ or substituent α represents a halogen atom, this may be, for example, a fluorine, chlorine, bromine or iodine atom, preferably a fluorine, chlorine or bromine atom, more preferably a fluorine or chlorine atom.

Where $R^5$ or Z represents an alkylene group, this may be a straight or branched chain group having from 1 to 4, preferably 1 or 2, carbon atoms. Where the "free" valence is present on the same carbon atom, such groups are sometimes referred to as "alkylidene" groups, although groups where the "free" valence is present on the same carbon atom and those where it is present on different atoms are herein collectively called "alkylene" groups, as is more conventional. Examples of such groups include the methylene, ethylene, trimethylene, tetramethylene, ethylidene, propylidene, butylidene and isobutylidene groups, preferably the methylene and ethylene groups, and most preferably the methylene group.

Where $R^3$ or B represents a protected carboxy group, or $R^6$ represents a carboxy-protecting group, the carboxy-protecting group may be any one of those which are widely known in the field of synthetic organic chemistry or it may be an ester residue which can be converted to a carboxy group in the living body. Examples of such protecting groups include:

alkyl groups having from 1 to 6 carbon atoms, such as those exemplified above in relation to the alkyl groups which may be represented by $R^1$ especially the methyl ethyl and t-butyl groups;

haloalkyl groups having from 1 to 6, preferably from 1 to 4, carbon atoms, such as the trifluoromethyl, 2,2,2-trifluoroethyl, 2,2,2-trichloroethyl, 2-fluoroethyl, 2-chloroethyl, 2-iodoethyl, 3-chloropropyl, 4-fluorobutyl and 6-iodohexyl groups, preferably the 2,2,2-trichloroethyl and 2-chloroethyl groups;

hydroxyalkyl groups having from 1 to 6, preferably from 2 to 4, carbon atoms, and having one or more, preferably 1 or 2, hydroxy groups, such as the hydroxymethyl, 2-hydroxyethyl, 2,3-dihydroxypropyl, 3-hydroxypropyl, 3,4-dihydroxybutyl, 4-hydroxybutyl, 5-hydroxypentyl and 6-hydroxyhexyl groups, preferably the 2-hydroxyethyl group;

alkoxyalkyl and alkoxyalkoxyalkyl groups in which the or each alkoxy group and the alkyl group each has from 1 to 6, preferably from 1 to 4, more preferably 1 or 2, carbon atoms, such as the methoxymethyl, 2-methoxyethyl, 2-ethoxyethyl and 2-methoxyethoxymethyl groups, preferably the methoxymethyl group;

the phenacyl group;

alkoxycarbonylalkyl groups in which the alkoxy group and the alkyl group each have from 1 to 6, preferably from 1 to 4, more preferably 1 or 2, carbon atoms, such as the methoxycarbonylmethyl group;

cyanoalkyl groups in which the alkyl part has from 1 to 6, preferably from 1 to 4, more preferably 1 or 2, carbon atoms, such as the cyanomethyl and 2-cyanoethyl groups;

alkylthiomethyl groups in which the alkyl part has from 1 to 6, preferably from 1 to 4, more preferably 1 or 2, carbon atoms, such as the methylthiomethyl and ethylthiomethyl groups;

arylthiomethyl groups, in which the aryl part has from 6 to 10, preferably 6 or 10, carbon atoms, such as the phenylthiomethyl and naphthylthiomethyl groups;

alkylsulfonylalkyl groups in which each alkyl part has from 1 to 6, preferably from 1 to 4, more preferably 1 or 2, carbon atoms, and in which the alkyl group of the alkylsulfonyl part may be unsubstituted or substituted with one or moer, preferably from 1 to 3, halogen atoms, such as the 2-methanesulfonylethyl and 2-trifluoromethanesulfonylethyl groups;

arylsulfonylalkyl groups in which the aryl part has from 6 to 10, preferably 6 or 10, ring carbon atoms and the alkyl part has from 1 to 6, preferably from 1 to 4, more preferably 1 or 2, carbon atoms, such as the 2-benzenesulfonylethyl and 2-toluenesulfonylethyl groups;

aralkyl groups in which an alkyl group is substituted by one or more (preferably from 1 to 3, more preferably 1 or 2) aryl groups, each having from 6 to 10, preferably 6 or 10, carbon atoms and being optionally substituted by one or more alkyl, alkoxy or halogen substituents; the alkyl part has from 1 to 6, preferably from 1 to 4, more preferably 1 or 2, carbon atoms and the aralkyl group itself preferably has from 7 to 13 carbon atoms in total in the aryl and alkyl parts, such as the benzyl, phenethyl, 3-phenylpropyl, 4-phenylbutyl, diphenylmethyl and naphthylmethyl groups;

aryl groups having from 6 to 10 carbon atoms, such as the phenyl and naphthyl groups;

alkanoyloxyalkyl groups in which the alkanoyl group has from 1 to 6, preferably from 2 to 5, carbon atoms and the alkyl group has from 1 to 6, preferably from 1 to 4, more preferably 1 or 2, carbon atoms, such as the formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypennyl, 1-pivaloyloxypentyl and 1-pivaloyloxyhexyl groups, of which we prefer the formyloxymethyl, acetoxymethyl, propionyloxymethyl, butyryloxymethyl, pivaloyloxymethyl, 1-formyloxyethyl, 1-acetoxyethyl, 1-propionyloxyethyl, 1-butyryloxyethyl and 1-pivaloyloxyethyl groups, more preferably the acetoxymethyl, propionyloxymethyl, butyryloxymethyl, pivaloyloxymethyl, 1-acetoxyethyl, 1-propionyloxyethyl, 1-butyryloxyethyl and 1-pivaloyloxymethyl groups, and most preferably the pivaloyloxymethyl and 1-pivaloyloxyethyl groups;

cycloalkanecarbonyloxyalkyl groups in which the cycloalkane group has 5 or 6 carbon atoms and the alkyl group has from 1 to 6, preferably 1 to 4, more preferably 1 or 2, carbon atoms, such as the cyclopentanecarbonyloxymethyl, cyclohexanecarbonyloxymethyl, 1-cyclopentanecarbonyloxyethyl, 1-cyclohexanecarbonyloxyethyl, 1-cyclopentanecarbonyloxypropyl, 1-cyclohexanecarbonyloxypropyl, 1-cyclopentanecarbonyloxybutyl, and 1-cyclohexanecarbonyloxybutyl groups, of which we prefer the cyclopentanecarbonyloxymethyl, cyclohexanecarbonyloxymethyl, 1-cyclopentanecarbonyloxyethyl and 1-cyclohexanecarbonyloxyethyl groups;

alkoxycarbonyloxyalkyl groups in which the alkoxy group and the alkyl group each have from 1 to 6, preferably from 1 to 5, more preferably 1 or 2, carbon atoms for the alkyl part, and preferably from 1 to 4 carbon atoms for the alkoxy part, such as the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-pentyloxycarbonyloxyethyl, 1-hexyloxycarbonyloxyethyl, 2-methoxycarbonyloxyethyl, 2-ethoxycarbonyloxyethyl, 2-propoxycarbonyloxyethyl, 2-isopropoxycarbonyloxyethyl, 2-butoxycarbonyloxyethyl, 2-isobutoxycarbonyloxyethyl, 2-pentyloxycarbonyloxyethyl, 2-hexyloxycarbonyloxyethyl, 1-methoxycarbonyloxylpropyl, 1-ethoxycarbonyloxypropyl, 1-propoxycarbonyloxypropyl, 1-isopropoxycarbonyloxypropyl, 1-butoxycarbonyloxypropyl, 1-isobutoxycarbonyloxypropyl, 1-pentyloxycarbonyloxypropyl, 1-hexyloxycarbonyloxypropyl, 1-methoxycarbonyloxybutyl, 1-ethoxycarbonyloxybutyl, 1-propoxycarbonyloxybutyl, 1-isopropoxycarbonyloxybutyl, 1-butoxycarbonyloxybutyl, 1-isobutoxycarbonyloxybutyl, 1-methoxycarbonyloxypentyl, 1-ethoxycarbonyloxypentyl, 1-methoxycarbonyloxyhexyl and 1-ethoxycarbonyloxyhexyl groups, of which we prefer the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-methoxycarbonyloxypropyl, 1-ethoxycarbonyloxypropyl, 1-propoxycarbonyloxypropyl, 1-isopropoxycarbonyloxypropyl, 1-butoxycarbonyloxypropyl, 1-isobutoxycarbonyloxypropyl, 1-methoxycarbonyloxybutyl, 1-ethoxycarbonyloxybutyl, 1-propoxycarbonyloxybutyl, 1-isopropoxycarbonyloxybutyl, 1-butoxycarbonyloxybutyl and 1-isobutoxycarbonyloxybutyl groups, more preferably the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl groups, and most preferably the methoxycarbonyloxymethyl, ethoxycarbonyloxymethyl, isopropoxycarbonyloxymethyl, 1-methoxycarbonyloxyethyl, 1-ethoxycarbonyloxyethyl and 1-isopropoxycarbonyloxyethyl groups;

cycloalkoxycarbonyloxyalkyl groups in which the cycloalkane group has 5 or 6 carbon atoms and the alkyl group has from 1 to 6, preferably from 1 to 4, more preferably 1 or 2, carbon atoms, such as the cyclopentyloxycarbonyloxymethyl, cyclohexyloxycarbonyloxymethyl, 1-cyclopentyloxycarbonyloxyethyl, 1-cyclohexyloxycarbonyloxyethyl, 1-cyclopentyloxycarbonyloxypropyl, 1-cyclohexyloxycarbonyloxypropyl, 1-cyclopentyloxycarbonyloxybutyl, and 1-cyclohexyloxycarbonyloxybutyl groups, of which we prefer the cyclopentyloxycarbonyloxymethyl, cyclohexyloxycarbonyloxymethyl, 1-cyclopentyloxycarbonyloxyethyl and 1-cyclohexyloxycarbonyloxyethyl groups;

(5-aryl- or 5-alkyl-2-oxo-1,3-dioxolen-4-yl)methyl groups in which the aryl part has from 6 to 10, preferably 6 or 10, carbon atoms and is optionally substituted by one or more alkyl, alkoxy or halogen substituents, and the alkyl part has from 1 to 6, preferably from 1 to 4, more preferably 1 or 2, carbon atoms, such as the (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4yl)methyl groups, of which we prefer the 5-phenyl-2-oxo-1,3-dioxolen-4-yl)methyl, (5-methyl-2-oxo-1,3-dioxolen-4-yl)methyl and (5-ethyl-2-oxo-1,3-dioxolen- 4-yl)methyl groups, most preferably the (5-methyl-2- oxo-1,3-dioxolen-4-yl)methyl group; and the phthalidyl group.

Those of the above protecting groups which contain aryl rings may be substituted or unsubstituted, and, if substituted, may contain one or more alkyl groups having from 1 to 6 carbon atoms, alkoxy groups having from 1 to 6 carbon atoms, or halogen atoms, all of which may be as individually exemplified hereinabove.

Preferred protecting groups are: alkyl groups having from 1 to 4 carbon atoms; the phenyl group; the naphthyl group; the benzyl group; benzyl groups which have at least one substituent selected from the group consisting of methyl, ethyl, methoxy, ethoxy, fluorine and chlorine substituents; the diphenylmethyl group; the naphthylmethyl group; alkanoyloxyalkyl groups in which the alkanoyl part has from 1 to 5 carbon atoms and the alkyl part has from 1 to 4 carbon atoms; cycloalkanecarbonyloxyalkyl groups in which the cycloalkane part has 5 or 6 carbon atoms and the alkyl part has from 1 to 4 carbon atoms; alkoxycarbonyloxyalkyl groups in which the alkoxy and alkyl parts both have from 1 to 4 carbon atoms; cycloalkoxycarbonyloxyalkyl groups in which the cycloalkane part has 5 or 6 carbon atoms and the alkyl part has from 1 to 4 carbon atoms; (5-phenyl- or 5-alkyl-2-oxo-1,3-dioxolen-4-yl)methyl groups in which the alkyl part has from 1 to 4 carbon atoms; and the phthalidyl group.

More preferred protecting groups are: alkyl groups having from 1 to 4 carbon atoms; the benzyl group; alkanoyloxyalkyl groups in which the alkanoyl part has from 1 to 5 carbon atoms and the alkyl part has 1 or 2 carbon atoms; cycloalkanecarbonyloxyalkyl groups in which the cycloalkane part has 5 or 6 carbon atoms and the alkyl part has 1 or 2 carbon atoms; alkoxycarbonyloxyalkyl groups in which the alkoxy part has from 1 to 4 carbon atoms and the alkyl part has 1 or 2 carbon atoms; cycloalkoxycarbonyloxyalkyl groups in which the cycloalkane part has 5 or 6 carbon atoms and the alkyl part has 1 or 2 carbon atoms; (5-phenyl- or 5-alkyl-2-oxo-1,3-dioxolen-4-yl]methyl groups in which the alkyl part has 1 or 2 carbon atoms; and the phthalidyl group.

Still more preferred protecting groups are: alkanoyloxyalkyl groups in which the alkanoyl part has from 2 to 5 carbon atoms and the alkyl part has 1 or 2 carbon atoms; alkoxycarbonyloxyalkyl groups in which the alkoxy part has from 1 to 4 carbon atoms and the alkyl part has 1 or 2 carbon atoms; cycloalkoxycarbonyloxyalkyl groups in which the cycloalkane part has 5 or 6 carbon atoms and the alkyl part has 1 or 2 carbon atoms; and the (5-methyl-2-oxo-1,3-dioxolen-4-yl)methyl group.

The most preferred protecting groups are: the acetoxymethyl group; the pivaloyloxymethyl group, the ethoxycarbonyloxymethyl group, the 1-(ethoxycarbonyloxy)ethyl group, the isopropoxycarbonyloxymethyl group, the 1-(isopropoxycarbonyloxy)ethyl group, the cyclohexyloxycarbonyloxymethyl group, the 1-(cyclohexyloxycarbonyloxy)ethyl group and the (5-methyl-2-oxo-1,3-dioxolen- 4-yl)methyl group.

The compounds of the present invention can form salts. There is no particular restriction on the nature of such salts, provided that, where they are intended for therapeutic use, they are pharmaceutically acceptable, which, as is well known, means that they are not less active (or unacceptably less active) or more toxic (or unacceptably more toxic) than the parent compound. Thus, since the compound of the present invention contains at least one basic group in its molecule, it can form acid addition salts. Examples of such acid addition salts include: salts with inorganic acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or N-toluenesulfonic acid; and salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid. Such acid addition salts may be prepared by reacting the compound of formula (I) with an acid under conventional conditions.

Also, where the compound of the present invention is one in which $R^3$ and/or B represents a carboxy group or a tetrazole group and/or X represents a group of formula —$C(COOR^6)$=, where $R^6$ represents a hydrogen atom, reaction of this compound with a base will yield a salt. Examples of such salts include: salts with an alkali metal, such as sodium, potassium or lithium; salts with an alkaline earth metal, such as barium or calcium; salts with another metal, such as magnesium or aluminum; ammonium salts; and organic base salts, such as a salt with triethylamine, diisopropylamine, cyclohexylamine, guanidine or dicyclohexylamine.

The compounds of the present invention may contain one or more asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Preferred classes of compounds of the present invention are those compounds of formula (I) and pharmaceutically acceptable salts and esters thereof, wherein:

1(i). A represents a group of formula (IIa), and $R^1$ represents an alkyl group having from 2 to 4 carbon atoms, an alkenyl group having from 3 to 5 carbon atoms, an alkoxyalkyl group in which the alkoxy part has from 1 to 3 carbon atoms and the alkyl part has 1 or 2 carbon atoms, an alkylthioalkyl group in which the alkylthio part has from 1 to 3 carbon atoms and the alkyl part has 1 or 2 carbon atoms, or an alkylthio group having from 1 to 3 carbon atoms;

1(ii). A represents a group of formula (IIa), and $R^2$ represents a hydrogen atom, a halogen atom, an alkyl group having from 1 to 6 carbon atoms, an alkenyl group having from 3 to 6 carbon atoms or a substituted alkyl group which has from 1 to 6 carbon atoms and which is substituted by a halogen atom or a hydroxyl group;

1(iii). A represents a group of formula (IIa), and $R^3$ represents a carboxy group, a protected carboxy group, a carbamoyl group or a tetrazol-5-yl group;

1(iv). A represents a group of formula (IIa), and Z represents a single bond, a methylene group or a vinylene group;

and particularly those in which A represents a group of formula (IIa), and $R^1$ is as defined in 1(i), $R^2$ is as defined in 1(ii), $R^3$ is as defined in 1(iii) and Z is as defined in 1(iv).

2(i). A represents a group of formula (IIb), and $R^1$ represents an alkyl group having from 2 to 4 carbon atoms, a cyclopropyl group, an alkoxyalkyl group in which the alkoxy part has from 1 to 3 carbon atoms and the alkyl part has 1 or 2 carbon atoms, an alkylthioalkyl group in which the alkylthio part has from 1 to 3 carbon atoms and the alkyl part has 1 or 2 carbon atoms, an alkoxy group having from 1 to 3 carbon atoms or an alkylthio group having from 1 to 3 carbon atoms;

2(ii). A represents a group of formula (IIb), and $R^2$ represents a hydrogen atom, a halogen atom or an alkyl group having from 1 to 4 carbon atoms;

2(iii). A represents a group of formula (IIb), and $R^3$ represents a hydrogen atom, an alkyl group having from 1 to 4 carbon atoms, a carboxy group, a protected carboxy group or a tetrazol-5-yl group;

2(iv). A represents a group of formula (IIb), and X represents a group of formula —CH=, a group of formula —N= or a group of formula —$C(COOR^6)$=, wherein $R^6$ represents a hydrogen atom or a carboxy-protecting group;

2(v). A represents a group of formula (IIb), and Z represents a single bond, a methylene group or a vinylene group;

and particularly those in which A represents a group of formula (IIb), and $R^1$ is as defined in 2(i), $R^2$ is as defined in 2(ii), $R^3$ is as defined in 2(iii), X is as defined in 2(iv) and Z is as defined in 2(v). 3(i). A represents a group of formula (IIc), and $R^1$ represents an alkyl group having from 2 to 4 carbon atoms, an alkoxyethyl group in which the alkoxy part has from 1 to 3 carbon atoms or an alkylthioethyl group in which the alkylthio part has from 1 to 3 carbon atoms;

3(ii). A represents a group of formula (IIc), and $R^2$ represents a hydrogen atom, a halogen atom or an alkyl group having from 1 to 4 carbon atoms;

3(iii). A represents a group of formula (IIc), and $R^3$ represents a hydrogen atom, an alkyl group having from 1 to 4 carbon atoms, a carboxy group, a protected carboxy group or a tetrazol-5-yl group;

3(iv). A represents a group of formula (IIc), and X represents a group of formula —CH= or a group of formula —N=;

3(v). A represents a group of formula (IIc), and Z represents a single bond, a methylene group or a vinylene group;

and particularly those in which A represents a group of formula (IIc), and $R^1$ is as defined in 3(i), $R^2$ is as defined in 3(ii), $R^3$ is as defined in 3(iii), X is as defined in 3(iv) and Z is as defined in 3(v).

4. Where $R^3$ or B represents a protected carboxy group or $R^6$ represents a carboxy-protecting group, the protecting group is an alkanoyloxyalkyl group in which the alkanoyl part has from 2 to 5 carbon atoms and the alkyl part has 1 or 2 carbon atoms, an alkoxycarbonyloxyalkyl group in which the alkoxy part has from 1 to 4 carbon atoms and the alkyl part has 1 or 2 carbon atoms, a cycloalkoxycarbonyloxyalkyl group in which the cycloalkane part has 5 or 6 carbon atoms and the alkyl part has 1 or 2 carbon atoms, or a (5-methyl-2-oxo-1,3-dioxolen-4-yl)methyl group.

5. B represents a carboxy group or a tetrazol-5-yl group.

More preferred classes of compounds of the present invention are those compounds of formula (I) and pharmaceutically acceptable salts and esters thereof, wherein:

6(i). A represents a group of formula (IIa), and $R^1$ represents an ethyl, propyl, butyl, 1-propenyl, 1-butenyl, 2-butenyl, methoxymethyl, ethoxymethyl, methylthiomethyl, ethylthiomethyl, methylthio or ethylthio group;

6(ii). A represents a group of formula (IIa), and $R^2$ represents a chlorine atom, a bromine atom, or a methyl, ethyl, isopropyl, isopropenyl, trifluoromethyl, pentafluoroethyl, hydroxymethyl, 1-hydroxyethyl, 1-hydroxy-1-methylethyl, 1-hydroxypropyl, 1-hydroxy-1-methylpropyl, 1-hydroxy-2-methylpropyl or 1-hydroxy-2,2-dimethylpropyl group;

6(iii). A represents a group of formula (IIa), and $R^3$ represents a carboxy group, a protected carboxy group, a carbamoyl group or a tetrazol-5-yl group;

6(iv). A represents a group of formula (IIa), and Z represents a single bond or a methylene group;

and particularly those in which A represents a group of formula (IIa), and $R^1$ is as defined in 6(i), $R^2$ is as defined in 6(ii), $R^3$ is as defined in 6(iii) and Z is as defined in 6(iv).

7(i). A represents a group of formula (IIb), and $R^1$ represents an ethyl, propyl, cyclopropyl, methoxy, ethoxy, propoxy, methylthio or ethylthio group;

7(ii). A represents a group of formula (IIb), and $R^2$ represents a hydrogen atom, a fluorine atom, a chlorine atom, or a methyl, ethyl or isopropyl group;

7(iii). A represents a group of formula (IIb), and $R^3$ represents a hydrogen atom, or a methyl, ethyl, carboxy, protected carboxy or tetrazol-5-yl group;

7(iv). A represents a group of formula (IIb), and X represents a group of formula —CH=, a group of formula —N= or a group of formula —C(COOR$^6$)=, wherein $R^6$ represents a hydrogen atom or a carboxy-protecting group;

7(v). A represents a group of formula (IIb), and Z represents a single bond or a methylene group;

and particularly those in which A represents a group of formula (IIb), and $R^1$ is as defined in 7(i), $R^2$ is as defined in 7(ii), $R^3$ is as defined in 7(iii), X is as defined in 7(iv) and Z is as defined in 7(v).

8(i). A represents a group of formula (IIc), and $R^1$ represents an ethyl, propyl, butyl, 2-methoxyethyl or 2-methylthioethyl group;

8(ii). A represents a group of formula (IIc), and $R^2$ represents a hydrogen atom, a fluorine atom, a chlorine atom, or a methyl, ethyl or isopropyl group;

8(iii). A represents a group of formula (IIc), and $R^3$ represents a hydrogen atom, or a methyl, ethyl, carboxy, protected carboxy or tetrazol-5-yl group;

8(iv). A represents a group of formula (IIc), and X represents a group of formula —CH= or a group of formula —N=;

8(v). A represents a group of formula (IIc), and Z represents a single bond or a methylene group;

and particularly those in which A represents a group of formula (IIc), and $R^1$ is as defined in 8(i), $R^2$ is as defined in 8(ii), $R^3$ is as defined in 8(iii), X is as defined in 8(iv) and Z is as defined in 8(v).

9. Where $R^3$ or B represents a protected carboxy group or $R^6$ represents a carboxy-protecting group, the protecting group is an acetoxymethyl, pivaloyloxymethyl, ethoxycarbonyloxymethyl, isopropoxycarbonyloxymethyl, 1-ethoxycarbonyloxyethyl, 1-isopropoxycarbonyloxyethyl, cyclohexyloxycarbonyloxymethyl, 1-cyclohexyloxycarbonyloxyethyl or (5-methyl-2-oxo-1,3-dioxolen-4-yl)methyl group.

The most preferred classes of compounds of the present invention are those compounds of formula (I) and pharmaceutically acceptable salts and esters thereof, wherein:

10(i). A represents a group of formula (IIa), and $R^1$ represents an ethyl, propyl or butyl group;

10(ii). A represents a group of formula (IIa), and $R^2$ represents a chlorine atom, or an isopropyl, isopropenyl, trifluoromethyl, pentafluoroethyl, 1-hydroxyethyl or 1-hydroxy-1-methylethyl group; and $R^3$ represents a carboxy group, a protected carboxy group or a tetrazol-5-yl group;

10(iii). A represents a group of formula (IIa), and $R^2$ represents a 1-hydroxy-2-methylpropyl or 1-hydroxy-2,2-dimethylpropyl group, and $R^3$ represents a carbamoyl group;

10(iv). A represents a group of formula (IIa), and Z represents a single bond;

and particularly those in which A represents a group of formula (IIa), and $R^1$ is as defined in 10(i), $R^2$ and $R^3$ are as defined in 10(ii) or in 10(iii) and Z is as defined in 10(iv).

11(i). A represents a group of formula (IIb), and $R^1$ represents an ethyl, propyl, cyclopropyl, ethoxy, methylthio or ethylthio group;

11(ii). A represents a group of formula (IIb), and $R^2$ represents a hydrogen atom or a methyl group;

11(iii). A represents a group of formula (IIb), and $R^3$ represents a hydrogen atom, or a methyl, carboxy, protected carboxy or tetrazol-5-yl group;

11(iv). A represents a group of formula (IIb), and X represents a group of formula —CH=, a group of formula —N= or a group of formula —C(COOR$^6$)=, wherein $R^6$ represents a hydrogen atom or a carboxy-protecting group;

11(v). A represents a group of formula (IIb), and Z represents a single bond;

and particularly those in which A represents a group of formula (IIb), and $R^1$ is as defined in 11(i), $R^2$ is as defined in 11(ii), $R^3$ is as defined in 11(iii), X is as defined in 11(iv) and Z is as defined in 11(v).

12(i). A represents a group of formula (IIc), and $R^1$ represents an ethyl, propyl, butyl, 2-methoxyethyl or 2-methylthioethyl group;

12(ii). A represents a group of formula (IIc), and $R^2$ represents a hydrogen atom or a methyl group;

12(iii). A represents a group of formula (IIc), and $R^3$ represents a carboxy, protected carboxy or tetrazol-5-yl group;

12(iv). A represents a group of formula (IIc), and X represents a group of formula —CH=;

12(v). A represents a group of formula (IIc), and Z represents a single bond;

and particularly those in which A represents a group of formula (IIc), and $R^1$ is as defined in 12(i), $R^2$ is as defined in 12(ii), $R^3$ is as defined in 12(iii), X is as defined in 12(iv) and Z is as defined in 12(v).

13. Where $R^3$ or B represents a protected carboxy group or $R^6$ represents a carboxy-protecting group, the protecting group is an acetoxymethyl, pivaloyloxymethyl, ethoxycarbonyloxymethyl, isopropoxycarbonyloxymethyl, 1-ethoxycarbonyloxyethyl, 1-isopropoxycarbonyloxyethyl, cyclohexyloxycarbonyloxymethyl, 1-cyclohexyloxycarbonyloxyethyl or (5-methyl-2-oxo-1,3- dioxolen-4-yl)methyl group.

Specific examples of individual compounds of the present invention are given by the following formulae (I-1) to (I-3), in which the various symbols used are as defined in the corresponding one of Tables 1 to 3, that is Table 1 relates to formula (I-1), Table 2 relates to formula (I-2) and Table 3 relates to formula (I-3). For the avoidance of doubt, the peripheral numbering systems used to identify the positions of substituents on the heterocyclic rings in formulae (I-2) and (I-3) are shown. It should be noted that, for convenience and clarity, the peripheral numbering system used to identify the positions of substituents on the heterocyclic rings in formula (I-2) when X represents a group of formula —N= is shown in partial formula (I-2a), whilst that used to identify the positions of substituents on the heterocyclic ring in formula (I-2) when X represents a group of formula —CH= or —C(COOR$^6$)= is shown in partial formulae (I-2b) and (I-2c), respectively. The same numbering systems, which are in accordance with the recommendations of the International Union of Pure and Applied Chemistry, are used hereafter in naming the compounds. In the Tables, the following abbreviations are used for certain groups:

Bu butyl
tBu t-butyl
Et ethyl
cHx cyclohexyl
Me methyl
Mod (5-methyl-2-oxo-1,3-dioxolen-4-yl)methyl
Pom pivaloyloxymethyl
Pr propyl
cPr cyclopropyl
iPr isopropyl
Tz tetrazol-5-yl

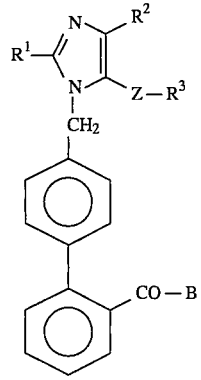

TABLE 1

| Cpd. No. | R | R$^2$ | Z—R$^3$— | B |
|---|---|---|---|---|
| 1-1 | Et | C(Me$_2$)OH | COOH | COOH |
| 1-2 | Pr | C(Me$_2$)OH | COOH | COOH |
| 1-3 | Bu | C(Me$_2$)OH | COOH | COOH |
| 1-4 | Pr | CH$_2$OH | COOH | COOH |

TABLE 1-continued

| Cpd. No. | R | R² | Z—R³— | B |
|---|---|---|---|---|
| 1-5 | Bu | CH₂OH | COOH | COOH |
| 1-6 | Pr | CH(ME)OH | COOH | COOH |
| 1-7 | Bu | CH(ME)OH | COOH | COOH |
| 1-8 | Pr | CH(ME₂) | COOH | COOH |
| 1-9 | Bu | CH(ME₂) | COOH | COOH |
| 1-10 | Pr | C(=CH₂)Me | COOH | COOH |
| 1-11 | Bu | C(=CH₂)Me | COOH | COOH |
| 1-12 | Pr | Et | COOH | COOH |
| 1-13 | Bu | Et | COOH | COOH |
| 1-14 | Pr | Me | COOH | COOH |
| 1-15 | Bu | Me | COOH | COOH |
| 1-16 | Pr | Cl | COOH | COOH |
| 1-17 | Bu | Cl | COOH | COOH |
| 1-18 | Pr | CF₃ | COOH | COOH |
| 1-19 | Bu | CF₃ | COOH | COOH |
| 1-20 | Pr | C₂H₅ | COOH | COOH |
| 1-21 | Bu | C₂H₅ | COOH | COOH |
| 1-22 | Pr | CH(iPr)OH | CONH₂ | COOH |
| 1-23 | Bu | CH(iPr)OH | CONH₂ | COOH |
| 1-24 | Pr | CH(tBu)OH | CONH₂ | COOH |
| 1-25 | Bu | CH(tBu)OH | CONH₂ | COOH |
| 1-26 | Pr | C(Me₂)OH | COOEt | COOH |
| 1-27 | Pr | C(Me₂)OH | COOPom | COOH |
| 1-28 | Pr | C(Me₂)OH | COOMod | COOH |
| 1-29 | Pr | C(Me₂)OH | COOCH₂OCOOEt | COOH |
| 1-30 | Pr | C(Me₂)OH | COOCH₂OCOOiPr | COOH |
| 1-31 | Pr | C(Me₂)OH | COOCH(Me)OCOOEt | COOH |
| 1-32 | Pr | C(Me₂)OH | COOCH(Me)OCOOiPr | COOH |
| 1-33 | MeCH=CH— | C(Me₂)OH | COOH | COOH |
| 1-34 | EtCH=CH— | C(Me₂)OH | COOH | COOH |
| 1-35 | MeCH=CHCH₂— | C(Me₂)OH | COOH | COOH |
| 1-36 | MeOCH₂ | C(Me₂)OH | COOH | COOH |
| 1-37 | EtOCH₂ | C(Me₂)OH | COOH | COOH |
| 1-38 | MeSCH₂ | C(Me₂)OH | COOH | COOH |
| 1-39 | EtSCH₂ | C(Me₂)OH | COOH | COOH |
| 1-40 | Pr | C(Me₂)OH | Tz | COOH |
| 1-41 | Bu | C(Me₂)OH | Tz | COOH |
| 1-42 | Pr | C(Me₂)OH | COOH | Tz |
| 1-43 | Bu | C(Me₂)OH | COOH | Tz |
| 1-44 | Pr | C(Me₂)OH | CH₂COOH | COOH |
| 1-45 | Pr | iPr | CH₂COOH | COOH |
| 1-46 | Pr | C(Me₂)OH | CH=CHCOOH | COOH |
| 1-47 | Pr | iPr | CH=CHCOOH | COOH |
| 1-48 | MeNHCH₂ | C(Me₂)OH | COOH | COOH |
| 1-49 | EtNHCH₂ | C(Me₂)OH | COOH | COOH |
| 1-50 | Pr | C(Me₂)OH | COOET | Tz |

TABLE 2

| Cpd. No. | R¹ | R² | —Z—R³— | X | B |
|---|---|---|---|---|---|
| 2-1 | Et | 7-Me | 5-Me | =N— | COOH |
| 2-2 | Pr | 7-Me | 5-Me | =N— | COOH |
| 2-3 | Bu | 7-Me | 5-Me | =N— | COOH |
| 2-4 | cPr | 7-Me | 5-Me | =N— | COOH |
| 2-5 | Et | 7-Me | H | =N— | COOH |
| 2-6 | Pr | 7-Me | H | =N— | COOH |
| 2-7 | cPr | 7-Me | H | =N— | COOH |
| 2-8 | Et | 5-Me | H | =N— | COOH |
| 2-9 | Pr | 5-Me | H | =N— | COOH |
| 2-10 | cPr | 5-Me | H | =N— | COOH |
| 2-11 | Et | 7-Me | 5-Et | =N— | COOH |
| 2-12 | Et | H | H | =N— | COOH |
| 2-13 | Pr | H | H | =N— | COOH |
| 2-14 | Et | H | 5-COOH | =N— | COOH |
| 2-15 | Pr | H | 5-COOH | =N— | COOH |
| 2-16 | Et | 7-Me | 5-COOH | =N— | COOH |
| 2-17 | Pr | 7-Me | 5-COOH | =N— | COOH |
| 2-18 | Et | H | 5-CH₂COOH | =N— | COOH |
| 2-19 | Pr | H | 5-CH₂COOH | =N— | COOH |
| 2-20 | Et | H | 5-CH=CHCOOH | =N— | COOH |
| 2-21 | Pr | H | 5-CH=CHCOOH | =N— | COOH |

TABLE 2-continued

| Cpd. No. | R¹ | R² | —Z—R³— | X | B |
|---|---|---|---|---|---|
| 2-22 | Et | H | 6-COOH | =CH— | COOH |
| 2-23 | Pr | H | 6-COOH | =CH— | COOH |
| 2-24 | Et | 7-Me | 6-COOH | =CH— | COOH |
| 2-25 | Pr | 7-Me | 6-COOH | =CH— | COOH |
| 2-26 | Et | H | H | =C(COOH)— | COOH |
| 2-27 | Pr | H | H | =C(COOH)— | COOH |
| 2-28 | Et | H | H | =C(COOPom)— | COOH |
| 2-29 | Pr | H | H | =C(COOPom)— | COOH |
| 2-30 | Et | H | H | =C(COOMod)— | COOH |
| 2-31 | Pr | H | H | =C(COOMod)— | COOH |
| 2-32 | Et | H | H | =C(COOCH$_2$OCOOEt)— | COOH |
| 2-33 | Pr | H | H | =C(COOCH$_2$OCOOEt)— | COOH |
| 2-34 | Et | H | H | =C(COOCH$_2$OCOocHx)— | COOH |
| 2-35 | Pr | H | H | =C(COOCH$_2$OCOocHx)— | COOH |
| 2-36 | Et | H | H | =C[COOCH(Me)OCOOEt]— | COOH |
| 2-37 | Pr | H | H | =C[COOCH(Me)OCOOEt]— | COOH |
| 2-38 | Et | H | H | =C[COOCH(Me)OCOocHx]— | COOH |
| 2-39 | Pr | H | H | =C[COOCH(Me)OCOocHx]— | COOH |
| 2-40 | EtO | 7-Me | 5-Me | =N— | COOH |
| 2-41 | PrO | 7-Me | 5-Me | =N— | COOH |
| 2-42 | MeS | 7-Me | 5-Me | =N— | COOH |
| 2-43 | EtS | 7-Me | 5-Me | =N— | COOH |
| 2-44 | EtO | H | H | =C(COOH)— | COOH |
| 2-45 | EtO | H | H | =C(COOPom)— | COOH |
| 2-46 | EtO | H | H | =C(COOMod)— | COOH |
| 2-47 | EtO | H | H | =C(COOCH$_2$OCOOET)— | COOH |
| 2-48 | EtO | H | H | =C(COOCH$_2$OCOocHx)— | COOH |
| 2-49 | EtO | H | H | =C[COOCH(Me)OCOOEt]— | COOH |
| 2-50 | EtO | H | H | =C[COOCH(Me)OCOocHx]— | COOH |
| 2-51 | Et | 7-Me | 5-Me | =N— | Tz |
| 2-52 | Et | H | H | =C(COOH)— | Tz |
| 2-53 | Bu | H | 5-COOH | =CH— | COOH |
| 2-54 | Bu | H | 6-COOH | =CH— | COOH |

TABLE 3

| Cpd. No. | R¹ | R² | —Z—R³— | X | B |
|---|---|---|---|---|---|
| 3-1 | Et | H | 5-COOH | =CH— | COOH |
| 3-2 | Pr | H | 5-COOH | =CH— | COOH |
| 3-3 | Bu | H | 5-COOH | =CH— | COOH |
| 3-4 | Et | H | 5-Tz | =CH— | COOH |
| 3-5 | Pr | H | 5-Tz | =CH— | COOH |
| 3-6 | Bu | H | 5-Tz | =CH— | COOH |
| 3-7 | Et | 4-Me | 5-COOH | =CH— | COOH |
| 3-8 | Pr | 4-Me | 5-COOH | =CH— | COOH |
| 3-9 | Bu | 4-Me | 5-COOH | =CH— | COOH |
| 3-10 | Pr | 4-Et | 5-COOH | =CH— | COOH |
| 3-11 | Pr | 4-iPr | 5-COOH | =CH— | COOH |
| 3-12 | Pr | 4-CH$_2$OH | 5-COOH | =CH— | COOH |
| 3-13 | Pr | 4-CH(Me)OH | 5-COOH | =CH— | COOH |
| 3-14 | Pr | 4-C(Me$_2$)OH | 5-COOH | =CH— | COOH |
| 3-15 | Pr | H | 5-COOH | =N— | COOH |
| 3-16 | Pr | 2-Me | 5-COOH | =N— | COOH |
| 3-17 | Pr | 4-Me | 5-COOH | =N— | COOH |
| 3-18 | cPr | H | 5-COOH | =CH— | COOH |
| 3-19 | MEOCH$_2$CH$_2$ | H | 5-COOH | =CH— | COOH |
| 3-20 | Pr | H | 5-COOH | =CH— | Tz |
| 3-21 | Pr | H | 5-CH$_2$COOH | =CH— | COOH |
| 3-22 | Pr | H | 5-CH=CHCOOH | =CH— | COOH |
| 3-23 | Pr | H | 5-COOPom | =CH— | COOH |
| 3-24 | Pr | H | 5-COOMod | =CH— | COOH |
| 3-25 | Pr | H | 5-COOEt | =CH— | Tz |
| 3-26 | Bu | H | 4-COOH | =CH— | COOH |

Of the above compounds, the following are preferred, that is to say Compounds No. 1-1, 1-2, 1-3, 1-4, 1-6, 1-7, 1-8, 1-9, 1-10, 1-11, 1-16, 1-17, 1-18, 1-19, 1-20, 1-21, 1-22, 1-23, 1-24, 1-25, 1-27, 1-28, 1-29, 1-30, 1-31, 1-32, 1-36, 1-37, 1-38, 1-39, 1-40, 1-41, 2-1, 2-2, 2-3, 2-4, 2-8, 2-9, 2-10, 2-12, 2-13, 2-14, 2-15, 2-26, 2-27, 2-28, 2-29, 2-30, 2-31, 2-32, 2-33, 2-34, 2-35, 2-36, 2-37, 2-38, 2-39, 2-40, 2-44, 2-45, 2-46, 2-47, 2-48, 2-49, 2-50, 3-1, 3-2, 3-3, 3-4, 3-5, 3-6, 3-8, 3-11, 3-12, 3-13, 3-14, 3-16, 3-23 and 3-24. More preferred compounds are Compounds No. 1-2, 1-3, 1-6, 1-7, 1-8, 1-9, 1-22, 1-23, 1-24, 1-25, 1-27, 1-28, 1-29, 1-30, 1-31, 1-32, 1-40, 1-41, 2-1, 2-2, 2-3, 2-4, 2-26, 2-27, 2-28, 2-29, 2-30, 2-31, 2-32, 2-33, 2-34, 2-35, 2-40, 2-44, 2-45, 2-46, 2-47, 2-48, 3-1, 3-2, 3-3, 3-4, 3-5 and 3-6.

The most preferred compounds are Compounds No.:

1-2. 4-(1-Hydroxy-1-methylethyl)-1-[(2'-oxalobiphenyl-4-yl)methyl]-2-propylimidazole-5-carboxylic acid;

1-6. 4-(1-Hydroxyethyl)-1-[(2'-oxalobiphenyl-4-yl)-methyl]-2-propylimidazole-5-carboxylic acid;

1-8. 4-Isopropyl-1-[(2'-oxalobiphenyl-4-yl)methyl]-2-propylimidazole-5-carboxylic acid;

1-22. 4-(1-Hydroxy-2-methylpropyl)-1-[(2'-oxalobiphenyl-4-yl)-methyl]-2-propylimidazole-5-carboxamide;

1-24. 4-(1-Hydroxy-2,2-dimethylpropyl)-1-[(2'-oxalobiphenyl-4-yl)methyl]-2-propylimidazole-5-carboxamide;

1-27. Pivaloyloxymethyl 4-(1-hydroxy-1-methylethyl)-1-[(2'-oxalobiphenyl-4-yl)methyl]-2-propylimidazole-5-carboxylate;

1-28. (5-Methyl-2-oxo-1,3-dioxolen-4-yl)methyl 4-(1-hydroxy-1-methylethyl)-1-[(2'-oxalobiphenyl-4-yl)methyl]-2-propylimidazole-5-carboxylate;

1-40. {4'-[4-(1-Hydroxy-1-methylethyl)-2-propyl-5-(tetrazol-5-yl)imidazol-1-ylmethyl]biphenyl-2-yl}glyoxylic acid;

2-1. 2-Ethyl-5,7-dimethyl-3-(2'-oxalobiphenyl-4-yl)methyl-3H-imidazo[4,5-b]pyridine;

2-2. 5,7-Dimethyl-3-(2'-oxalobiphenyl-4-yl)methyl-2-propyl-3H-imidazo[4,5-b]pyridine;

2-26. 2-Ethyl-1-[(2'-oxalobiphenyl-4-yl)methyl]benzimidazole-7-carboxylic acid;

2-28. Pivaloyloxymethyl 2-ethyl-1-[(2'-oxalobiphenyl-4-yl)methyl]benzimidazole-7-carboxylate;

2-30. (5-Methyl-2-oxo-1,3-dioxolen-4-yl)methyl 2-ethyl-1-[(2'-oxalobiphenyl-4-yl)methyl]benzimidazole-7-carboxylate;

2-44. 2-Ethoxy-1-[(2'-oxalobiphenyl-4-yl)methyl]benzimidazole-7-carboxylic acid;

2-45. Pivaloyloxymethyl 2-ethoxy-1-[(2'-oxalobiphenyl-4-yl)methyl]benzimidazole-7-carboxylate;

2-46. (5-Methyl-2-oxo-1,3-dioxolen-4-yl)methyl 2-ethoxy-1-[(2'-oxalobiphenyl-4-yl)methyl]benzimidazole-7-carboxylate;

3-2. 2-{N-[(2'-Oxalobiphenyl-4-yl)methyl]-N-propylamino}nicotinic acid; and 3-5. (N-Propyl-N-{4'-[3-(tetrazol-5-yl)pyrid-2-yl} aminomethyl]biphenyl-2-yl)glyoxylic acid;

and pharmaceutically acceptable salts and esters thereof.

The compounds of the present invention may be prepared by a variety of methods well known for the preparation of compounds of this type. For example, in general terms, they may be prepared by reacting a compound of formula (III):

$$A^x\text{---}H \quad (III)$$

(wherein $A^x$ represents any one of the groups represented by A or such a group in which any reactive group or atom is protected or a precursor to such a group represented by A) with a compound of formula (IV):

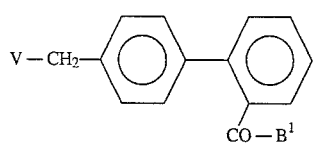

(wherein $B^1$ represents a protected carboxy group or a protected tetrazol-5-yl group and V represents a halogen atom, preferably a chlorine, bromine or iodine atom), and, if necessary, removing any protecting group and/or converting any precursor represented by $A^x$ to a group represented by A, as defined above, and optionally salifying, esterifying or deesterifying the product.

In more detail, the compounds of the present invention may be prepared as illustrated by the following Reaction Schemes A, B and C.

REACTION SCHEME A

In this reaction scheme, a compound of formula (IV) is reacted with a compound of formula (IIIa):

$$A^1\text{---}H \quad (IIIa)$$

(where A, which is defined more fully hereafter, represents a group A in which appropriate groups may be protected), and then, if necessary, protecting groups are removed.

Reaction Scheme A:

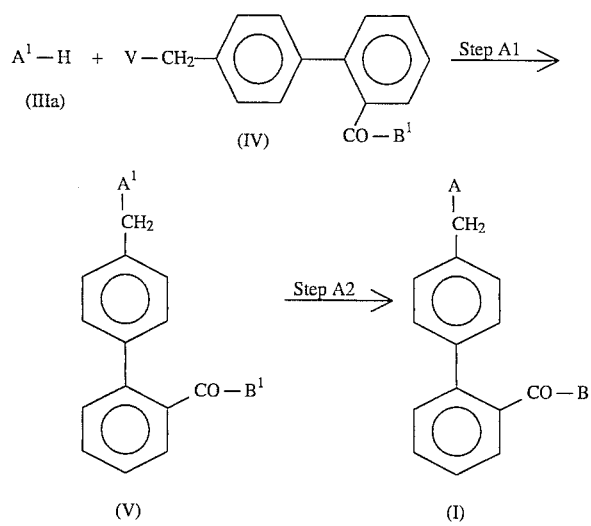

In the above formulae:

A, B, V and $B^1$ are as defined above;

$A^1$ represents a group of formula (XIa), (XIb) or (XIc):

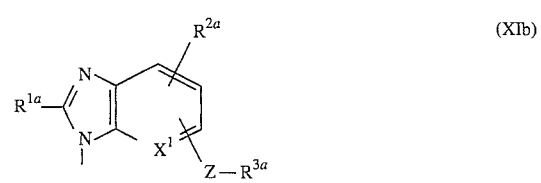

wherein $R^{1a}$, $R^{2a}$, $R^{3a}$ and $X^1$ are as defined above for $R^1$, $R^2$, $R^3$ and X respectively but in which any primary or secondary amino group, any carboxy group or any tetrazol-5-yl group is protected, and Z is as defined above.

There is no particular restriction on the nature of the protecting group used to protect the primary amino group and secondary amino group represented by $R^{1a}$ or $R^{2a}$, and any protecting group commonly used in the art for this purpose may equally be used here. Examples of such protecting groups include: aralkyl groups, such as the benzyl, diphenylmethyl and trityl groups; aliphatic acyl groups, such as the formyl and trifluoroacetyl groups; aralkyloxycarbonyl groups, such as the benzyloxycarbonyl and N-bromobenzyloxycarbonyl groups; and alkoxycarbonyl groups, such as the t-butoxycarbonyl group. Of these, we prefer the benzyl, trityl, trifluoroacetyl, benzyloxycarbonyl and t-butoxycarbonyl groups, more preferably the benzyl, benzyloxycarbonyl and t-butoxycarbonyl groups.

There is likewise no particular restriction on the nature of the protecting group used to protect the tetrazol-5-yl group which may be represented by $R^{3a}$ and $B^1$, and again any group conventionally used for this purpose may be employed. Examples include aralkyl groups, such as the benzyl, diphenylmethyl and trityl (=triphenylmethyl) groups, preferably the trityl group.

The carboxy-protecting groups which may be represented by or included within $R^{3a}$, $X^1$ and $B^1$ may be any of those defined and exemplified above in relation to to $R^3$ and B.

Step A1

In Step A1, a compound of formula (V) is prepared by reacting a compound of formula (IIIa) with a compound of formula (IV).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, especially aromatic hydrocarbons, such as benzene or toluene; ethers, such as tetrahydrofuran or dioxane; alcohols, such as methanol, ethanol or t-butanol; amides, such as dimethylacetamide, dimethylformamide, N-methyl-2-pyrrolidinone or hexamethylphosphoric triamide; ketones, such as acetone or methyl ethyl ketone; nitriles, such as acetonitrile; and sulfoxides, such as dimethyl sulfoxide. A single one of these solvents or a mixture of any two or more of them may be used. Of these, we prefer the ethers, amides, ketones, nitriles and sulfoxides.

The reaction is effected in the presence of a base, the nature of which is not particularly critical to the present invention, provided that it has no adverse effect on the reagents. Examples of suitable bases include: alkali metal carbonates, such as sodium carbonate or potassium carbonate; alkali metal hydrides, such as sodium hydride, potassium hydride or lithium hydride; alkali metal alkoxides, such as sodium methoxide, sodium ethoxide, potassium t-butoxide or lithium methoxide; alkyllithiums, such as methyllithium or butyllithium; lithium amides, such as lithium diethylamide, lithium diisopropylamide or lithium bis(trimethylsilyl)amide; and alkali metal hydrogencarbonates, such as sodium hydrogencarbonate or potassium hydrogencarbonate. Of these, we prefer the alkali metal carbonates, alkali metal hydrides, lithium amides and alkali metal alkoxides.

The reaction can take place over a wide range of temperatures, and the precise reaction temperature is not critical to the invention. In general, we find it convenient to carry out the reaction at a temperature of from −10° C. to 100° C., more preferably from 0° C. to 80° C., depending on the nature of the starting compounds of formulae (IIIa) and (IV), the solvent and the base. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the desired compound of formula (V) can be collected from the reaction mixture by conventional methods. For example, it can be obtained by the following procedure: removing the solvent by evaporation under reduced pressure; adding water to the residue; extracting the residue with a water-immiscible organic solvent, such as ethyl acetate; drying the extract, for example over anhydrous magnesium sulfate; and removing the solvent, for example by evaporation. If necessary, the resulting product can be further purified by conventional methods, such as recrystallization or the various chromatography techniques, notably column chromatography.

Step A2

Step A2 may be carried out if desired, and may include any one or more of the following reactions:

Reaction (a): in which the protecting groups for the carboxy groups included in $R^{3a}$, $X^1$ and $B^1$ are eliminated selectively or non-selectively;

Reaction (b): in which the protecting groups of the tetrazolyl groups included in $R^{3a}$ and $B^1$ are eliminated; and Reaction (c): in which the protecting groups for the primary amino group and secondary amino group included in $R^{1a}$ and $R^{2a}$ are eliminated.

These reactions may be carried out in any appropriate order.

Reaction (a):

The reaction used to eliminate the carboxyprotecting group will vary, depending on the kind of protecting group, and may be carried out by processes well known in synthetic organic chemistry.

For example, where the protecting group is an aralkyl group, such as a benzyl group, the protecting group can be eliminated by catalytic reduction in a suitable solvent and in the presence of a catalytic reduction catalyst (preferably palladium-carbon or platinum oxide) and in the presence of hydrogen, preferably at a pressure of from atmospheric pressure to 5 atmospheres. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; and carboxylic acids, such as acetic acid.

If the carboxy-protecting group is a t-butyl or diphenylmethyl group, it can be eliminated by reaction with an acid (preferably a mineral acid, such as hydrogen chloride or sulfuric acid, or an organic acid, such as trifluoroacetic acid, methanesulfonic acid or N-toluenesulfonic acid) in a suitable solvent, the nature of which is not critical, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; water; or a mixture of water with one or more of the above organic solvents.

Also, where the carboxy-protecting group is an ester residue, it can be eliminated by reaction with a base (preferably an alkali metal hydroxide, such as lithium hydroxide, sodium hydroxide or potassium hydroxide, or an alkali metal carbonate, such as sodium carbonate or potassium carbonate) in a suitable solvent to effect hydrolysis. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; water; or a mixture of water and one or more of the above organic solvents.

The reaction can take place over a wide range of temperatures, and the precise reaction temperature is not critical to the invention, although the preferred reaction temperature and reaction time will vary depending on the method of elimination, the solvent and other factors. In general, we find it convenient to carry out the reaction at a temperature of from 0° C. to 100° C., more preferably from about room temperature to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 20 hours, will usually suffice.

If the deprotection is carried out by a catalytic reaction, the catalyst is preferably filtered off after completion of the reaction, and the solvent is evaporated to obtain the product. On the other hand, if the deprotection is carried out by treatment with an acid, the product can be obtained by collecting the crystals precipitated in the reaction system or by concentrating the reaction mixture. Furthermore, if the deprotection is carried out by alkaline hydrolysis, the product can be obtained by evaporating off the organic solvent, or by neutralizing the resulting system with an acid and collecting the crystals thus precipitated in the aqueous solvent by filtration, or by acidifying the reaction mixture, extracting the product with a water-immiscible organic solvent and evaporating off the solvent. If necessary, the resulting product can be further purified by conventional means, such as recrystallization or the various chromatography techniques, notably column chromatography.

By appropriate choice of reaction conditions and the removal reaction, it is possible to remove the carboxy-protecting groups included in $R^{3a}$, $X^1$ and $B^1$ either selectively or non-selectively.

Reaction (b):

Although the nature of the reaction employed for eliminating the tetrazolyl-protecting group included in $R^{3a}$ and $B^1$ will vary, depending on the kind of protecting group, it may be carried out using methods well known in synthetic organic chemistry.

For example, where the protecting group is a trityl group, deprotection can be achieved by treatment with an acid in a solvent. There is no particular restriction on the nature of the solvent to be employed, provided that it has no adverse effect on the reaction or on the reagents involved and that it can dissolve the reagents, at least to some extent. Examples of suitable solvents include: water; organic acids, such as formic acid or acetic acid; ethers, such as tetrahydrofuran or dioxane; alcohols, such as methanol or ethanol; or a mixture of any two or more of these solvents. Examples of acids which may be employed include: organic carboxylic or sulfonic acids, such as formic acid, acetic acid, oxalic acid, methanesulfonic acid, p-toluenesulfonic acid and trifluoroacetic acid; and inorganic acids, such as hydrochloric acid, hydrobromic acid, sulfuric acid and phosphoric acid. Of these, we prefer acetic acid, trifluoroacetic acid or hydrochloric acid.

The reaction can take place over a wide range of temperatures, and the precise reaction temperature is not critical to the invention. In general, we find it convenient to carry out the reaction at a temperature of from 0° to 120° C., more preferably from 10° to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

Where the protecting group is a benzyl or diphenylmethyl group, it can be eliminated by catalytic reduction employing palladium, platinum oxide, or similar catalyst, as described for the elimination of the protecting group in Reaction (a) in Step A2 of Reaction Scheme A when the carboxy group is protected with an aralkyl group.

After completion of the reaction, the desired compound can be recovered from the reaction mixture by conventional means, for example, in the same manner as in Reaction (a) in Step A2 of Reaction Scheme A.

Reaction (c):

Although the reaction employed for eliminating the protecting groups for primary and secondary amino groups which may be included in $R^{1a}$ and $R^{2a}$ will vary, depending on the nature of the protecting group, it may be carried out using methods well known in synthetic organic chemistry.

For example, where the protecting group is an aralkyl group, such as a benzyl group, or an aralkyloxycarbonyl group, such as a benzyloxycarbonyl group, it can be eliminated by catalytic reduction in a suitable solvent in the presence of a catalytic reduction catalyst (preferably palladium-carbon or platinum oxide) and in the presence of hydrogen, preferably at a pressure of from atmospheric pressure to 5 atmospheres. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; and carboxylic acids, such as acetic acid. This reaction can sometimes be accelerated by adding hydrochloric acid, for example in an amount of from 1 to 5 equivalents per mole of the protected compound.

Where the protecting group is a t-butoxycarbonyl group, it can be eliminated by reaction with an acid (preferably: a mineral acid, such as hydrogen chloride or sulfuric acid; or an organic acid, such as trifluoroacetic acid, methanesulfonic acid, p-toluenesulfonic acid, formic acid or acetic acid) in a suitable solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; halogenated hydrocarbons, such as methylene chloride or chloroform; water; and mixtures of water and one or more of these organic solvents.

Where the protecting group is an aliphatic acyl group, such as a formyl or trifluoroacetyl group, it can be eliminated by reaction with an alkali (preferably an alkali hydroxide, such as sodium hydroxide or potassium hydroxide, or an alkali carbonate, such as sodium carbonate or potassium carbonate) in a suitable solvent to effect hydrolysis. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; water; and mixtures of water and one or more of these organic solvents.

The reaction can take place over a wide range of temperatures, and the precise reaction temperature is not critical to the invention. In general, we find it convenient to carry out the reaction at a temperature of from 0° C. to 100° C., more preferably from about room temperature to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

The desired product may then be recovered from the reaction mixture by conventional means. For example, if the deprotection is carried out by catalytic reduction, the catalyst is preferably filtered off after completion of the reduction, and the solvent is evaporated to obtain the product; whereas if the deprotection is carried out by treatment with an acid, a salt of the desired product can be obtained by collecting the salt precipitated in the reaction system or by concentrating the reaction mixture. Furthermore, if the deprotection is carried out by alkaline hydrolysis, the product can be obtained by collecting the product precipitated in the reaction system or by extracting it with a water-immiscible organic solvent and evaporating the solvent. If necessary, the resulting product can be further purified by conventional means, such as recrystallization or the various chromatography techniques, notably column chromatography.

REACTION SCHEME B

Reaction Scheme B illustrates the preparation of a compound of formula (Ia), which corresponds to a compound of formula (I) wherein $R^3$ represents a carbamoyl group.

Reaction Scheme B:

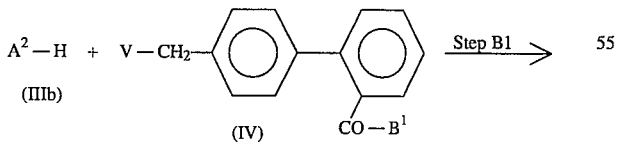

Reaction Scheme B:
-continued

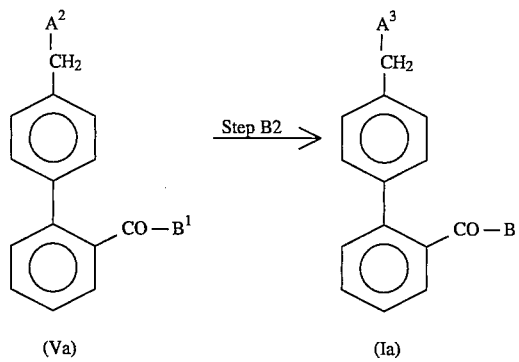

In the above formulae:

V and $B^1$ are as defined above;

$A^2$ represents a group of formula (XIIa), (XIIb) or (XIIc):

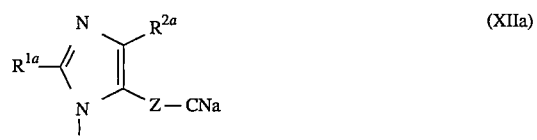

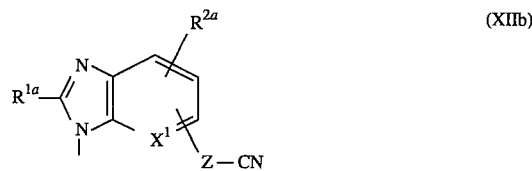

in which $R^{1a}$, $R^{2a}$, $X^1$ and Z are as defined above; and $A^3$ represents a group of formula (XIIIa), (XIIIb) or

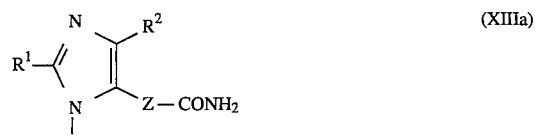

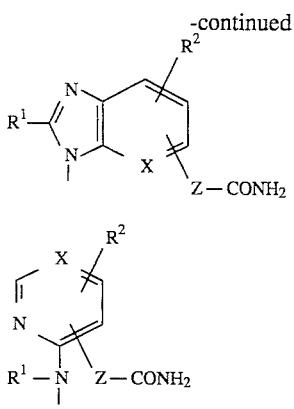

in which $R^1$, $R^2$, X and Z are as defined above

Step B1

In Step B1 a compound of formula (Va) is prepared by reacting a compound of formula (IIIb) with a compound of formula (IV). This step is essentially the same as that described in Step A1 of Reaction Scheme A and may be carried out using the same reagents and reaction conditions.

Step B2

Step B2 is optional, and may include the following reactions:

Reaction (a): in which the cyano group included in $A^2$ is converted into a carbamoyl group;

Reaction (b): in which the protecting group for the carboxy group included in $B^1$ and $X^1$ is eliminated;

Reaction (c): in which the protecting group for the tetrazolyl group included in $B^1$ is eliminated; and Reaction (d): in which the protecting groups for the primary amino group and secondary amino group included in $R^{1a}$ and $R^{2a}$ are eliminated.

These reactions can be carried out in any appropriate order.

Reaction (a):

The conversion of the cyano group into a carbamoyl group in Reaction (a) can be carried out by reacting the compound of formula (Va) with a base.

There is no particular restriction on the nature of the base employed in this reaction provided that it has no adverse effect on the reagents, and any base commonly used in reactions of this type may equally be used here. Examples of suitable bases include: alkali metal hydroxides, such as lithium hydroxide, sodium hydroxide or potassium hydroxide, and alkali metal carbonates, such as sodium carbonate or potassium carbonate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; water; and mixtures of water with any one or more of these organic solvents.

The reaction can take place over a wide range of temperatures, and the precise reaction temperature is not critical to the invention. In general, we find it convenient to carry out the reaction at a temperature of from 0° C. to 100° C., more preferably from about room temperature to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the desired product may be recovered from the reaction mixture by conventional means. For example, in one suitable procedure, the reaction mixture is neutralized and the product thus precipitated can be collected by filtration, or the neutralized reaction mixture may be extracted with a wateroimmiscible organic solvent (such as ethyl acetate), and the solvent is evaporated to obtain the product. If necessary, the resulting product can be further purified by conventional means, such as recrystallization or the various chromatography techniques, notably column chromatography.

Reactions (b), (c) and (d)

Reactions (b), (c) and (d) in this step correspond to Reactions (a), (b) and (c), respectively, in Step A2 of Reaction Scheme A, and may be carried out using the same reagents and reaction conditions.

REACTION SCHEME C

Reaction Scheme C illustrates the preparation of a compound of formula (Ib) which corresponds to a compound of formula (I) wherein A represents a group of formula (IIb).

Reaction Scheme C:

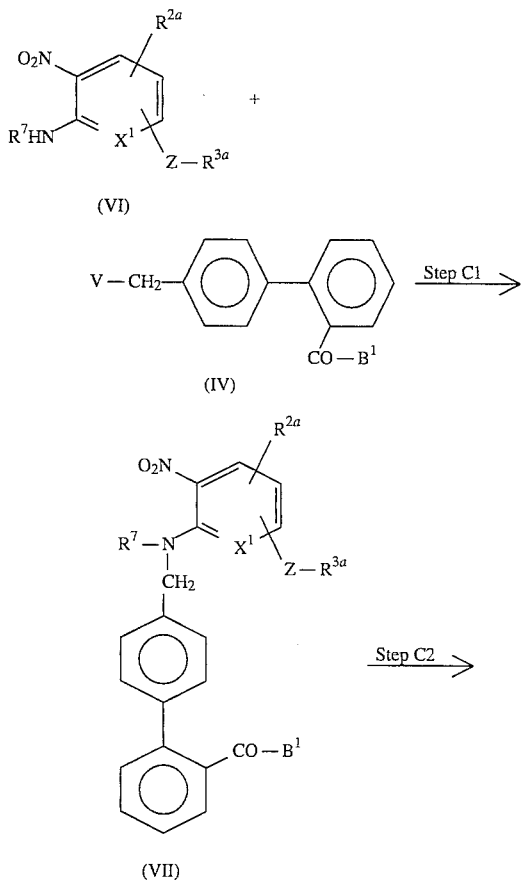

Reaction Scheme C: -continued

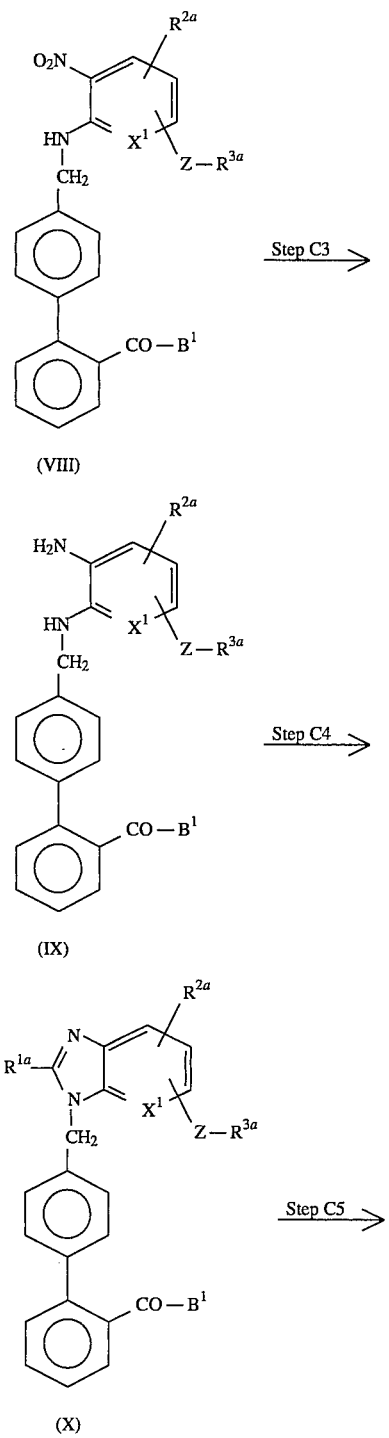

(VIII)

(IX)

(X)

Reaction Scheme C: -continued

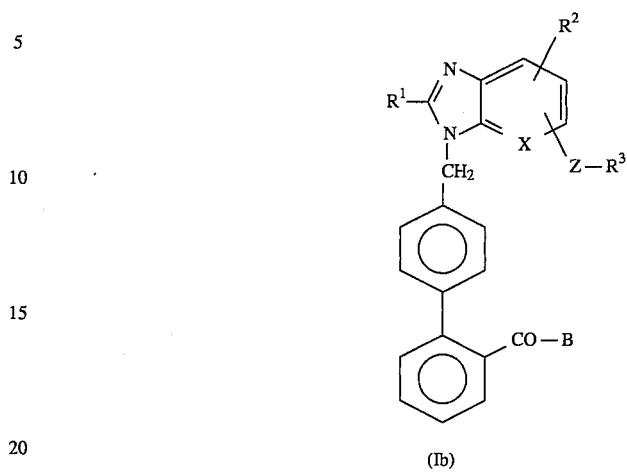

(Ib)

In the above formulae:

$R^1$, $R^2$, $R^3$, $R^{1a}$, $R^{2a}$, $R^{3a}$, X, $X^1$, Z, B, $B^1$ and V are as defined above; and $R^7$ represents a protecting group for an amino group.

The amino-protecting group represented by $R^7$ may be any of those groups defined and exemplified above in relation to $R^{1a}$ and $R^{2a}$.

Step C1

In Step C1 a compound of formula (VII) is prepared by reacting a compound of formula (VI) with the compound of formula (IV). This step is essentially the same as that described in Step A1 of Reaction Scheme A and may be carried out using the same reagents and reaction conditions.

Step C2

In Step C2, the protected amino group of $R^7$ is deprotected, to prepare a compound of formula (VIII). This step can be carried out in the same manner as described in Reaction (c) in Step A2 of Reaction Scheme A. If desired, the amino-protecting group of $R^7$ can be differentiated from the protecting groups for the primary amino group and secondary amino group included in $R^{2a}$ and can be selectively eliminated by suitable choice of the deprotection reaction or the reaction conditions.

Step C3

In Step C3, a compound of formula (IX) is prepared by reducing the nitro group of the compound of formula (VIII). This step can be carried out using methods well known in synthetic organic chemistry.

For example, this may be achieved by catalytic reduction. The reaction is carried out in the presence of a catalytic reduction catalyst, such as platinum, platinum-carbon or Raney nickel and in the presence of hydrogen, preferably under a pressure of from atmospheric pressure to 5 atmospheres. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; esters, such as ethyl acetate or butyl acetate; and carboxylic acids, such as acetic acid, most preferably an alcohol.

The reaction can take place over a wide range of temperatures, and the precise reaction temperature is not critical to the invention. In general, we find it convenient to carry out the reaction at a temperature of from 0° to 60° C., more preferably from 10° C. to 40° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 8 hours, will usually suffice.

After completion of the reaction, the catalyst may be removed by filtration, and the solvent evaporated under reduced pressure, to give the product. If necessary, the resulting product can be further purified by conventional means, such as recrystallization or the various chromatography techniques, notably column chromatography.

When stannous chloride is employed as the reducing agent, the process can be carried out by reacting the nitro compound of formula (VIII) with the reducing agent in an inert solvent (preferably an alcohol, such as methanol and ethanol). The reaction can take place over a wide range of temperatures, and the precise reaction temperature is not critical to the invention. In general, we find it convenient to carry out the reaction at a temperature of from about room temperature to 150° C., more preferably from 50° C. to 100° C. The time required for the reaction may also vary widely, depending on many factors, notably the reaction temperature and the nature of the reagents and solvent employed. However, provided that the reaction is effected under the preferred conditions outlined above, a period of from 1 hour to 24 hours, more preferably from 2 to 8 hours will usually suffice.

After completion of the reaction, the product may be recovered from the reaction mixture by conventional means. For example, in one suitable recovery procedure: the reaction mixture is concentrated; a water-immiscible organic solvent, such as ethyl acetate, and an aqueous alkaline solution, such as an aqueous sodium hydroxide solution, are added to the residue, and the resulting mixture is stirred; the insoluble tin oxide thus formed is removed by filtration; the organic solution is separated; and the solvent is evaporated off under reduced pressure to give the product. If necessary, the product can be further purified by conventional means, such as recrystallization or the various chromatography techniques, notably column chromatography.

It is also possible to carry out the reduction reaction of Step C3 after Step C1, followed by the deprotection reaction of the amino group of Step C2.

Step C4

In Step C4, a compound of formula (X) is prepared by reacting a compound of formula (IX) with a compound of formula (XIV):

$R^{1a}C(OR^8)_3$ (XIV)

wherein $R^{1a}$ is as defined above; and $R^8$ represents an alkyl group having from 1 to 6 carbon atoms, preferably a methyl or ethyl group.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, benzene, toluene and xylene; halogenated hydrocarbons, especially halogenated aliphatic hydrocarbons, such as methylene chloride and 1,2-dichloroethane; ethers, such as tetrahydrofuran and dioxane; and esters, such as ethyl acetate and butyl acetate. Of these, we prefer the hydrocarbons and halogenated hydrocarbons.

The reaction can take place over a wide range of temperatures, and the precise reaction temperature is not critical to the invention. In general, we find it convenient to carry out the reaction at a temperature of from 0° C. to 120° C., more preferably from 20° C. to 100° C., although the preferred reaction temperature will vary, depending on the nature of the starting compounds of formulae (IX) and (XIV), the solvent and the base. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 8 hours, will usually suffice. The reaction can sometimes be accelerated by adding a catalytic amount of an acid, such as hydrogen chloride, p-toluenesulfonic acid or acetic acid.

After completion of the reaction, the desired compound of formula (X) may be collected from the reaction mixture by conventional means. For example, in one suitable recovery procedure: the product precipitated is collected by filtration; or the solvent is evaporated off under reduced pressure, water is added to the residue, and the resulting mixture is extracted with a water-immiscible organic solvent, such as ethyl acetate, after which it is dried, for example over anhydrous mangesium sulfate, and the solvent is removed by evaporation, to give the product. If necessary, the resulting product can be further purified by conventional means, such as recrystallization or the various chromatography techniques, notably column chromatography.

If the compound of formula (XIV) is allowed to be present in the reaction system of Step C3, the reaction of Step C4 may sometimes proceed simultaneously with that of Step C3.

Step C5

Step C5 is optional, and may include the following reactions:

Reaction (a): in which the protecting group for the carboxy group included in $R^{3a}$, $X^1$ and $B^1$ is eliminated, selectively or non-selectively;

Reaction (b): in which the protecting groups for the tetrazolyl group included in $R^{3a}$ and $B^1$ are eliminated; and Reaction (c): in which the protecting groups for the primary amino group and secondary amino group included in $R^{1a}$ and $R^{2a}$ are eliminated.

These reactions can be carried in the same manner as the corresponding reactions in Step A2.

The starting compounds of formulae (III), (IIIa) and (VI)

used in Reaction Schemes A to C are known per se or can be prepared by a known process [e.g. as shown in European Publications No. 503785 and No. 459136, J. Med. Chem., 34, 2525 (1991), ibid 34, p.2919 (1991), and ibid 35, p.3714 (1992)]. The starting compound of formula (IV) can be prepared, for example, as shown in the following Reaction Scheme D or Reaction Scheme E.

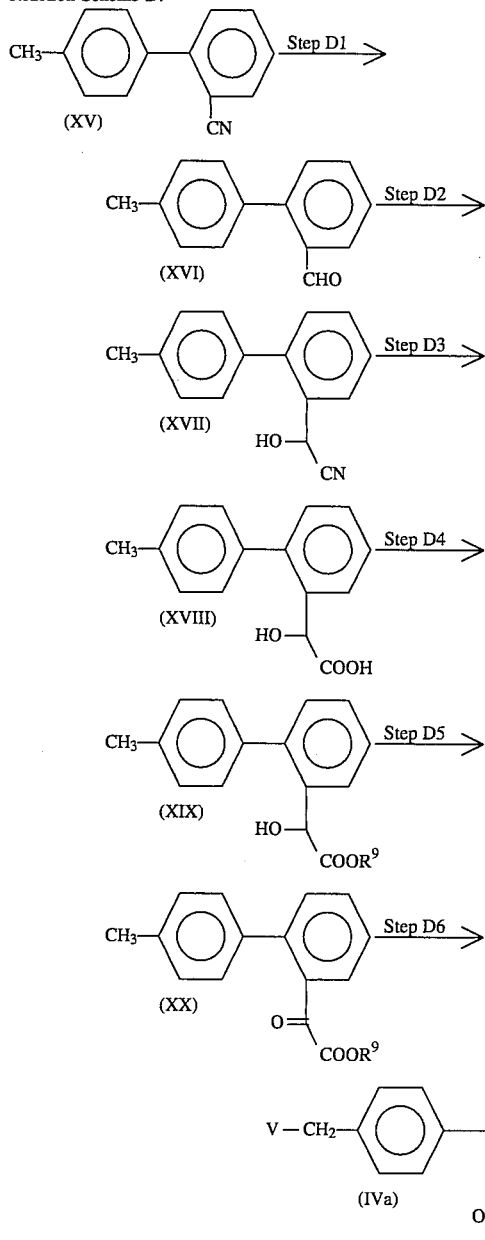

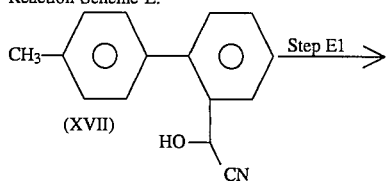

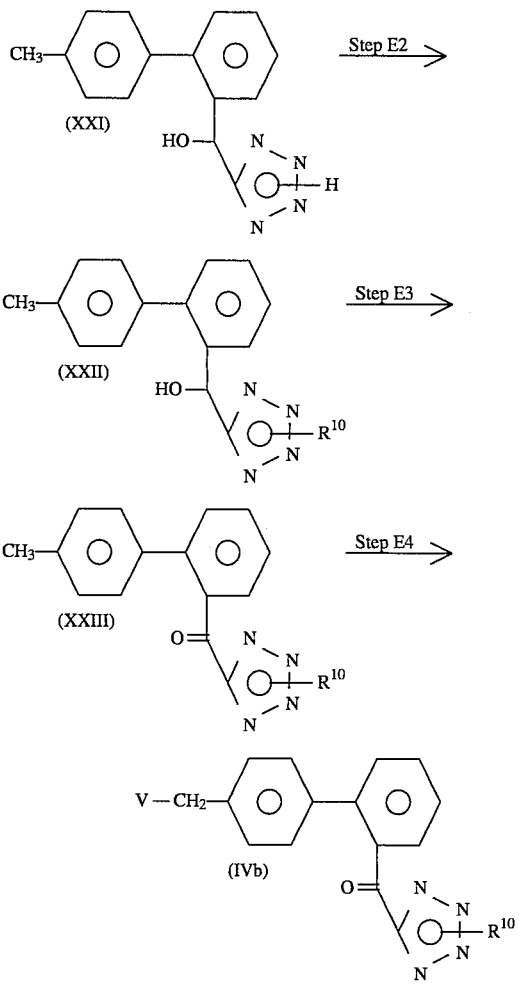

In the above schemes, V is as defined above; $R^9$ represents a carboxy-protecting group; and $R^{10}$ represents a protecting group for the tetrazolyl group. The protecting group for the carboxy group, $R^9$ includes those described for $R^{3a}$ and $B^1$, and the protecting group for the tetrazolyl group, $R^{10}$ includes those described for $R^{3a}$ and $B^1$.

REACTION SCHEME D

Reaction Scheme D illustrates the preparation of a compound of formula (IVa), which corresponds to the compound of formula (IV) wherein $B^1$ represents a protected carboxy group.

Step D1

In Step D1, a compound of formula (XVI) is prepared by reacting a compound of formula (XV) with a suitable amount, preferably from 1 to 3 equivalents, more preferably from 1.5 to 2 equivalent amounts, of a reducing agent (for example: a metal hydride, such as diisobutyl aluminum hydride or lithium triethoxyaluminum hydride; Raney nickel-formic acid; or stannous chloride, preferably diisobutyl aluminum hydride) in an inert solvent (preferably an aromatic hydrocarbon, such as benzene, toluene and xylene, or an ether, such as tetrahydrofuran and dioxane).

The reaction can take place over a wide range of temperatures, and the precise reaction temperature is not critical to the invention. In general, we find it convenient to carry out the reaction at a temperature of from −80° C. to 60° C., more preferably from −30° C. to about room temperature. The time required for the reaction may also vary widely, depending on many factors, notably the reaction temperature and the nature of the reagents and solvent employed. However, provided that the reaction is effected under the preferred conditions outlined above, a period of from 10 minutes to 8 hours, more preferably from 30 minutes to 4 hours, will usually suffice.

At the end of the reaction, any excess of reducing agent is, if necessary, decomposed by adding an alcohol, and dilute hydrochloric acid and a water-immiscible organic solvent (such as ethyl acetate) are added to the reaction mixture, the mixture is stirred, the organic solution is separated, and the solvent is removed by evaporation to obtain the reaction product. If necessary, the resulting product can be further purified by conventional means, such as recrystallization or the various chromatography techniques, notably column chromatography.

Step D2

In Step D2, a compound of formula (XVII) is prepared by reacting the compound of formula (XVI) with a cyano compound (preferably an alkali metal cyanide, such as sodium cyanide or potassium cyanide, or a trialkylsilyl cyanide in which the alkyl parts have from 1 to 6 carbon atoms, such as trimethylsilyl cyanide) in an inert solvent. When the trialkylsilyl cyanide is employed, the O-trialkylsilyl derivative thus obtained is then treated with an acid.

When an alkali metal cyanide is employed, it is preferably used in an amount of from 1 to 3 equivalents, more preferably from 1.2 to 2 equivalents per mole of the compound of formula (XVI). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; halogenated hydrocarbons, especially halogenated alipphatic hydrocarbons, such as methylene chloride or chloroform; alcohols, such as methanol or ethanol; water; or a mixture of water and one or more of these organic solvents. The reaction can take place over a wide range of temperatures, and the precise reaction temperature is not critical to the invention. In general, we find it convenient to carry out the reaction at a temperature of from −10° C. to 80° C., more preferably from 0° C. to 30° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 2 to 16 hours, will usually suffice. This reaction can, if desired, be accelerated by adding sodium hydrogen sulfite. After completion of the reaction, the product can be recovered by conventional means, for example by extracting the reaction mixture with a water-immiscible organic solvent (such as ethyl acetate) and evaporating the solvent from the extract. If necessary, the resulting product can be further purified by conventional means, such as recrystallization or the various chromatography techniques, notably column chromatography.

If a trialkylsilyl cyanide is employed, it is preferably used in an amount of from 1 to 2 equivalents, more preferably from 1.05 to 1.2 equivalents, per mole of the compound of formula (XVI), and the reaction is preferably carried out in the presence of a catalytic amount of zinc iodide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; and halogenated hydrocarbons, especially halogenated aliphatic hydrocarbons, such as methylene chloride and chloroform. The reaction can take place over a wide range of temperatures, and the precise reaction temperature is not critical to the invention. In general, we find it convenient to carry out the reaction at a temperature of from −10° C. to 80° C., more preferably from 10° C. to 40° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice. After completion of the reaction, the desired product of formula (XVII), in the form of its O-trialkylsilyl derivative, can be obtained by concentrating the reaction mixture, extracting the concentrate with a water-immiscible organic solvent, washing the extract with a weakly alkaline aqueous solution, such as aqueous sodium hydrogencarbonate, and evaporating off the solvent. If necessary, the resulting product can be further purified by conventional means, such as recrystallization or the various chromatography techniques, notably column chromatography.

The O-trialkylsilyl group is then removed. This reaction can be carried out by treatment with a catalytic amount of an acid (for example p-toluenesulfonic acid, methanesulfonic acid or hydrochloric acid) in a suitable solvent, the nature of which is not critical, provided that it has no adverse effect on the reaction or on the reagents involved and that it can dissolve the reagents, at least to some extent. Examples of suitable solvents include alcohols, such as methanol or ethanol. The reaction can take place over a wide range of temperatures, and the precise reaction temperature is not critical to the invention. In general, we find it convenient to carry out the reaction at a temperature of from −20° C. to 60° C., more preferably around room temperature. The time required for the reaction may also vary widely, depending on many factors, notably the reaction temperature and the nature of the reagents and solvent employed. However, provided that the reaction is effected under the preferred conditions outlined above, a period of from 10 minutes to 5 hours, more preferably from 30 minutes to 2 hours, will usually suffice.

After completion of the reaction, the product can be recovered from the reaction mixture by conventional means, for example: by concentrating the reaction mixture, extracting the concentrate with a water-immiscible organic solvent, such as ethyl acetate, washing with a weakly alkaline aqueous solution, such as aqueous sodium hydrogencarbonate, and evaporating off the solvent. If necessary, the resulting product can be further purified by conventional means, such as recrystallization or the various chromatography techniques, notably column chromatography.

However, if desired, the O-trialkylsilyl derivative can also be employed as the starting material in Step D3.

Step D3

In Step D3, a compound of formula (XVIII) is prepared by treating the compound of formula (XVII) or the O-trialkylsilyl derivative of the compound of formula (XVII) with an acid (preferably concentrated sulfuric acid or concentrated hydrochloric acid) in a suitable solvent, the nature of which is not critical, provided that it has no adverse effect on the reaction or on the reagents involved and that it can dissolve the reagents, at least to some extent. Examples of suitable solvents include: fatty acids, such as acetic acid or propionic acid; ethers, such as dioxane; and water.

The reaction can take place over a wide range of temperatures, and the precise reaction temperature is not critical to the invention. In general, we find it convenient to carry out the reaction at a temperature of from 50° C. to 120° C., more preferably from 80° C. to 100° C. The time required for the reaction may also vary widely, depending on many factors, notably the reaction temperature and the nature of the reagents and solvent employed. However, provided that the reaction is effected under the preferred conditions outlined above, a period of from 8 hours to 3 days, more preferably from 16 to 40 hours, will usually suffice.

The reaction product can be recovered from the reaction mixture by conventional means, for example: by concentrating the reaction mixture, extracting the concentrate with an aqueous alkaline solution, such as aqueous sodium hydroxide, acidifying the aqueous extract with an acid, such as hydrochloric acid, extracting the mixture with a water-immiscible organic solvent, such as ethyl acetate, and evaporating off the solvent. If necessary, the resulting product can be further purified by conventional means, such as recrystallization or the various chromatography techniques, notably column chromatography.

Step D4

In Step D4, a compound of formula (XIX) is prepared by esterifying the compound of formula (XVIII). This reaction may be carried out using techniques well known in the art of synthetic organic chemistry.

For example, the esterification can be carried out by reacting the carboxylic acid of formula (XVIII) with a compound of formula (XXIV):

$$R^9-W \qquad\qquad (XXIV)$$

wherein $R^9$ is as defined above; and W represents a halogen atom, such as chlorine atom, bromine atom or iodine atom, or a group of formula $-OSO_3R^9$ (in which $R^9$ is as defined above). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as dimethylformamide or dimethylacetamide; halogenated hydrocarbons, such as methylene chloride; ketones, such as acetone or methyl ethyl ketone; and nitriles, such as acetonitrile. Of these, we prefer the amides or the ketones. The reaction is effected in the presence of a base, for example: an alkali metal carbonate, such as sodium carbonate or potassium carbonate; an alkali metal hydrogencarbonate, such as sodium hydrogencarbonate or potassium hydrogencarbonate; an alkali metal hydride, such as lithium hydride, sodium hydride or potassium hydride; or a tertiary amine, such as triethyamine, N-methylmorpholine or diisopropylethylamine. Of these, the metal carbonates or the tertiary amines are preferred.

The same reaction conditions, including reaction temperature and reaction time, and the method of recovering the reaction product as those used in Step A1 of Reaction Scheme A can be employed.

Where the ester residue is an alkyl group having from 1 to 6 carbon atoms, the carboxylic acid of formula (XVIII) can be reacted in an alcohol having from 1 to 6 carbon atoms, such as methanol, ethanol, propanol or hexanol, in the presence of an acid catalyst, such as hydrogen chloride or sulfuric acid, at a suitable temperature, for example from 0° C. to 100° C., for a suitable period, for example from 1 to 24 hours. The desired compound can, for example, be recovered in the same manner as in Step A1 of Reaction Scheme A.

Step D5

In Step D5, a compound of formula (XX) is prepared by reacting the compound of formula (XIX) with an oxidizing agent [preferably a metal oxide, such as manganese dioxide or silver oxide; a mixture of a pyridine-sulfur trioxide complex and dimethyl sulfoxide; an acid anhydride (such as trifluoroacetic anhydride or oxalyl chloride-dimethyl sulfoxide) or an acyl chloride-dimethyl sulfoxide] in a suitable solvent, the nature of which is not critical, provided that it has no adverse effect on the reaction or on the reagents involved and that it can dissolve the reagents, at least to some extent.

When a metal oxide is employed, the solvent employed is preferably a halogenated hydrocarbon, such as methylene chloride or chloroform; a hydrocarbon, such as hexane, benzene, toluene or xylene; an ether, such as diethyl ether, tetrahydrofuran or dioxane; an ester, such as ethyl acetate or butyl acetate; or a ketone, such as acetone or methyl ethyl ketone. The reaction temperature is preferably from 0° C. to 100° C., more preferably from 10° C. to 60° C., and the reaction time is preferably from 30 minutes to 24 hours, more preferably from 1 to 20 hours. After completion of the reaction, the insolubles are filtered off, and the solvent is evaporated to give the product. If necessary, the resulting product can be further purified by conventional means, such as recrystallization or the various chromatography techniques, notably column chromatography.

When a mixture of a pyridine-sulfur trioxide complex and dimethyl sulfoxide, an acid anhydride-dimethyl sulfoxide or an acyl chloride-dimethyl sulfoxide is employed, the reaction is preferably carried out in the presence of a base (preferably an organic amine, such as triethylamine or N-methylmorpholine). The reaction is also normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride or chloroform; hydrocarbons, such as hexane, benzene, toluene or xylene; ethers, such as diethyl ether, tetrahydrofuran or dioxane; esters, such as ethyl acetate or butyl acetate; and ketones, such as acetone or methyl ethyl ketone. The reaction can take place over a Wide range of temperatures, and the precise reaction temperature is not critical to the invention. In general, we find it convenient to carry out the reaction at a temperature of from −70° C. to 60° C., more preferably from −50° C. to 30° C. The time required for the reaction may also vary widely, depending on many factors, notably the reaction temperature and the nature of the reagents and solvent employed. However, provided that the reaction is effected under the preferred conditions outlined above, a period of from 30 minutes to 16 hours, more preferably from 1 to 8 hours, will usually suffice. After completion of the reaction, the product can be recovered by concentrating the reaction mixture, extracting the concentrate with a water-immiscible organic solvent, such as ethyl acetate, washing the extract with water and evaporating off the solvent. If necessary, the resulting product can be further purified by conventional means, such as recrystallization or the various chromatography techniques, notably column chromatography.

If the protecting group $R^9$ for the carboxylic acid is to be replaced, the protecting group of the compound of formula (XX) can be eliminated according to the method of Reaction (a) in Step A2 of Reaction Scheme A, and then the compound of formula (IX) may be reprotected according to the method of Step D4 of Reaction Scheme D or in the following manner.

The carboxylic acid obtained by carrying out Reaction (a) in Step A2 of Reaction Scheme A is treated with a halogenating agent (for example phosphorus pentachloride, thionyl chloride or oxalyl chloride) in an inert solvent (preferably a halogenated hydrocarbon, such as methylene chloride or chloroform, an ether, such as tetrahydrofuran or dioxane, or an aromatic hydrocarbon, such as benzene or toluene) at a suitable temperature, for example from −10° C. to 100° C., more preferably from 0° C. to 80° C., for a suitable period, for example from 30 minutes to 5 hours, to give the corresponding acyl halide. The acyl halide is then reacted with the corresponding alcohol compound (for example, desirably potassium t-butoxide, when a t-butyl ester is to be prepared) in the presence of a base (for example an organic amine, such as triethylamine) at a suitable temperature, for example around room temperature, for a suitable period, for example from 30 minutes for 10 hours. The desired compound can then be recovered by conventional means, for example in the same manner as in Step A1 of Reaction Scheme A.

Step D6

In Step D6, a compound of formula (IVa) is prepared by reacting the compound of formula (XX) with a halogenating agent (preferably N-chlorosuccinimide, N-bromosuccinimide or 1,3-dibromo-5,5-dimethylhydantoin) in an inert solvent (preferably a halogenated hydrocarbon, such as methylene chloride, 1,2-dichloroethane or carbon tetrachloride) in the presence of a catalyst (preferably benzoyl peroxide or azobisisobutyronitrile).

The reaction can take place over a wide range of temperatures, and the precise reaction temperature is not critical to the invention. In general, we find it convenient to carry out the reaction at a temperature of from 0° C. to 100° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 16 hours, will usually suffice. This reaction can sometimes be accelerated by irradiation, for example with a tungsten lamp.

After completion of the reaction, the reaction mixture is preferably washed with water and dried, for example, over anhydrous magnesium sulfate, after which the solvent is removed by evaporation to give the desired product. If necessary, the resulting product can be further purified by conventional means, such as recrystallization or the various chromatography techniques, notably column chromatography.

REACTION SCHEME E

Reaction Scheme E illustrates the preparation of a compound of formula (IVb), which corresponds to the compound of formula (IV) wherein $B^1$ represents a protected tetrazolyl group.

Step E1

In Step E1, a compound of formula (XXI) is prepared by converting the cyano group contained in the compound of formula (XVII) to a tetrazolyl group. This step can be carried out using any of the following three reactions.

Reaction (a): Reaction with an alkali metal azide

This reaction is carried out by reacting the corresponding cyano compound of formula (XVII) with a suitable amount, for example from 1 to 5 equivalents, more preferably from 1 to 3 equivalents, of an alkali metal azide, such as lithium azide, sodium azide or potassium azide, preferably sodium azide, in the presence of an ammonium halide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as dioxane or 1,2-dimethoxyethane; alcohols, such as methanol or ethanol; amides, such as dimethylformamide or dimethylacetamide; and sulfoxides, such as dimethyl sulfoxide. The amount of ammonium halide is preferably from 0.5 to 2 equivalents, more preferably from 1 to 1.2 equivalents, per mole of the compound of formula (XVII). Examples of suitable ammonium halides include ammonium fluoride, ammonium chloride and ammonium bromide, preferably ammonium chloride.

The reaction can take place over a wide range of temperatures, and the precise reaction temperature is not critical to the invention. In general, we find it convenient to carry out the reaction at a temperature of from 70° C. to 150° C., more preferably from 90° C. to 120° C. The time required for the reaction may also vary widely, depending on many factors, notably the reaction temperature and the nature of the reagents and solvent employed. However, provided that the reaction is effected under the preferred conditions outlined above, a period of from 10 hours to 7 days, more preferably from 1 to 5 days will usually suffice.

After completion of the reaction, the product may be recovered from the reaction mixture by conventional means. For example, water and a water-immiscible organic solvent, such as ethyl acetate, are added to the reaction mixture, and the organic solvent layer is separated, after which the solvent is evaporated off, to give the product. If necessary, the resulting product can be further purified by conventional means, such as recrystallization or the various chromatography techniques, notably column chromatography.

Reaction (b): Reaction with a trialkyl or triaryltin azide

This reaction is carried out by reacting the cyano compound of formula (XVII) with a suitable amount, for example from 1 to 3 equivalents, more preferably from 1 to 2 equivalents, of a trialkyltin azide or a triaryltin azide. Examples of trialkyltin azides include those in which each alkyl group has from 1 to 6 carbon atoms, such as trimethyltin azide, triethyltin azide or tributyltin azide. Examples of triaryltin azides include triphenyltin azide and tritolyltin azide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene or heptane; halogenated hydrocarbons, such as dichloroethane or chloroform; ethers, such as dioxane or 1,2-dimethoxyethane; esters, such as ethyl acetate or butyl acetate; amides, such as dimethylformamide or dimethylacetamide; and sulfoxides, such as dimethyl sulfoxide. The resulting tin adduct is then treated with an acid (preferably hydrochloric acid or sulfuric acid), a base (preferably an alkali metal hydroxide, such as sodium hydroxide or potassium hydroxide, an alkali metal carbonate, such as sodium carbonate or potassium carbonate, or an alkali metal hydrogencarbonate, such as sodium hydrogencarbonate or potassium hydrogencarbonate) or an alkali metal fluoride (preferably sodium fluoride or potassium fluoride). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: those solvents described above; alcohols, such as methanol or ethanol; water; and aqueous alcohols.

The reaction can take place over a wide range of temperatures, and the precise reaction temperature is not critical to the invention. In general, we find it convenient to carry out the reaction with the tin compound at a temperature of from 60° C. to 150° C., more preferably from 80° C. to 120° C., and the treatment with the acid, base or fluoride at around room temperature. The time required for the reaction may also vary widely, depending on many factors, notably the reaction temperature and the nature of the reagents and solvent employed. However, provided that the reaction is effected under the preferred conditions outlined above, a period of from 8 hours to 7 days, more preferably from 1 to 5 days will usually suffice for the reaction with the tin compound, whilst the treatment with the acid, base or fluoride will normally require from 30 minutes to 24 hours, more preferably from 1 to 6 hours.

After completion of the reaction, the product may be recovered from the reaction mixture by conventional means. For example, water and a water-immiscible organic solvent, such as ethyl acetate, are added to the reaction mixture, and the organic solvent layer is separated, after which the solvent is evaporated off, to give the product. If necessary, the resulting product can be further purified by conventional means, such as recrystallization or the various chromatography techniques, notably column chromatography.

Reaction (c): Reaction with a trialkyl or triaryltin halide and an alkali metal azide This reaction is carried out in the same manner as in Reaction (b), except that a suitable amount, for example from 1 to 3 equivalents, more preferably from 1 to 2 equivalents, of a trialkyl or triaryltin halide ( for example trimethyltin chloride, triethyltin chloride, tributyltin chloride or triphenyltin chloride) and a suitable amount, for example from 1 to 3 equivalents, more preferably from 1 to 2 equivalents, of an alkali metal azide (preferably sodium azide or potassium azide) are used in place of the trialkyl or triaryltin azide.

Step E2

In Step E2, a compound of formula (XXII) is prepared by protecting the tetrazolyl group contained in the compound of formula (XXI). This step is carried out by reacting the compound of formula (XXI) with a compound of formula (XXV):

$$R^{10}-W \tag{XXV}$$

wherein $R^{10}$ and W are as defined above. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as dimethylformamide or dimethylacetamide; halogenated hydrocarbons, such as methylene chloride or 1,2-dichloroethane; ketones, such as acetone or methyl ethyl ketone; and nitriles, such as acetonitrile. Of these, we prefer the amides and the ketones. The reaction is effected in the presence of a base, for example: an alkali metal carbonate, such as sodium carbonate or potassium carbonate; an alkali metal hydrogencarbonate, such as sodium hydrogencarbonate or potassium hydrogencarbonate; an alkali metal hydride, such as lithium hydride, sodium hydride or potassium hydride; pyridine or a derivative thereof, such as pyridine or 1,6-lutidine; or a tertiary amine, such as triethylamine, N-methylmorpholine or diisopropylethylamine. Of these, we prefer to use a metal carbonate, pyridine or a derivative thereof (which, if employed in great excess, can serve also as the reaction solvent) or a tertiary amine.

The same reaction conditions, including reaction temperature and reaction time, and the method of recovering the reaction product as those used in Step A1 of Reaction Scheme A can be employed.

Step E3

In Step E3, a compound of formula (XXIII) is prepared by oxidizing the compound of formula (XXII). This step involves essentially the same reaction as that in Step D5 of Reaction Scheme D and may be carried out using the same reagents and reaction conditions. The product of the reaction may then be recovered as described in that Step.

Step E4

In Step E4, a compound of formula (IVb) is prepared by halogenating the compound of formula (XXIII). This step involves essentially the same reaction as that in Step D6 of Reaction Scheme D and may be carried out using the same reagents and reaction conditions. The product of the reaction may then be recovered as described in that Step.

BIOLOGICAL ACTIVITY

The compounds of the present invention exhibit an excellent inhibitory effect against the elevation of blood pressure induced by angiotensin II and are therefore extremely useful for prevention or treatment of circulatory diseases as a hypotensive drug or a therapeutic drug for cardiovascular diseases.

Their biological activity was determined by the following experiment.

Evaluation of AII receptor blocking activity by Inhibition of pressor response to angiotensin II The biological activity of each compound was assessed by determining the dose required to inhibit the pressor response to intravenous angiotensin II by fifty percent ($ID_{50}$) in rats. Male Wister-Imamichi rats, each weighing 300 to 400 g, were anesthesized by intraperitoneal injection of 100 mg/Kg of sodium thiobutabarbital [Inactin (trade name)] and two cannulae were inserted: one into the femoral artery for measuring blood pressure and the other into the femoral vein for injecting drugs. Fifty ng/kg of angiotension II were administered intravenously at intervals of about 10 minutes, and the elevation of blood pressure (normally about 50 mmHg) was observed. After constant pressor responses to angiotensin II had been obtained, a test compound was administered intravenously. Two minutes later, angiotension II was again injected, and the inhibitory effect of the test compound was estimated. The percent inhibitions of the pressor response to angiotensin II by progressive increase of the test compound was used to calculate the value of $ID_{50}$. Angiotensin II was used in this test dissolved in 0.5% bovine serum albumin (BSA) and the test compounds were dissolved in 100% dimethyl sulfoxide (DMSO). Table 4 shows the $ID_{50}$ values thus determined.

The compounds of the invention are identified hereafter by the number of the one of the following Examples which illustrates their preparation.

TABLE 4

| Test compound (Compound of Example No.) | ID50 (mg/kg, i.v.) |
| --- | --- |
| 1 | 0.0065 |
| 2 | 0.026 |
| 6 | 0.020 |
| 7 | 0.021 |
| 8 | 0.060 |
| 9 | 0.053 |
| 10 | 0.022 |
| 11 | 0.017 |
| 12 | 0.042 |
| 13 | 0.048 |
| 14 | 0.0096 |
| 16 | 0.024 |
| 20 | 0.026 |

The compounds of the present invention can be administered by themselves or in the form of a conventional pharmaceutical preparation, whose form will, of course, depend on the chosen route of administration. For example, for oral administration, they may be formulated as tablets, capsules, granules, powders, syrups or the like, or, for parenteral administration, they may be formulated as injections, suppositories or the like. These pharmaceutical preparations can be produced in the conventional manner using the adjuvants generally known in the art, such as excipients, binders, disintegrating agents, lubricants, stabilizers, corrigents and the like. Although the dosage may vary depending upon the symptoms and age of the patient, the nature and severity of the disease or disorder and the route and manner of administration, in the case of oral administration to an adult human patient, the compounds of the present invention may normally be administered at a total daily dose of from 1 to 1000 mg, preferably from 5 to 300 mg, either in a single dose, or in divided doses, for example one to three times a day; in the case of intravenous injection, a dose of from 0.1 to 100 mg, preferably from 0.5 to 30 mg, may be administered from one to three times a day.

The invention is further illustrated by the following Examples, which demonstrate the preparation of various of the compounds of the invention. The preparation of certain starting materials used in these Examples is shown in the subsequent Preparations. In the formulae accompanying these Examples and Preparations, certain abbreviations are used, which are as defined above in relation to Tables 1 to 3.

EXAMPLE 1

4-(1-Hydroxy-1-methylethyl)-1-[(2'-oxalobiphenyl-4-yl)methyl]-2-propylimidazole-5-carboxylic acid (Compound No. 1-2)

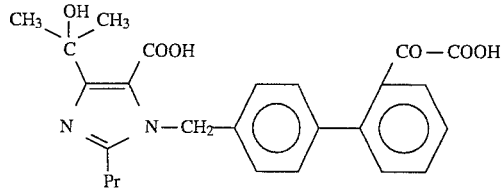

1(a) Ethyl 4-(1-hydroxy-1-methylethyl)-1-[(2'-methoxalylbiphenyl-4-yl)methyl]-2-propylimidazole-5-carboxylate 140 mg of potassium t-butoxide were added, whilst ice-cooling, to a solution of 288 g of ethyl 4-(1-hydroxy-1-methylethyl)-2-propylimidazole-5-carboxylate dissolved in 3 ml of dimethylacetamide, and the resulting mixture was stirred for 5 minutes. A solution of 433 mg of methyl (4'-bromomethylbiphenyl-2-yl)glyoxylate (prepared as described in Preparation 8) dissolved in 5 ml of dimethylacetamide was then added to the mixture, which was then stirred at room temperature for 4 hours. At the end of this time, ethyl acetate and water were added to the reaction mixture, and the organic solvent layer was separated and dried over anhydrous sodium sulfate. The solvent was then removed by distillation under reduced pressure. The resulting residue was subjected to column chromatography through silica gel, using a 1:1 by volume mixture of ethyl acetate and hexane as the eluent, to give 447 mg of the title compound, as a syrup.

Nuclear Magnetic Resonance Spectrum ($CDCl_3$, 270 MHz), δ ppm: 0.98 (3H, triplet, J=7.5 Hz); 1.26 (3H, triplet, J=7 Hz); 1.64 (6H, singlet); 1.75 (2H, sextet, J=7.5 Hz); 2.65 (2H, triplet, J=7.5 Hz); 3.31 (3H, singlet); 4.27 (2H, quartet, J=7 Hz); 5.51 (2H, singlet); 5.68 (1H, singlet); 6.99 (2H, doublet, J=8.5 Hz); 7.27 (2H, doublet, J=8.5 Hz); 7.42 (1H, doublet, J=7 Hz); 7.51 (1H, triplet, J=7 Hz); 7.65 (1H, triplet, J=7 Hz); 7.81 (1H, doublet, J=7 Hz).

1(b) 4-(1-Hydroxy-1-methylethyl)-1-[(2'-oxalobiphenyl 4-yl)methyl]-2-propylimidazole-5-carboxylic acid A solution of 247 mg of lithium hydroxide monohydrate dissolved in 3 ml of water was added to a solution of 447 mg of ethyl 4-(1-hydroxy-1-methylethyl)-1-[(2'-methoxalylbiphenyl-4-yl)methyl]-2-propylimidazole-5-carboxylate [prepared as described in step (a) above] dissolved in 5 ml of dioxane, and the resulting mixture was stirred at room temperature for 5 hours. At the end of this time, the dioxane in the reaction mixture was removed by evaporation under reduced pressure, and 5.9 ml of 1N aqueous hydrochloric acid were added to the residue. The crystals thus precipitated were collected by filtration and dried in air, to give 310 mg of the title compound, softening at 163° C. and melting at 183°–185° C.

Nuclear Magnetic Resonance Spectrum (hexadeuterated dimethyl sulfoxide, 270 MHz), δ ppm: 0.88 (3H, triplet, J=7.5 Hz); 1.56 (6H, singlet); 1.59 (2H, sextet, J=7.5 Hz); 2.61 (2H, triplet, J=7.5 Hz); 5.71 (2H, singlet); 7.07 (2H, doublet, J=8 Hz); 7.25 (2H, doublet, J=8 Hz); 7.46 (1H, doublet, J=7 Hz); 7.54 (1H, triplet, J=7 Hz); 7.66–7.72 (2H, multipier).

EXAMPLE 2

2-Butyl-4-(1-hydroxy-1-methylethyl)-1-[(2'-oxalobiphenyl-4-yl)methyl]imidazole-5-carboxylic acid (Compound No. 1-3)

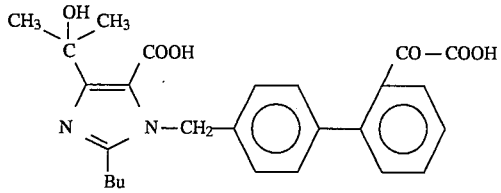

2(a) Ethyl 2-butyl-4-(1-hydroxy-1-methylethyl)-1-[(2'-methoxalylbiphenyl- 4-yl)methyl]imidazole-5-carboxylate Following a procedure similar to that described in Example 1(a), but using 509 mg of ethyl 2-butyl-4-(1-hydroxy-1-methylethyl)imidazole-5-carboxylate, 247 mg of potassium t-butoxide and 733 mg of methyl (4'-bromomethylbiphenyl- 2-yl)glyoxylate (prepared as described in Preparation 8), 878 mg of the title compound were obtained as a syrup.

Nuclear Magnetic Resonance Spectrum (CDCl$_3$, 270 MHz), δ ppm: 0.91 (3H, triplet, J=7.5 Hz); 1.27 (3H, triplet, J=7 Hz); 1.39 (2H, sextet, J=7.5 Hz); 1.64 (6H, singlet); 1.62–1.75 (2H, multipier); 2.67 (2H, triplet, J=7.5 Hz); 3.31 (3H, singlet); 4.27 (2H, quartet, J=7 Hz); 5.51 (2H, singlet); 5.69 (1H, singlet); 6.99 (2H, doublet, J=8 Hz); 7.27 (2H, doublet, J=8 Hz); 7.42 (1H, doublet, J=7 Hz); 7.51 (1H, triplet, J=7 Hz); 7.65 (1H, triplet, J=7 Hz); 7.81 (1H, doublet, J=7 Hz).

2(b) 2-Butyl-4-(1-hydroxy-1-methylethyl)-1-[(2'-oxalobiphenyl-4-yl)methyl]imidazole-5-carboxylic acid Following a procedure similar to that described in Example 1(b), but using 878 mg of ethyl 2-butyl-4-(1-hydroxy- 1-methylethyl)-1-[(2'-methoxalylbiphenyl-4-yl-)methyl]imidazole-5-carboxylate [prepared as described in step (a) above] and 364 mg of lithium hydroxide monohydrate, 571 mg of the title compound were obtained as a powder, softening at 140° C. and melting at 165°–170° C.

Nuclear Magnetic Resonance Spectrum (hexadeuterated dimethyl sulfoxide, 270 MHz), δ ppm: 0.82 (3H, triplet, J=7.5 Hz); 1.28 (2H, sextet, J=7.5 Hz); 1.47–1.60 (2H, multipier); 1.55 (6H, singlet); 2.63 (2H, triplet, J=7.5 Hz); 6.71 (2H, singlet); 7.08 (2H, doublet, J=8 Hz); 7.26 (2H, doublet, J=8 Hz); 7.46 (1H, doublet, J=7 Hz); 7.55 (1H, triplet, J=7 Hz); 7.67–7.72 (2H, multipier).

EXAMPLE 3

Ethyl 4-(1-hydroxy-1-methylethyl)-1-[(2'-oxalobiphenyl-4-yl)methyl]-2-propylimidazole-5-carboxylate hydrochloride (hydrochloride of Compound No. 1-26).

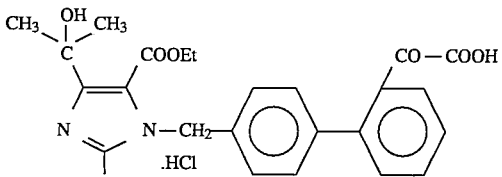

3(a) Ethyl 1-[(2'-t-butoxyoxalylbiphenyl-4-yl)methyl]-4-(1-hydroxy-1-methylethyl)-2-propylimidazole-5-carboxylate Following a procedure similar to that described in Example 1(a), but using 2.18 g of ethyl 4-(1-hydroxy-1-methylethyl)-2-propylimidazole-5-carboxylate, 1.12 g of potassium t-butoxide and 3.75 g of t-butyl (4'-bromomethylbiphenyl-2-yl)glyoxylate (prepared as described in Preparation 9), 3.73 g of the title compound were obtained as a gum.

Nuclear Magnetic Resonance Spectrum (CDCl$_3$, 270 MHz), δ ppm: 0.98 (3H, triplet, J=7.5 Hz); 1.16 (9H, singlet); 1.23 (2H, triplet, J=7 Hz); 1.64 (6H, singlet); 1.76 (2H, sextet, J=7.5 Hz); 2.63 (2H, triplet, J=7.5 Hz); 4.25 (2H, quartet, J=7 Hz); 5.50 (2H, singlet); 5.73 (1H, singlet); 7.00 (2H, doublet, J=8 Hz); 7.30 (2H, doublet, J=8 Hz); 7.40 (1H, doublet, J=7 Hz); 7.48 (1H, triplet, J=7 Hz); 7.60 (1H, triplet, J=7 Hz); 7.71 (1H, doublet, J=7 Hz).

3(b) Ethyl 4-(1-hydroxy-1-methylethyl)-1-[(2'-oxalobiphenyl-4-yl)methyl]-2-propylimidazole-5-carboxylate hydrochloride 570 mg of ethyl 1-[(2'-t-butoxyoxalylbiphenyl-4-yl)methyl]-4-(1-hydroxy-1-methylethyl)-2-propylimidazole-5carboxylate [prepared as described in step (a) above] were dissolved in 6 ml of a 4N solution of hydrogen chloride in dioxane, and the resulting solution was stirred at room temperature for 4 hours. At the end of this time, the reaction mixture was concentrated by evaporation under reduced pressure, and the resulting residue was triturated in diethyl ether, to give 448 mg of the title compound, as a crystalline powder, melting at 156°–158° C.

Nuclear Magnetic Resonance Spectrum (hexadeuterated dimethyl sulfoxide, 270 MHz), δ ppm: 0.89 (3H, triplet, J=7.5 Hz); 1.17 (3H, triplet, J=7 Hz); 1.50–1.65 (2H, multipier); 1.61 (6H, singlet); 2.96 (2H, triplet, J=7.5 Hz); 4.24 (2H, quartet, J=7 Hz); 5.65 (2H, singlet); 7.17 (1H, doublet, J=8 Hz); 7.29 (2H, doublet, J=8 Hz); 7.46 (1H, doublet, J=7 Hz); 7.57 (1H, triplet, J=7 Hz); 7.68–7.74 (2H, multipier).

EXAMPLE 4

Pivaloyloxymethyl 4-(1-hydroxy-1-methylethyl)-1-[(2'-oxalobiphenyl-4-yl)methyl]-2-propylimidazole-5-carboxylate hydrochloride (hydrochloride of Compound No. 1-27)

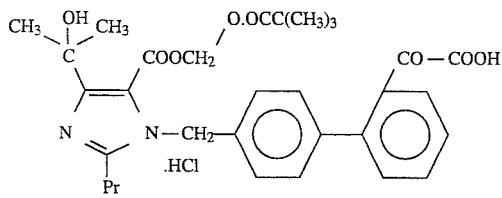

4(a) Pivaloyloyxymethyl 1-[(2'-t-butoxyoxalylbiphenyl-4-yl)methyl]-4-(1-hydroxy-1-methylethyl)-2-propylimidazole- 5-carboxylate Following a procedure similar to that described in Example 1(a), but using 1.64 g of pivaloyloxymethyl 4-(1-hydroxy-1-methylethyl)-2-propylimidazole-5-carboxylate, 617 mg of potassium t-butoxide and 2.25 g of t-butyl (4'-bromomethylbiphenyl-2-yl)glyoxylate (prepared as described in Preparation 9), 936 mg of the title compound were obtained as a gum.

Nuclear Magnetic Resonance Spectrum (CDCl$_3$, 270 MHz), δ ppm: 1.00 (3H, triplet, J=7.5 Hz); 1.15 (9H, singlet); 1.17 (3H, singlet); 1.62 (6H, singlet); 1.82 (2H, sextet, J=7.5 Hz); 2.64 (2H, triplet, J=7.5 Hz); 5.37 (1H, singlet); 5.48 (2H, singlet); 5.84 (2H, singlet); 7.03 (2H, doublet, J=8 Hz); 7.30 (2H, doublet, J=8 Hz); 7.39 (1H, doublet, J=7 Hz); 7.48 (1H, triplet, J=7 Hz); 7.60 (1H, triplet, J=7 Hz); 7.71 (1H, doublet, J=7 Hz).

4(b) Pivaloyloxymethyl-4-(1-hydroxy-1-methylethyl)-1-[(2'-oxalobiphenyl-4-yl)methyl]-2-propylimidazole-5carboxylate hydrochloride 936 mg of pivaloyloxymethyl 1-[(2'-t-butoxyoxalylbiphenyl-4-yl)methyl]-4-(1-hydroxy-1-methylethyl)-2-propylimidazole- 5-carboxylate [prepared as described in step (a) above] were treated with 10 ml of a 4N solution of hydrogen chloride in dioxane in the same manner as described in Example 3(b), to give 655 mg of the title compound as an amorphous powder, softening at 85° C.

Nuclear Magnetic Resonance Spectrum (hexadeuterated dimethyl sulfoxide, 270 MHz), δ ppm: 0.88 (3H, triplet, J=7.5 Hz); 1.10 (9H, singlet); 1.48–1.62 (2H, multiplet); 1.58 (6H, singlet); 2.90 (2H, triplet, J=7.5 Hz); 5.64 (2H, singlet); 5.88 (2H, singlet); 7.17 (2H, doublet, J=8 Hz); 7.28 (2H, doublet, J=8 Hz); 7.46 (1H, doublet, J=7 Hz); 7.57 (1H, triple, J=7 Hz); 7.68—7.74 (2H, multiplet).

EXAMPLE 5

(5-Methyl-2-oxo-1,3-dioxolen-4-yl)methyl 4-(1-hydroxy-1-methylethyl)-1-[2'-oxalobiphenyl-4-yl)methyl]-2-propylimidazole- 5-carboxylate hydrochloride hydrochloride of Compound No. 1-28

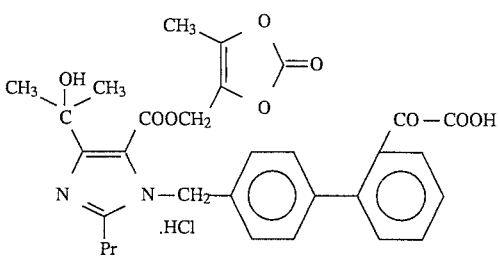

5(a) (5-Methyl-2oxo-1,3-dioxolen-4-yl)methyl 1-[2'-t-butoxyoxalylbiphenyl-4-yl)methyl]-4-(1-hydroxy-1-methylethyl)- 2-propylimidazole-5-carboxylate A solution of 315 mg of (5-methyl-2-oxo-1,3-dioxolen-4-yl)methyl 4-(1-hydroxy-1-methylethyl)-2-propylimidazole-5-carboxylate and 364 mg of t-butyl (4'-bromomethylbiphenyl- 2-yl)glyoxylate (prepared as described in Preparation 9) dissolved in 10 ml of dimethylacetamide was added dropwise, with stirring, to 3 ml of dimethylacetamide containing 268 mg of a powdery potassium carbonate, which had been heated to 60° C. After the dropwise addition, the resulting mixture was stirred at 60° C for 1.5 hours. At the end of this time, ethyl acetate and water were added to the reaction mixture, and the organic solvent layer was separated, washed with water and dried over anhydrous magnesium sulfate. The solvent was then removed by evaporation under reduced pressure. The resulting residue was subjected to column chromatography through silica gel, using a 1:1 by volume mixture of ethyl acetate and hexane as the eluent, to obtain a crystalline compound. This product was then washed with diisopropyl ether, to give 195 mg of the title compound, melting at 154°–156° C.

Nuclear Magnetic Resonance Spectrum (CDCl$_3$, 270 MHz), δ ppm: 1.00 (3H, triplet, J=7.5 Hz); 1.18 (9H, singlet); 1.62 (6H, singlet); 1.78 (2H, sextet, J=7.5 Hz); 2.08 (3H, singlet); 2.66 (2H, triplet, J=7.5 Hz); 4.92 (2H, singlet); 5.43 (2H, singlet); 5.55 (1H, singlet); 6.96 (2H, doublet, J=8 Hz); 7.30 (2H, doublet, J=8 Hz); 7.44 (1H, doublet, J=7 Hz); 7.49 (1H, triplet, J=7 Hz); 7.63 (1H, triplet, J=7 Hz); 7.71 (1H, doublet, J=7 Hz).

5(b) (5-Methyl-2-oxo-1,3-dioxolen-4-yl)methyl 4-(1-hydroxy- 1-methylethyl)-1-[(2'-oxalobiphenyl-4-yl )methyl]-2-propylimidazole-5-carboxylate hydrochloride 360 mg of (5-methyl-2-oxo-1,3-dioxolen-4-yl)methyl 1-[2'-t-butoxyoxalylbiphenyl-4-yl)methyl]-4-(1-hydroxy-1-methylethyl)-2-propylimidazole-5-carboxylate [prepared as described in step (a) above] were treated with 5 ml of a 4N solution of hydrogen chloride in dioxane in the same manner as described in Example 3(b), to give 308 mg of the title compound, as an amorphous powder, softening at 80° C. and above.

Nuclear Magnetic Resonance Spectrum (hexadeuterated dimethyl sulfoxide, 270 MHz), δ ppm: 0.89 (3H, triplet, J=7.5 Hz); 1.50–1.62 (2H, multipier); 1.59 (9H, singlet);

2.12 (6H, singlet); 2.95 (2H, triplet, J=7.5 Hz); 5.15 (2H, singlet); 5.63 (2H, singlet); 7.15 (2H, doublet, J=8 Hz); 7.27 (2H, doublet, J=8 Hz); 7.48 (1H, doublet, J=7 Hz); 7.57 (1H, triplet, J=7 Hz); 7.68–7.76 (2H, multipier).

EXAMPLE 6

4-Hydroxymethyl-1-[(2'-oxalobiphenyl-4-yl)methyl]-2-propylimidazole-5-carboxylic acid (Compound No. 1-4)

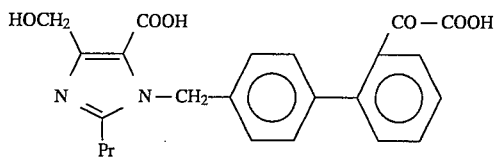

6(a) Ethyl 4-acetoxymethyl-1-[(2'-methoxalylbiphenyl-4-yl)methyl]-2-propylimidazole-5-carboxylate 210 mg of potassium carbonate and 583 mg of methyl (4'-bromomethylbiphenyl-2-yl)glyoxylate (prepared as described in Preparation 8) were added, in that order, to 5 ml of a solution of 387 mg of ethyl 4-acetoxymethyl-2-propylimidazole-5-carboxylate dissolved in dimethylacetamide, and the resulting mixture was stirred at room temperature for 16 hours. At the end of this time, ethyl acetate and water were added to the reaction mixture, and the organic solvent layer was separated, washed with water and with a saturated aqueous solution of sodium chloride and dried over anhydrous magnesium sulfate. The solvent was then removed by evaporation under reduced pressure. The resulting residue was subjected to column chromatography through silica gel, using a 2:1 by volume mixture of ethyl acetate and hexane as the eluent, to give 696 mg of the title compound as a gum from the fraction eluted first.

Nuclear Magnetic Resonance Spectrum (CDCl₃, 270 MHz), δ ppm: 0.98 (3H, triplet, J=7.5 Hz); 1.31 (3H, triplet, J=7 Hz); 1.77 (2H, sextet, J=7.5 Hz); 2.12 (3H, singlet); 2.65 (2H, triplet, J=7.5 Hz); 3,30 (3H, singlet); 4.26 (2H, quartet, J=7 Hz); 5.33 (2H, singlet); 5.61 (2H, singlet); 7.04 (2H, doublet, J=8 Hz); 7.27 (2H, doublet, J=8 Hz); 7.42 (1H, doublet, J=7 Hz); 7.51 (1H, triplet, J=7 Hz); 7.64 (1H, triplet, J=7 Hz); 7.82 (1H, doublet, J=7 Hz).

From the fraction eluted next were obtained 156 mg of ethyl 5-acetoxymethyl-1-[(2'-methoxalylbiphenyl-4-yl)methyl]-2-propylimidazole-4-carboxylate which is an isomer of the title compound.

Nuclear Magnetic Resonance Spectrum (CDCl₃, 270 MHz), δ ppm: 0.96 (3H, triplet, J=7.5 Hz); 1.41 (3H, triplet, J=7 Hz); 1.75 (2H, sextet, J=7.5 Hz); 1.92 (3H, singlet); 2.63 (2H, triplet, J=7.5 Hz); 3.41 (3H, singlet); 4.42 (2H, quartet, J=7 Hz); 5.25 (2H, singlet); 5.43 (2H, singlet); 6.99 (2H, doublet, J=8 Hz); 7.29 (2H, doublet, J=8 Hz); 7.40 (1H, doublet, J=7 Hz); 7.52 (1H, triplet, J=7 Hz); 7.64 (1H, triplet, J=7 Hz); 7.80 (1H, doublet, J=7 Hz).

6(b) 4-Hydroxymethyl-1-[2'-oxalobiphenyl-4-yl)methyl]-2-propylimidazole-5-carboxylic acid 8.2 ml of an 1N aqueous solution of sodium hydroxide were added to a solution of 696 mg of ethyl 4-acetoxymethyl-1-[(2'-methoxalylbiphenyl-4-yl)methyl]-2-propylimidazole-5-carboxylate [prepared as described in step (a) above] dissolved in 8.9 ml of dioxane, and the resulting mixture was stirred at room temperature for 16 hours. At the end of this time, the dioxane was removed by distillation under reduced pressure, and 8.2 ml of a 1N aqueous solution of hydrochloric acid were added to the residual aqueous solution. The crystals thus Precipitated were collected by filtration, to give 428 mg of the title compound, melting at 223°–225° C. (with decomposition).

Nuclear Magnetic Resonance Spectrum (hexadeuterated dimethyl sulfoxide, 270 MHz), δ ppm: 0.88 (3H, triplet, J=7.5 Hz); 1.61 (2H, sextet, J=7.5 Hz); 2.64 (2H, triplet, J=7.5 Hz); 4.66 (2H, singlet); 5.68 (2H, singlet); 7.09 (2H, doublet, J=8 Hz); 7.27 (2H, doublet, J=8 Hz); 7.45 (1H, doublet, J=7 Hz); 7.54 (1H, triplet, J=7 Hz); 7.65–7.73 (2H, multiplet).

EXAMPLE 7

{4-[4-(1-Hydroxy-1-methylethyl)-2-propyl-5-(tetrazol-5-yl)imidazol-1-ylmethyl]biphenyl-2-yl}glyoxylic acid (Compound No. 1-40)

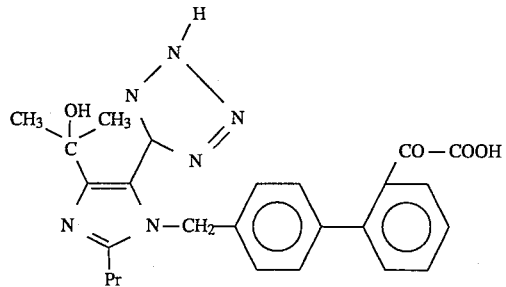

7(a) Methyl {4'-[4-(1-hydroxy-1-methylethyl)-2-propyl-5-(2-trityltetrazol-5-yl)imidazol-1-ylmethyl]biphenyl-2-yl}glyoxylate Following a procedure similar to that described in Example 1(a), but using 479 mg of 4-(1-hydroxy-1-methylethyl)-2-propyl-2-(2-trityltetrazol-5-yl)imidazole, 123 mg of potassium t-butoxide and 366 mg of methyl (4'-bromomethylbiphenyl-2-yl)glyoxylate (prepared as described in Preparation 8), 527 mg of the title compound were obtained as a gum.

Nuclear Magnetic Resonance Spectrum (CDCl₃, 270 MHz), δ ppm: 0.97 (3H, triplet, J=7.5 Hz); 1.57 (9H, singlet); 1.74 (2H, sextet, J=7.5 Hz); 2.65 (2H, triplet, J=7.5 Hz); 3.14 (3H, singlet); 5.32 (1H, singlet); 5.43 ( (2H, singlet); 6.74 (2H, doublet, J=8 Hz); 7.00–7.03 (6H, multipier); 7.12 (2H, doublet, J=8 Hz); 7.26–7.37 (10H, multiplet); 7.51 (1H, triplet, J=7 Hz); 7.64 (1H, triplet, J=7 Hz); 7.81 (1H, doublet, J=7 Hz).

7(b) Methyl {4'-[4-(1-hydroxy-1-methylethyl)-2-propyl-5-(tetrazol-5-yl)imidazol-1-ylmethyl]biphenyl-2-yl}glyoxylate 1.5 ml of water were added to a solution of 527 mg of methyl {4'-[4-(1-hydroxy-1-methylethyl)-2-propyl-5-(2-trityltetrazol-5-yl)imidazol-1-ylmethyl]biphenyl-2-yl}glyoxylate [prepared as described in step (a) above] dissolved in 3.5 ml of acetic acid, and the resulting mixture was stirred at 70° C. for 1.5 hours. At the end of this time, 2 ml of water were added to the mixture. The resulting mixture was ice-cooled, and then the precipitate was removed by filtration. The filtrate was concentrated by evaporation under reduced pressure, and the residual acetic acid was removed by azeotropic distillation with toluene, to give 206 mg of the title compound, as crystals melting at 131°–132° C. (after crystallization from a mixture of diethyl ether and ethyl acetate).

Nuclear Magnetic Resonance Spectrum (hexadeuterated dimethyl sulfoxide, 270 MHz), δ ppm: 0.90 (3H, triplet, J=7.5 Hz); 1.47 (6H, singlet); 1.59 (2H, sextet, J=7.5 Hz); 2.80 (2H, triplet, J=7.5 Hz); 3.16 (3H, singlet); 5.67 (2H, singlet); 7.08 (2H, doublet, J=8 Hz); 7.21 (2H, doublet, J=8 Hz); 7.47 (1H, doublet, J=7 Hz); 7.58 (1H, triplet, J=7 Hz); 7.70–7.77 (2H, multipier).

7(c) {4'-[4-(1-Hydroxy-1-methylethyl)-2-propyl-5-(tetrazol-5-yl)imidazol-1-ylmethyl]biphenyl-2-yl}glyoxylic acid Following a procedure similar to that described in Example 1(b), but using 180 mg of methyl {4'-[4-(1-hydroxy-1-methylethyl)-2-propyl-5-(tetrazol-5-yl)imidazol-1-ylmethyl]biphenyl-2-yl}glyoxylate [prepared as described in step (b) above] and 77 mg of lithium hydroxide monohydrate, 95 mg of the title compound, melting at 169°–170°C., were obtained.

Nuclear Magnetic Resonance Spectrum (hexadeuterated dimethyl sulfoxide, 270 MHz), δ ppm: 0.87 (3H, triplet, J=7.5 Hz); 1.43 (6H, singlet); 1.53 (2H, sextet, J=7.5 Hz); 2.81 (2H, triplet, J=7.5 Hz); 5.55 (2H, singlet); 7.12 (2H, doublet, J=8 Hz); 7.22 (2H, doublet, J=8 Hz); 7.42 (1H, doublet, J=7 Hz); 7.56 (1H, triplet, J=7 Hz); 7.66–7.75 (2H, multipier).

EXAMPLE 8

4-Isopropenyl-1-[(2'-oxalobiphenyl-4-yl) methyl]-2-propylimidazole-5-carboxylic acid (Compound No. 1-10)

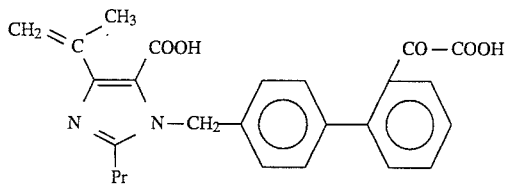

8(a) Ethyl 4-isopropenyl-1-[(2'-methoxalylbiphenyl-4-methyl]-2-propylimidazol-5-carboxylate Following a procedure similar to that described in Example 1(a), but using 445 mg of ethyl 4-isopropenyl-2-propylimidazole-5-carboxylate, 247 mg of potassium t-butoxide and 733 mg of methyl (4'-bromomethylbiphenyl-2-yl)glyoxylate (prepared as described in Preparation 8), 570 mg of the title compound were obtained as a syrup.

Nuclear Magnetic Resonance Spectrum (CDCl₃, 270 MHz), δ ppm: 1.00 (3H, triplet, J=7.5 Hz); 1.29 (3H, triplet, J=7 Hz); 1.78 (2H, sextet, J=7.5 Hz); 2.16 (3H, singlet); 2.66 (2H, triplet, J=7.5 Hz); 3.32 (3H, singlet); 4.23 (2H, quartet, J=7 Hz); 5.29 (2H, singlet); 5.57 (2H, singlet); 7.07 (2H, doublet, J=8 Hz); 7.29 (2H, doublet, J=8 Hz); 7.44 (1H, doublet, J=7 Hz); 7.52 (1H, triplet, J=7 Hz); 7.66 (1H, triplet, J=7 Hz); 7.84 (1H, doublet, J=7 Hz).

8(b) 4-Isopropenyl-1-[(2'-oxalobiphenyl-4-yl)methyl]-2propylimidazole-5-carboxylic acid A solution of 279 mg of ethyl 4-isopropenyl-1-[(2'-methoxalylbiphenyl-4-yl)methyl)-2-propylimidazole-5-carboxylate [prepared as described in step (a) above] dissolved in 3 ml of dioxane was mixed with a solution of 123 mg of lithium hydroxide monohydrate dissolved in 3 ml of water, and the resulting mixture was stirred at 80° C. for 5 hours. At the end of this time, the dioxane was removed by distillation under reduced pressure, and 2.94 ml of 1N aqueous hydrochloric acid were added to the residual aqueous solution. The crystals which precipitated were collected by filtration, to give 214 mg of the title compound, melting at 150°–151° C.

Nuclear Magnetic Resonance Spectrum (hexadeuterated dimethyl sulfoxide, 270 MHz), δ ppm: 0.90 (3H, triplet, J=7.5 Hz); 1.63 (2H, sextet, J=7.5 Hz); 2.07 (6H, singlet); 2.60 (2H, triplet, J=7.5 Hz); 5.21 (1H, singlet); 5.30 (1H, singlet); 5.58 (2H, singlet); 7.10 (2H, doublet, J=8 Hz); 7.26 (2H, doublet, J=8 Hz); 7.46 (1H, doublet, J=7 Hz); 7.54 (1H, triplet, J=7 Hz); 7.66–7.72 (2H, multipier).

EXAMPLE 9

4-Isopropyl-1-[(2'-oxalobiphenyl-4-yl)methyl]-2-propylimidazole-5-carboxylic acid (Compound No. 1-8)

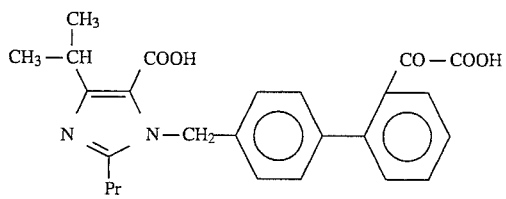

9(a) Ethyl 4-isopropyl-1-[(2'-methoxalylbiphenyl-4-yl)methyl]-2-propylimidazole-5-carboxylate Following a procedure similar to that described in Example 1(a), but using 448 mg of ethyl 4-isopropyl-2-propylimidazole-5-carboxylate, 247 mg of potassium t-butoxide and 733 mg of methyl (4'-bromomethylbiphenyl-2-yl)glyoxylate (prepared as described in Preparation 8), 760 mg of the title compound were obtained as a syrup.

Nuclear Magnetic Resonance Spectrum (CDCl₃, 270 MHz), δ ppm: 0.96 (3H, triplet, J=7.5 Hz); 1.29 (6H, doublet, J=7 Hz); 1.31 (3H, triplet, J=7 Hz); 1.67 (2H, sextet, J=7.5 Hz); 2.65 (2H, triplet, J =6.5 Hz); 3.29 (3H, singlet); 3.61 (1H, septet, J=7.5 Hz); 4.24 (2H, quartet, J=7 Hz); 5.56 (2H, singlet); 7.01 (2H, doublet, J=8 Hz); 7.25 (2H, doublet, J=8 Hz); 7.42 (1H, doublet, J=7 Hz); 7.50 (1H, triplet, J=7 Hz); 7.63 (1H, triplet, J=7 Hz); 7.81 (1H, doublet, J=7 Hz).

9(b) 4-Isopropyl-[(2'-oxalobiphenyl-4-yl)methyl]-2-propylimidazole-5-carboxylic acid Following a procedure similar to that described in Example 8(b), but using 760 mg of ethyl 4-isopropyl-1-[(2'-methoxalylbiphenyl-4-yl)methyl]-2'-propylimidazole-5-carboxylate [prepared as described in step (a) above] and 335 g of lithium hydroxide monohydrate, 527 mg of the title compound were obtained as a powder, melting at 177°–178° C.

Nuclear Magnetic Resonance Spectrum (hexadeuterated dimethyl sulfoxide, 270 MHz), δ ppm: 0.88 (3H, triplet, J=7.5 Hz); 1.21 (6H, doublet, J=7.5 Hz); 1.60 (2H, sextet, J=7.5 Hz); 2.60 (2H, triplet, J=7.5 Hz); 3.64 (1H, septet, J=7.5 Hz); 5.62 (2H, singlet); 7.06 (2H, doublet, J=8 Hz); 7.26 (2H, doublet, J=8 Hz); 7.45 (1H, doublet, J=7 Hz); 7.53 (1H, triplet, J=7 Hz); 7.65–7.72 (2H, multipier).

EXAMPLE 10

4-(1-Hydroxy-2-methylpropyl)-1-[(2'-oxalobiphenyl-4-yl)-methyl]-2-propylimidazole-5-carboxamide (Compound No. 1-22)

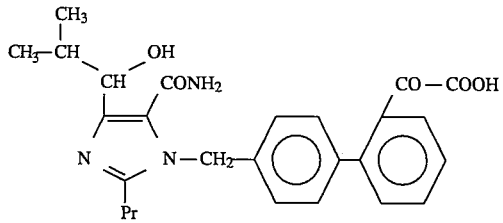

10(a) 4-(1-Hydroxy-2-methylpropyl)-1-[(2'-methoxalylbiphenyl-4-yl)methyl]-2-propylimidazole-5-carbonitrile 107 mg of potassium carbonate and 309 mg of methyl (4'-bromomethylbiphenyl-2-yl)glyoxylate (prepared as described in Preparation 8) were added to a solution of 160 mg of 4-(1-hydroxy-2-methylpropyl)-2-propylimidazole-5-carbonitrile dissolved in 3.5 mg of dimethylacetamide, and the resulting mixture was stirred at room temperature for 3 hours. At the end of this time, ethyl acetate and water were added to the reaction mixture. The ethyl acetate layer was separated and dried over anhydrous magnesium sulfate, and then the solvent was removed by distillation under reduced pressure. The resulting residue was subjected to column chromatography through silica gel, using a 2:1 by volume mixture of ethyl acetate and hexane as the eluent, to give 180 mg of the title compound, as crystals, melting at 113° C.

Nuclear Magnetic Resonance Spectrum (CDCl$_3$, 270 MHz), δ ppm: 0.94 (3H, doublet, J=6.5 Hz); 0.97 (3H, triplet, J=7.5 Hz); 1.00 (3H, doublet, J=6.5 Hz); 1.75 (2H, sextet, J=7.5 Hz); 2.07–2.20 (1H, multipier); 2.64 (2H, triplet, J=7.5 Hz); 3.36 (3H, singlet); 4.55 (1H, doublet, J=6 Hz); 5.24 (2H, singlet); 7.13 (2H, doublet, J=8 Hz); 7.33 (2H, doublet, J=8 Hz); 7.42 (1H, doublet, J=7 Hz); 7.52 (1H, triplet, J=7 Hz); 7.65 (1H, doublet, J=7 Hz); 7.82 (1H, doublet, J=7 Hz).

10(b) 4-(1-Hydroxy-2-methylpropyl)-1-[(2'-oxalobiphenyl-4-yl)-methyl]-2-propylimidazole-5-carboxamide 4 ml of a 1N aqueous solution of sodium hydroxide were added to a solution of 170 mg of 4-(1-hydroxy-2-methyl-propyl)-1-[(2'-methoxalylbiphenyl-4-yl)methyl]-2-propy-limidazole-5-carbonitrile [prepared as described in step (a) above] dissolved in 3 ml of hot ethanol, and the resulting mixture was stirred under reflux for 2.5 hours. At the end of this time, the ethanol was removed by evaporation under reduced pressure, and ethyl aceate was added to the residual aqueous solution. 4 ml of 1N aqueous hydrochloric acid were added to the mixture, after which the ethyl acetate layer was separated. This extract was then dried over anhydrous magnesium sulfate, and the solvent was removed by evaporation under reduced pressure to give 140 mg of the title compound as crystals, softening at 150° C., and melting at 165°–170° C. (with decomposition).

Nuclear Magnetic Resonance Spectrum (hexadeuterated dimethyl sulfoxide, 270 MHz), δ ppm: 0.69 (3H, doublet, J=6.5 Hz); 0.85 (3H, triplet, J=7.5 Hz); 1.01 (3H, doublet, J=6.5 Hz); 1.58 (2H, sextet, J=7.5 Hz); 2.01–2.16 (2H, multipier); 2.54 (2H, triplet, J=7.5 Hz); 4.32 (1H, doublet, J=8.5 Hz); 5.54 (1H, doublet, J=16.5 Hz); 5.79 (1H, doublet, J=16.5 Hz); 6.21 (1H, broad singlet); 7.06 (2H, doublet, J=8 Hz); 7.25 (2H, doublet, J=8 Hz); 7.41 (1H, broad singlet); 7.45 (1H, doublet, J=7 Hz); 7.53 (1H, triplet, J=7 Hz); 7.64–7.71 (2H, multipier); 8.49 (1H, broad singlet).

EXAMPLE 11

4-(1-Hydroxy-2,2-dimethylpropyl)-1-[(2'-oxalobiphenyl-4-yl)methyl]-2-propylimidazole-5-carboxamide. (Compound No. 1-24)

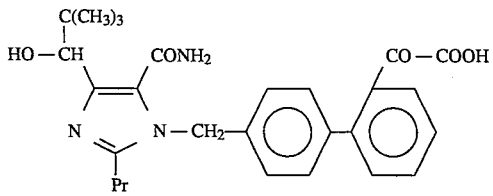

11(a) 4-(1-Hydroxy-2,2-dimethylpropyl)-1-[(2'-methoxalyl-biphenyl-4-yl)methyl]-2-propylimidazole-5-carbonitrile Following a procedure similar to that described in Example 10(a), but using 170 mg of 4-(1-hydroxy-2,2-dimethylpropyl)-2-propylimidazole-5-carbonitrile, 307 mg of methyl (4'-bromomethylbiphenyl-2-yl)glyoxylate (prepared as described in Preparation 8) and 106 mg of potassium carbonate, 257 mg of the title compound were obtained as crystals, melting at 128°–130° C.

Nuclear Magnetic Resonance Spectrum (CDCl$_3$, 270 MHz), δ ppm: 0.97 (3H, triplet, J=7.5 Hz); 0.99 (9H, singlet); 1.75 (2H, sextet, J=7.5 Hz); 2.64 (2H, triplet, J=7.5 Hz); 2.76 (1H, doublet, J=7 Hz); 3.35 (3H, singlet); 4.45 (1H, doublet, J=7 Hz); 5.23 (2H, singlet); 7.13 (2H, doublet, J=8 Hz); 7.33 (2H, doublet, J=8 Hz); 7.42 (1H, doublet, J=7 Hz); 7.53 (1H, triplet, J=7 Hz); 7.66 (1H, triplet, J=7 Hz); 7.82 (1H, doublet, J=7 Hz).

11(b) 4-(1-Hydroxy-2,2-dimethylpropyl)-1-[(2'-oxalobiphe-nyl-4-yl)methyl]-2-propylimidazole-5-carboxamide 246 mg of 4-(1-hydroxy-2,2-dimethylpropyl)-1-[(2'-methoxalylbiphenyl-4-yl)methyl]-2-propylimidazole-5-carbonitrile [prepared as described in step (a) above] were subjected to hydrolysis using 6 ml of a 1N aqueous solution of sodium hydroxide in the same manner as described in Example 10(b), to give 182 mg of the title compound as crystals, melting at 198°–200° C.

Nuclear Magnetic Resonance Spectrum (hexadeuterated dimethyl sulfoxide, 270 MHz), δ ppm: 0.85 (3H, triplet, J=7.5 Hz); 0.89 (9H, singlet); 1.58 (2H, sextet, J=7.5 Hz); 2.56 (2H, triplet, J=7.5 Hz); 4.51 (1H, singlet); 5.48 (1H, doublet, J=16.5 Hz); 5.81 (1H, doublet, J=16.5 Hz); 6.22 (1H, broad singlet); 7.05 (2H, doublet, J=8 Hz); 7.26 (2H, doublet, J=8 Hz); 7.39 (1H, broad singlet); 7.44 (1H, doublet, J=7 Hz); 7.52 (1H, doublet, J=7 Hz); 7.64–7.71 (2H, multipier); 8.68 (1H, broad singlet).

EXAMPLE 12

2-Butyl-4-(1-hydroxy-2-methylpropyl)-1-[(2'-oxalobiphe-nyl-4-yl)methyl]imidazole-5-carboxamide (Compound No. 1-23)

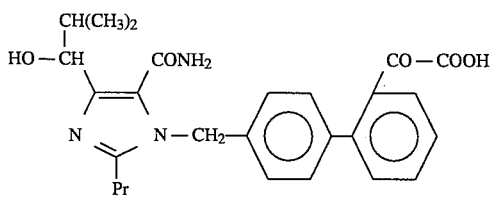

12(a) 2-Butyl-4-(1-hydroxy-2-methylpropyl)-1-[(2'-methoxalylbiphenyl-4-yl)methyl]imidazole-5-carbonitrile Following a procedure similar to that described in Example 10(a), but using 178 mg of 2-butyl-4-(1-hydroxy-2-methylpropyl)imidazole-5-carbonitrile, 322 mg of methyl (4'-bromomethylbiphenyl-2-yl) glyoxylate (prepared as described in Preparation 8) and 111 mg of potassium carbonate, 245 mg of the title compound were obtained as a syrup.

Nuclear Magnetic Resonance Spectrum (CDCl₃, 270 MHz), δ ppm: 0.91 (3H, triplet, J=7.5 Hz); 0.94 (3H, doublet, J=6.5 Hz); 1.00 (3H, doublet, J=6.5 Hz); 1.37 (2H, sextet, J=7.5 Hz); 1.70 (2H, quintet, J=8 Hz); 2.07–2.19 (1H, multipier); 2.66 (2H, triplet, J=8 Hz); 3.36 (3H, singlet); 4.54 (1H, doublet, J=6 Hz); 5.23 (2H, singlet); 7.13 (2H, doublet, J=8 Hz); 7.33 (2H, doublet, J=8 Hz); 7.42 (1H, doublet, J=7 Hz); 7.52 (1H, triplet, J=7 Hz); 7.66 (1H, triplet, J=7 Hz); 7.82 (1H, doublet, J=7 Hz).

12(b) N-Butyl-4-(1-hydroxy-2-methylpropyl)-1-[(2'-oxalobiphenyl-4-yl)methyl]imidazole-5-carboxamide 245 mg of 2-butyl-4-(1-hydroxy-2-methylpropyl)-1-[(2'-methoxalylbiphenyl-4-yl)methyl]imidazole-5-carbonitrile [prepared as described in step (a) above] were subjected to hydrolysis using 6 ml of a 1N aqueous solution of sodium hydroxide in the same manner as described in Example 10(b), to give 187 mg of the title compound as a powder, at softening 144°–146° C.

Nuclear Magnetic Resonance Spectrum (hexadeuterated dimethyl sulfoxide, 270 MHz), δ ppm: 0.69 (3H, doublet, J=6.5 Hz); 0.81 (3H, triplet, J=7.5 Hz); 1.01 (3H, doublet, J=6.5 Hz); 1.26 (2H, sextet, J=7.5 Hz); 1.52 (2H, quintet, J=7.5 Hz); 1.99–2.16 (1H, multipier); 2.57 (2H, triplet, J=7.5 Hz); 4.33 (1H, doublet, J=8.5 Hz); 5.55 (1H, doublet, J=16.5 Hz); 5.78 (1H, doublet, J=16.5 Hz); 6.22 (1H, broad singlet); 7.07 (2H, doublet, J=8 Hz); 7.25 (2H, doublet, J=8 Hz); 7.45 (1H, doublet, J=7 Hz); 7.54 (1H, triplet, J=7 Hz); 7.50 (1H, broad singlet); 7.64–7.72 (2H, multipier); 8.50 (1H, broad singlet).

EXAMPLE 13

2-Butyl-4-(1-hydroxy-2,2-dimethylpropyl)-1-[(2'-oxalobiphenyl-4-yl)methyl]imidazole-5-carboxamide (Compound No. 1-25)

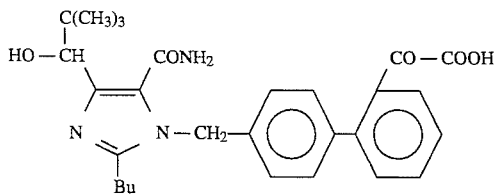

13(a) 2-Butyl-4-(1-hydroxy-2,2-dimethylpropyl)-1-[(2'-methoxalylbiphenyl-4-yl)methyl]imidazole-5-carbonitrile Following a procedure similar to that described in Example 10(a), but using 340 mg of 2-butyl-4-(1-hydroxy-2,2-dimethylpropyl)imidazole-5-carbonitrile, 340 mg of methyl (4'-bromomethylbiphenyl-2-yl)glyoxylate (prepared as described in Preparation 8) and 117 mg of potassium carbonate, 335 mg of the title compound were obtained as a syrup.

Nuclear Magnetic Resonance Spectrum (CDCl₃, 270 MHz), δ ppm: 0.91 (3H, triplet, J=7.5 Hz); 0.99 (9H, singlet); 1.36 (2H, sextet, J=7.5 Hz); 1.69 (2H, quintet, J=7.5 Hz); 2.66 (2H, triplet, J=7.5 Hz); 3.36 (3H, singlet); 4.46 (1H, singlet); 5.23 (2H, singlet); 7.13 (2H, doublet, J=8 Hz); 7.33 (2H, doublet, J=8 Hz); 7.42 (1H, doublet, J=7 Hz); 7.52 (1H, triplet, J=7 Hz); 7.63 (1H, triplet, J=7 Hz); 7.82 (1H, doublet, J=7 Hz).

13(b) 2-Butyl-4-(1-hydroxy-2,2-dimethylpropyl)-1-[(2'-oxalobiphenyl-4-yl)methyl]imidazole-5-carboxamide 335 mg of 2-butyl-4-(1-hydroxy-2,2-dimethylpropyl)-1-[(2'-methoxalylbiphenyl-4-yl)methyl]imidazole-5-carbonitrile [prepared as described in step (a) above] were subjected to hydrolysis using 7 ml of a 1N aqueous solution of sodium hydroxide in the same manner as described in Example 10(b), to give 256 mg of the title compound as a crystalline powder, melting at 192°–194° C. (with decomposition).

Nuclear Magnetic Resonance Spectrum (hexadeuterated dimethyl sulfoxide, 270 MHz), δ ppm: 0.81 (3H, triplet, J=7.5 Hz); 1.26 (2H, sextet, J=7.5 Hz); 1.51 (2H, quintet, J=7.5 Hz); 2.59 (2H, triplet, J=7.5 Hz); 4.51 (1H, singlet); 5.48 (1H, doublet, J=16.5 Hz); 5.80 (1H, doublet, J=16.5 Hz); 6.22 (1H, broad singlet); 7.06 (2H, doublet, J=8 Hz); 7.26 (2H, doublet, J=8 Hz); 7.42 (1H, broad singlet); 7.44 (1H, doublet, J=7 Hz); 7.53 (1H, triplet, J=7 Hz); 7.64–7.72 (2H, multipier); 8.69 (1H, broad singlet).

EXAMPLE 14

2-Ethoxymethyl-4-(1-hydroxy-1-methylethyl)-1-[(2'-oxalobiphenyl-4-yl)methyl]imidazole-5-carboxylic acid (Compound No. 1-37)

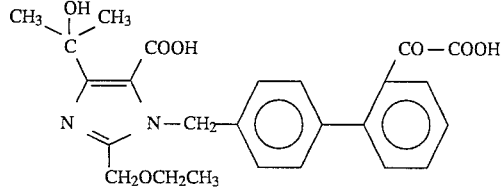

14(a) Ethyl-2-ethoxymethyl-4-(1-hydroxy-1-methylethyl)-1-[(2'-methoxalylbiphenyl-4-yl)methyl]imidazole-5-carboxylate Following a procedure similar to that described in Example 1(a), but using 400 mg of ethyl 2-ethoxymethyl-4-(1-hydroxy-1-methylethyl)imidazole-5-carboxylate, 546 mg of methyl (4'-bromomethylbiphenyl-2-yl)glyoxylate (prepared as described in Preparation 8) and 184 mg of potassium t-butoxide, 680 mg of the title compound were obtained as a syrup.

Nuclear Magnetic Resonance Spectrum (CDCl₃, 270 MHz), δ ppm: 1.16 (3H, triplet, J=7 Hz); 1.28 (3H, triplet, J=7 Hz); 1.64 (6H, singlet); 3.31 (3H, singlet); 3.54 (2H, quartet, J=7 Hz); 4.29 (3H, quartet, J=7 Hz); 4.57 (2H, singlet); 5.55 (1H, singlet); 5.66 (2H, singlet); 7.02 (2H, doublet, J=8.0 Hz); 7.26 (2H, doublet, J=8.0 Hz); 7.41 (1H, doublet, J=7.5 Hz); 7.51 (1H, triplet, J=7.5 Hz); 7.64 (1H, triplet, J=7.5 Hz); 7.81 (1H, doublet, J=7.5 Hz).

14(b) 2-Ethoxymethyl-4-(1-hydroxy-1-methylethyl)-1-[(2'-oxalobiphenyl-4-yl)methyl]imidazole-5-carboxylic acid 680 mg of ethyl 2-ethoxymethyl-4-(1-hydroxy-1-methylethyl)-1-[(2'-methoxalylbiphenyl-4-yl)methyl]imidazole-5-carboxylate [prepared as described in step (a) above] were subjected to hydrolysis using 224 mg of lithium hydroxide monohydrate in the same manner as described in Example 1(b), to give 423 mg of the title compound as a powder, melting at 138°–140° C.

Nuclear Magnetic Resonance Spectrum (hexadeuterated dimethyl sulfoxide, 270 MHz), δ ppm: 1.04 (3H, triplet, J=7.0 Hz); 1.56 (6H, singlet); 3.45 (2H, quartet, J=7.0 Hz);

4.47 (2H, singlet); 5.71 (2H, singlet); 7.09 (2H, doublet, J=8.0 Hz); 7.24 (2H, doublet, J=8.0 Hz); 7.47 (1H, doublet, J=7.5 Hz); 7.55 (1H, triplet, J=8.0 Hz); 7.66–7.73 (2H, multipier).

EXAMPLE 15

4-(1-Hydroxy-1-methylethyl)-2-(methylaminomethyl)-1-[(2'-oxalobiphenyl-4-yl) methyl]imidazole-5-carboxylic acid hydrochloride (hydrochloride of Compound No. 1-48)

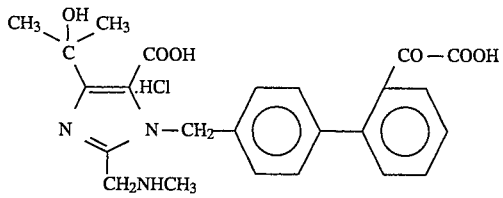

15(a) Methyl 2-(N-t-butoxycarbonyl-N-methylaminomethyl)-4-(1-hydroxy-1-methylethyl)-1-[(2'-methoxalylbiphenyl-4-yl)methyl]imidazole-5-carboxylate Following a procedure similar to that described in Example 1(a), but using 265 mg of ethyl 2-(N-t-butoxycarbonyl-N-methylaminomethyl)-4-(1-hydroxy-1-methylethyl)imidazole-5-carboxylate, 310 mg of methyl (4'-bromomethylbiphenyl-2-yl)glyoxylate (prepared as described in preparation 8) and 92 mg of potassium t-butoxide, 380 mg of the title compound were obtained as a syrup.

Nuclear Magnetic Resonance Spectrum (CDCl$_3$, 270 MHz), δ ppm: 1.28 (3H, triplet, J=7.5 Hz); 1.34 (9H, singlet); 1.63 (6H, singlet); 2.85 (3H, singlet); 3.32 (3H, singlet ); 4.27 (2H, quartet, J=7.5 Hz); 4.56 (2H, broad singlet); 5.60 (1H, broad singlet); 5.63 (2H, broad singlet); 6.93 (2H, doublet, J=8.0 Hz); 7.25 (2H, doublet, J=8.0 Hz); 7.39 (1H, doublet, J=8.0 Hz); 7.50 (1H, triplet, J=8.0 Hz); 7.64 (1H, triplet, J=8.0 Hz); 7.80 (1H, doublet, J=8.0 Hz).

15(b) 2-(N-t-Butoxycarbonyl-N-methylaminomethyl)-4-(1-hydroxy-1-methylethyl)-1-[(2'-oxalobiphenyl-4-yl)methyl] imidazole-5-carboxylic acid A solution of 81 mg of lithium hydroxide monohydrate dissolved in 5 ml of water was added to a solution of 380 mg of methyl 2-(N-t-butoxycarbonyl-N-methylaminomethyl)-4-(1-hydroxy-1-methylethyl)-1-[(2'-methoxalylbiphenyl-4-yl)methyl]imidazole-5-carboxylate [prepared as described in step (a) above] dissolved in 5 mg of dioxane, and the resulting mixture was stirred at room temperature for 2.5 hours. At the end of this time, the dioxane was removed by distillation under reduced pressure, and then 1.93 ml of 1N aqueous hydrochloric acid was added to the residue. The material which precipitated was collected by filtration to give 339 mg of the title compound as an amorphous powder.

Nuclear Magnetic Resonance Spectrum (hexadeuterated dimethyl sulfoxide, 270 MHz), δ ppm: 1.31 (9H, broad singlet); 1.55 (6H, singlet); 2.77 (3H, broad singlet); 4.43 (2H, broad singlet); 5.69 (2H, broad singlet); 7.03 (2H, doublet, J=8.0 Hz); 7.25 (2H, doublet, J=8.0 Hz); 7.44 (1H, doublet, J=8.0 Hz); 7.55 (1H, triplet, J=7.0 Hz); 7.66–7.72 (2H, multipier).

15(c) 4-(1-Hydroxy-1-methylethyl)-2-(methylaminomethyl)-1-[(2'-oxalobiphenyl-4-yl)methyl]imidazole-5-carboxylic acid hydrochloride 339 mg of 2-(N-t-Butoxycarbonyl-N-methylaminomethyl)- 4-(1-hydroxy-1-methylethyl)-1-[(2'-oxalobiphenyl-4-yl) methyl]imidazole-5-carboxylic acid [prepared as described in step (b) above] were subjected to de-t-butoxycarbonylation using 3 ml of a 4N solution of hydrogen chloride in dioxane in the same manner as described in Example 3(b), to give 260 mg of the title compound, melting at 172°–175° C. (with decomposition).

Nuclear Magnetic Resonance Spectrum (hexadeuterated dimethyl sulfoxide, 270 MHz), δ ppm: 1.60 (6H, singlet); 2.66 (3H, broad singlet); 4.27 (2H, broad singlet); 5.75 (2H, singlet); 7.12 (2H, doublet, J=8.0 Hz); 7.28 (2H, doublet, J=8.0 Hz); 7.48 (1H, doublet, J=7.5 Hz); 7.57 (1H, triplet, J=7.5 Hz); 7.68–7.74 (2H, multipier).

EXAMPLE 16

2-Ethyl-5,7-dimethyl-3-(2'-oxalobiphenyl-4-yl)methyl-3 H-imidazo-[4,5,-]pyridine (Compound No. 2-1)

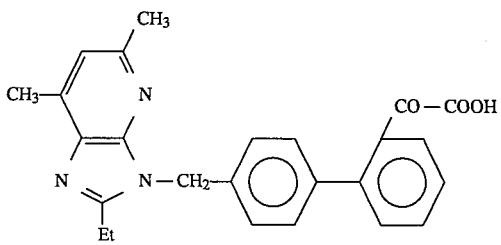

16(a) 2-Ethyl1,3-(2'-methoxalylbiphenyl-4-yl)methyl-5,7-dimethyl-3H-imidazo[ [4.5-b]pyridine Following a procedure similar to that described in Example 1(a), but using 350 mg of 2-ethyl-5,7-dimethyl-3H-imidazo[4,5-b]pyridine, 828 mg of methyl (4'-bromomethylbiphenyl-4-yl)glyoxylate (prepared as described in Preparation 8) and 247 mg of potassium t-butoxide, 684 mg of the title compound were obtained as a syrup.

Nuclear Magnetic Resonance Spectrum (CDCl$_3$, 270 MHz), δ ppm: 1.37 (3H, triplet, J=7.5 Hz); 2.57 (3H, singlet); 2.64 ( 3H, singlet ); 2.84 (2H, quartet, J=7.5 Hz); 3.24 (3H, singlet); 5.50 (2H, singlet); 6.90 (1H, singlet); 7.18 (2H, doublet, J-8 Hz); 7.24 (2H, doublet, J=8 Hz); 7.41 (1H, doublet, J=7 Hz); 7.50 (1H, triplet, J=7 Hz); 7.63 (1H, triplet, J=7 Hz); 7.80 ( 1H, doublet, J=7 Hz).

16(b) 2-Ethyl-5,7-dimethyl-3-(2'-oxalobiphenyl-4-yl)methyl- 3H-imidazo[4,5-b]pyridine 684 mg of 2-ethyl-3-(2'-methoxalylbiphenyl-4-yl)methyl-5,7-dimethyl-3H-imidazo[4,5-b]pyridine [prepared as described in step (a) above] were subjected to hydrolysis using 201 mg of lithium hydroxide monohydrate in the same manner as described in Example 1(b), to give 460 mg of the title compound as a powder, melting at 209°–210° C.

Nuclear Magnetic Resonance Spectrum (hexadeuterated dimethyl sulfoxide, 270 MHz), δ ppm: 1.28 (3H, triplet, J=7.5 Hz); 2.55 (6H, singlet); 2.83 (2H, quartet, J=7.5 Hz); 5.53 (2H, singlet); 6.99 (1H, singlet); 7.19–7.26 (4H, multipier); 7.44 (1H, doublet, J=7 Hz); 7.54 (1H, triplet, J=7 Hz); 7.61–7.71 (2H, multiplet).

EXAMPLE 17

2-{N-[(2'-Oxalobiphenyl-4-yl)methyl]-N-propylamino}nicotinic acid (Compound No. 3-2)

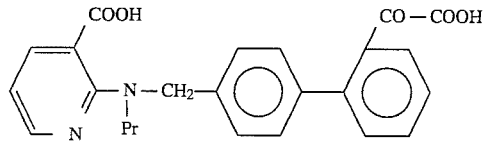

17(a) Ethyl 2-{N-[(2'-methoxalylbiphenyl-4-yl)methyl]-N-propylamino}nicotinate 4.65 ml of a 1M solution of lithium bis(trimethylsilyl)amide in tetrahydrofuran were added at −5° to 0° C. under an atmosphere of nitrogen gas to a mixed solution of 0.80 g of ethyl 2-(propylamino)nicotinate dissolved in 6 ml of tetrahydrofuran and 2 ml of hexamethylphosphoric triamide, and the resulting mixture was stirred at −5° to 0° C. for 10 minutes. A solution of 1.28 g of methyl (4'-bromomethybiphenyl-2-yl)glyoxylate (prepared as described in preparation 8) dissolved in 8 ml of tetrahydrofuran was then added to the resulting solution, and the mixture was stirred at 10° to 15° C. for 4 hours. At the end of this time, ethyl acetate was added to the reaction mixture, and the resulting ethyl acetate solution was washed with water and dried over anhydrous magnesium sulfate. The solvent was then removed by distillation under reduced pressure. The resulting residue was subjected to column chromatography through silica gel, using a 1:4 by volume mixture of ethyl acetate and hexane as the eluent, to give 0.70 g of the title compound as a gum.

Nuclear Magnetic Resonance Spectrum (CDCl$_3$, 270 MHz) δ ppm: 0.80 (3H, triplet, J=7.5 Hz); 1.39 (3H, triplet, J=7.5 Hz); 1.60 (2H, sextet, J=7.5 Hz); 3.24 (3H, singlet); 3.26 (2H, triplet, J=7.5 Hz); 4.35 (2H, quartet, J=7.5 Hz); 4.76 (2H, singlet); 6.70 (1H, doublet of doublets, J=5 & 7.5 Hz); 7.24 (2H, doublet, J=8 Hz); 7.38 (2H, doublet, J=8 Hz); 7.44 (1H, doublet, J=7 Hz); 7.48 (1H, triplet, J=7 Hz); 7.63 (1H, triplet, J=7 Hz); 7.91 (1H, doublet of doublets, J=1.5 & 7.5 Hz); 8.23 (1H, doublet of doublets, J=1.5 & 5 Hz).

17(b) 2-{N-[(2'-Oxalobiphenyl-4-yl)methyl]-N-propylamino}nicotinic acid

A solution of 350 mg of lithium hydroxide monohydrate dissolved in 10 ml of water was added to a solution of 0.70 g of ethyl 2-{N-[(2'-methoxalylbiphenyl-4-yl)methyl]-N-propylamino}nicotinate [prepared as described in step (a) above] dissolved in 5 ml of dioxane, and the resulting mixture was stirred at 70° C. for 4 hours. At the end of this time, the dioxane was removed by distillation under reduced pressure, and 8.33 ml of 1N aqueous hydrochloric acid were added to the residual aqueous solution. The crystals thus precipitated were collected by filtration, to give 0.57 g of the title compound, melting at 179°–180° C.

Nuclear Magnetic Resonance Spectrum (hexadeuterated dimethyl sulfoxide, 270 MHz), δ ppm: 0.76 (3H, triplet, J=7.5 Hz); 1.53 (2H, sextet, J=7.5 Hz); 3.26 (2H, triplet, J=7.5 Hz); 4.73 (2H, singlet); 6.81 (1H, doublet of doublets, J=4.5 & 8 Hz); 7.21 (2H, doublet, J=8 Hz); 7.34 (2H, doublet, J=8 Hz); 7.48 (1H, doublet, J=7 Hz); 7.54 (1H, triplet, J=7 Hz); 7.66–7.72 (2H, multipier); 7.90 (1H, doublet of doublets, J=2 & 8 Hz); 8.25 (1H, doublet of doublets, J=2 & 4.5 Hz).

EXAMPLE 18

2-{N-(2-Methoxyethyl)-N-[(2'-oxalobiphenyl-4-yl)methyl]amino}nicotinic acid (Compound No. 3-19)

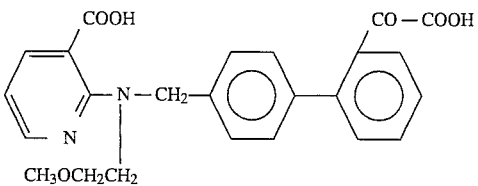

18(a) Ethyl 2-{N-[(2'-methoxalylbiphenyl-4-yl)methyl]-N-(2-methoxyethyl)amino}nicotinate Following a procedure similar to that described in Example 17(a), but using 750 mg of ethyl 2-[(2-methoxyethyl)amino]nicotinate, 1.17 g of methyl (4'-bromomethylbiphenyl-4-yl)glyoxylate (prepared as described in preparation 8) and 4.00 ml of a 1M solution of lithium bis(trimethylsilyl)amide in tetrahydrofuran, 535 mg of the title compound were obtained as a syrup.

Nuclear Magnetic Resonance Spectrum (CDCl$_3$, 270 MHz), δ ppm: 1.38 (3H, triplet, J=7.5 Hz); 3.25 (3H, singlet); 3.27 (3H, singlet); 3.52–3.61 (4H, multipier); 4.33 (2H, quartet, J=7.5 Hz); 4.81 (2H, singlet); 6.73 (1H, doublet of doublets, J=4.5 & 8 Hz); 7.24 (2H, doublet, J=8 Hz); 7.38 (2H, doublet, J=8 Hz); 7.44 (1H, doublet, J=7 Hz); 7.48 (1H, triplet, J=7 Hz); 7.62 (1H, triplet, J=7 Hz); 7.81 (1H, doublet, J=7 Hz); 7.92 (1H, doublet of doublets, J=2 & 8 Hz); 8.24 (1H, doublet of doublets, J=2 & 4.5 Hz).

18(b) 2-{N-(2-Methoxyethyl)-N-[(2'-oxalobiphenyl-4yl)methyl]amino}nicotinic acid A solution of 535 mg of ethyl 2-{N-[(2'-methoxalylbiphenyl-4-yl)methyl]-N-(2-methoxyethyl)amino}nicotinate [prepared as described in step (a) above] dissolved in 4.5 ml of dioxane and a 1N aqueous solution of sodium hydroxide were mixed, and the resulting mixture was stirred at 50° C. for 19 hours. At the end of this time, the dioxane was removed by distillation under reduced pressure, and 4.5 ml of 1N aqueous hydrochloric acid was added to the residual aqueous solution. The crystals thus precipitated were collected by filtration, to give 306 mg of the title compound, melting at 173° C. (with decomposition).

Nuclear Magnetic Resonance Spectrum (hexadeuterated dimethyl sulfoxide, 270 MHz), δ ppm: 3.16 (3H, singlet); 3.40–3.52 (4H, multipier); 4.78 (2H, singlet); 6.83 (1H, doublet of doublets, J=4.5 & 7.5 Hz); 7.21 (2H, doublet, J=8 Hz); 7.34 (2H, doublet, J=8 Hz); 7.48 (1H, doublet, J=7 Hz); 7.54 (1H, triplet, J=7 Hz); 7.66–7.72 (2H, multipier); 7.90 (1H, doublet of doublets, J=1.5 & 7.5 Hz); 8.24 (1H, doublet of doublets, J=1.5 & 4.5 Hz).

EXAMPLE 19

19(a) Ethyl 4-(1-hydroxy-1-methylethyl)-1-{[2'-(tetrazol-5-ylcarbonyl)biphenyl-4-yl]methyl}-2-propylimidazole-5-carboxylate (Compound No. 1-50)

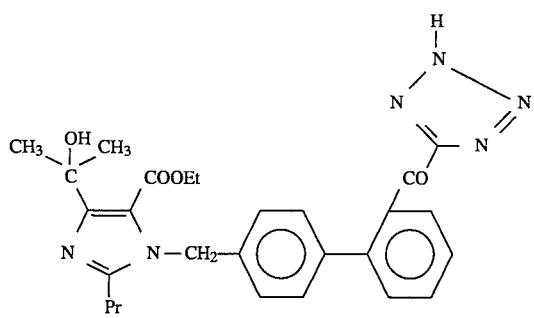

19(a) Ethyl 4-(1-hydroxy-1-methylethyl)-1-{[2'-(2-trityltetrazol-5-ylcarbonyl)biphenyl-4-yl]methyl}-2-propylimidazole-5-carboxylate Following a procedure similar to that described in Example 1(a), but using 190 mg of ethyl 4-(1-hydroxy-1-methylethyl)-2-propylimidazole-5-carboxylate, 93 mg of potassium t-butoxide and 470 mg of 4'-bromomethyl-2-(2-trityltetrazol-5-ylcarbonyl)biphenyl (prepared as described in Preparation 13), 218 mg of the title compound were obtained as an amorphous powder.

Nuclear Magnetic Resonance Spectrum (CDCl$_3$, 270 MHz), δ ppm: 0.89 (3H, triplet, J=7.5 Hz); 1.12 (3H, triplet, J=7.0 Hz); 1.63 (6H, singlet); 1.60–1.70 (2H, multipier); 2.52 (2H, triplet, J=8.0 Hz); 4.14 ( 2H, quartet, J=7.0 Hz); 5.35 (2H, singlet); 5.74 (1H, singlet); 6.76 (2H, doublet, J=8 .5 Hz); 6.92 (5H, doublet, J=7.5 Hz); 7.07 (2H, doublet, J=8.5 Hz); 7.25–7.38 (11H, multiplet); 7.45 (1H, triplet, J=7.0 Hz); 7.59 (1H, triplet, J=7.5 Hz); 7.70 (1H, doublet, J=8.5 Hz).

19(b) Ethyl 4-(hydroxy-1-methylethyl)-1-{[2'-(tetrazol-5-ylcarbonyl)biphenyl-4-yl]methyl}-2-propylimidazole-5-carboxylate 216 mg of ethyl 4-(1-hydroxy-1-methylethyl)-1-{[2'-(2-trityltetrazol-5-ylcarbonyl)biphenyl-4-yl]methyl}-2-propylimidazole-5-carboxylate [prepared as described in step (a) above] were subjected to detritylation in the same manner as described in Example 7(b), to give 151 mg of the title compound as an amorphous powder, Nuclear Magnetic Resonance Spectrum (CDCl$_3$, 270 MHz), δ ppm: 0.86 (3H, triplet, J=7.5 Hz); 1.20 (3H, triplet, J=7.5 Hz); 1.53–1.65 (2H, multipier); 1.65 (6H, singlet); 2.68 (2H, triplet, J=8.0 Hz); 4.26 (2H, quartet, J=7.5 Hz); 5.41 (2H, singlet); 6.80 (2H, doublet, J=8.0 Hz); 7.24 (2H, doublet, J=8.0 Hz); 7.41–7.49 (2H, multipier); 7.58 (1H, triplet, J=7.0 Hz); 7.77 (1H, doublet, J=6.5 Hz).

EXAMPLE 20

4-(1-Hydroxy-1-methylethyl)-1-{[2'-(tetrazol-5-ylcarbonyl)biphenyl-4-yl]methyl}-2-propylimidazole-5-carboxylic acid (Compound No. 1-42)

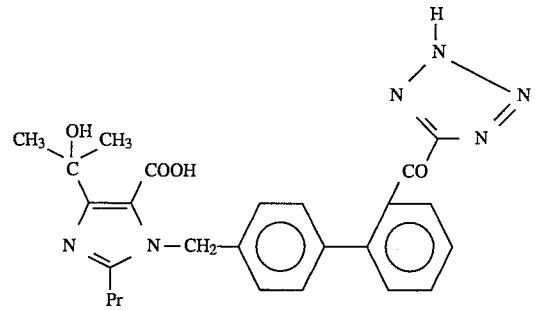

Following a procedure similar to that described in Example 1(b), but using 151 mg of ethyl 4-(hydroxy-1-methylethyl)-1-{[2'-(tetrazol-5-ylcarbonyl)biphenyl-4-yl]methyl}-2-propylimidazole-5-carboxylate and 36 mg of lithium hydroxide monohydrate, 97 mg of the title compound were obtained as a crystalline powder, melting at 166°–169° C. (with decomposition).

Nuclear Magnetic Resonance Spectrum (hexadeuterated dimethyl sulfoxide, 270 MHz), δ ppm: 0.87 (3H, triplet, J=7.5 Hz); 1.45–1.56 (2H, multipier); 1.56 (6H, singlet); 2.58 (2H, triplet, J=7.5 Hz); 5.61 (2H, singlet); 6.94 (2H, doublet, J=8 .5 Hz); 7.19 (2H, doublet, J=8 .5 Hz); 7.49–7.58 (2H, multipier); 7.67–7.75 (2H, multipier).

EXAMPLE 21

2-Ethyl-5,7-dimethyl-3-[2'-(tetrazol-5-ylcarbonyl)biphenyl-4-yl]methyl-3H-imidazo[4,5-b]pyridine (Compound No. 2-51)

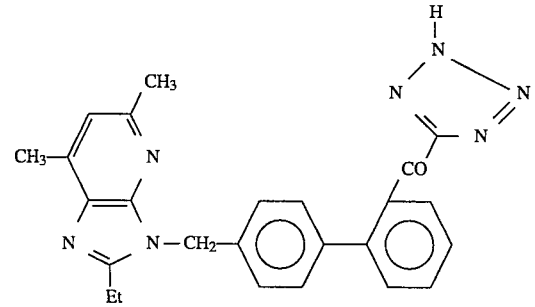

21(a) 2-Ethyl-5,7-dimethyl-3-[2'-(2-trityltetrazol-5-ylcarbonyl)biphenyl-4-yl]methyl-3H-imidazo[4,5-b]pyridine Following a procedure similar to that described in Example 1(a), but using 130 mg of 2-ethyl-5,7-dimethyl-3H-imidazo[4,5-b]pyridine, 522 mg of 4'-bromomethyl-2-(2-trityltetrazol-5-ylcarbonyl)biphenyl (prepared as described in Preparation 13) and 87 mg of potassium t-butoxide, 144 mg of the title compound were obtained as an amorphous powder.

Nuclear Magnetic Resonance Spectrum (CDCl$_3$, 270 MHz), δ ppm: 1.23 (3H, triplet, J=7.5 Hz); 2.56 (3H, singlet); 2.63 (3H, singlet); 2.66 (2H, quartet, J=7.5 Hz); 5.34 (2H, singlet); 6.87–6.9 5 (7H, multiplet); 6.96 (2H, doublet, J=8 Hz); 7.23–7.4 0 (10H, multipier); 7.37 (1H, doublet, J=7 Hz); 7.46 ( 1H, triplet, J=7 Hz); 7.58 (1H, triplet, J=7 Hz); 7.71 (1H, doublet, J=7 Hz).

21(b) 2-Ethyl-5,7-dimethyl-3-[2'-(tetrazol-5-ylcarbonyl)biphenyl-4-yl]methyl-3H-imidazo[4,5-b]pyridine 137 mg of 2-ethyl-5,7-dimethyl-3-[2'-(2-trityltetrazol-5-ylcarbonyl)biphenyl-4-yl]methyl-3H-imidazo[4,5-b]pyridine [prepared as described in step (a) above] were subjected to detritylation in the same manner as described in Example 7(b), to give 68 mg of the title compound as a powder, melting at 174°–177° C.

Nuclear Magnetic Resonance Spectrum (hexadeuterated dimethyl sulfoxide, 270 MHz), δ ppm: 1.20 (3H, triplet, J=7.5 Hz); 2.52 (6H, singlet); 2.73 (2H, quartet, J=7.5 Hz); 5.44 (2H, singlet); 7.03 (1H, singlet); 7.04 (2H, doublet, J=8 Hz); 7.17 (2H, doublet, J=8 Hz); 7.49–7.58 (2H, multipier); 7.67–7.75 (2H, multipier); 8.31 (1H, singlet).

EXAMPLE 22

2-Butyl-1-[(2'-oxalobiphenyl-4-yl)methyl]benzimidazole-5-carboxylic acid (Compound No. 2-53) and 2-Butyl-1-[(2'-oxalobiphenyl-4-yl)methyl]benzimidazole-6-carboxylic acid (Compound No. 2-54)

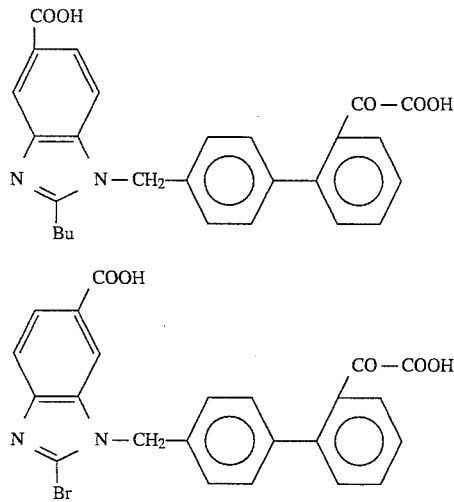

22(a) Methyl 2-butyl-1-[(2'-methoxalylbiphenyl-4-yl)methyl]benzimidazole-5- and 6-carboxylates Following a procedure similar to that described in Example 1(a), but using 404 mg of methyl 2-butylbenzimidazole-5-carboxylate, 637 mg of methyl 4'-bromomethylbiphenyl-2-glyoxylate (prepared as described in Preparation 8) and 200 mg of potassium t-butoxide, 620 mg of the title compound were obtained as a gum. The product was found from the nuclear magnetic resonance spectrum to be a 1:1 mixture of the compounds having the methoxycarbonyl groups at the 5- and 6-positions of the benzimidazole rings.

Nuclear Magnetic Resonance Spectrum (CDCl$_3$, 270 MHz), δ ppm: 0.96 (3H, triplet, J=7.5 Hz); 1.47 (2H, sextet, J=7.5 Hz); 1.88 (2H, quintet, J=7.5 Hz); 2.89 (2H, triplet, J=7.5 Hz); 3.24 & 3.76 (total 3H, each singlet); 3.90 & 3.93 (total 3H, each singlet); 5.41 & 5.45 (total 2H, each singlet); 7.08–7.49 (10.5H, multipier); 8.48 (0.5H, singlet).

22(b) 2-Butyl-1-[(2'-oxalobiphenyl-4-yl)methyl]benzimidazole-5- and 6-carboxylic acids 620 mg of the mixture of methyl 2-butyl-1-[(2'-methoxalylbiphenyl-4-yl)methyl]benzimidazole-5- and 6-carboxylates [prepared as described in step (a) above] were subjected to hydrolysis using 269 mg of lithium hydroxide hydrate in the same manner as described in Example 1(b), to give 511 mg of the title compound as a powder, melting at 160°–180° C. The product was found from the nuclear magnetic resonance spectrum to be a 1:1 mixture of the compounds having the carboxy groups at the 5- and 6-positions of the benzimidazole rings.

Nuclear Magnetic Resonance Spectrum (hexadeuterated dimethyl sulfoxide, 270 MHz), δ ppm: 0.89 (3H, triplet, J=7.5 Hz); 1.39 (2H, sextet, J=7.5 Hz); 1.75 (2H, quintet, J=7.5 Hz); 2.91 (2H, triplet, J=7.5 Hz); 5.62 & 5.67 (total 2H, each singlet); 7.14–7.87 (10H, multipier); 8.16–8.20 (1H, multipier).

EXAMPLE 23

2-Ethyl-1-[(2'-oxalobiphenyl-4-yl)methyl]benzimidazole-7-carboxylic acid (Compound No. 2-26)

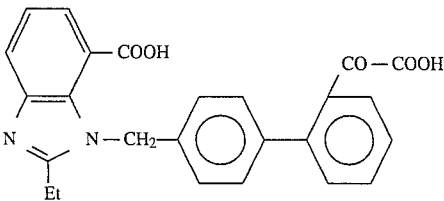

23(a) Ethyl 2-{N-t-butoxycarbonyl-N-[(2'-methoxalylbiphenyl-4-yl)methyl]amino 56 -3-nitrobenzoate Following a procedure similar to that described in Example 1(a), but using 1.01 g of ethyl 2-t-butoxycarbonylamino- 3-nitrobenzoate, 1.2 g of methyl (4'-bromomethylbiphenyl-2-yl)glyoxylate (prepared as described in Preparation 8) and 155 mg of a 55% w/w dispersion of sodium hydride in mineral oil, 1.43 g of the title compound were obtained as a gum.

Nuclear Magnetic Resonance Spectrum (CDCl$_3$, 270 MHz), δ ppm: 1.35 (9H, singlet); 1.36 (3H, triplet, J=7 Hz); 3.31 (3H, singlet); 4.26 (2H, quartet, J=7 Hz); 4.45 (1H, quartet, J=14.5 Hz); 4.93 (1H, doublet, J=14.5 Hz); 7.15–7.27 (4H, multipier); 7.41–7.51 (3H, multipier); 7.63 (1H, triplet, J=7 Hz); 7.79 (1H, doublet, J=7 Hz); 7.88 (1H, doublet, J=8 Hz); 8.07 (1H, doublet, J=7 Hz).

23(b) Ethyl 2-ethyl-1-[(2'-methoxalylbiphenyl-4-yl)methyl] benzimidazole-7-carboxylate 1.06 g of ethyl 2-{N-t-butoxycarbonyl-N-[(2'-methoxalylbiphenyl-4-yl)methyl]amino}-3-nitrobenzoate [prepared as described in step (a) above] were dissolved in 10 ml of a 4N solution of hydrogen chloride in ethyl acetate, and the resulting solution was left to stand at room temperature for 4 hours. At the end of this time, the reaction mixture was concentrated by evaporation under reduced pressure, and the resulting gum-like residue was dissolved in 20 ml of ethanol and 10 ml of triethyl orthopropionate. 150 mg of 5% w/w platinum-on-carbon was then added to the resulting solution. The mixture was stirred at room temperature for 2 hours in an atmosphere of hydrogen at atmospheric pressure, after which it was left to stand overnight at room temperature. At the end of this time, the catalyst was removed by filtration, and the reaction mixture was then concentrated by evaporation under reduced pressure. The resulting residue was dissolved in a mixture of ethyl acetate and a saturated aqueous solution of sodium hydrogencarbonate, and the mixture was shaken. The ethyl acetate layer was separated and dried over anhydrous magnesium sulfate. The solvent was then removed by evaporation under reduced pressure, and the resulting residue was subjected to column chromatography, using a 1:1 by volume mixture of ethyl acetate and hexane as the eluent, to give 343 mg of the title compound as crystals, melting at 118°–119° C.

Nuclear Magnetic Resonance Spectrum (CDCl$_3$, 270 MHz), δ ppm: 1.28 (3H, triplet, J=7.5 Hz); 1.48 (3H, triplet, J=7 Hz); 2.91 (2H, quartet, J=7.5 Hz); 3.17 (3H, singlet); 4.26 (2H, quartet, J=7 Hz); 5.84 (2H, singlet); 6.93 (2H, doublet, J=8.5 Hz); 7.18 (2H, doublet, J=8.5 Hz); 7.22–7.98 (7H, multipier).

23(c) 2-Ethyl-1-[(2'-oxalobiphenyl-4-yl)methyl]benzimidazole-7-carboxylic acid 300 mg of ethyl 2-ethyl-1-[(2'-methoxalylbiphenyl-4-yl)methyl]benzimidazole-7-carboxylate [prepared as described in step (b) above] were subjected to hydrolysis using 134 mg of lithium hydroxide monohydrate in the same manner as described in Example 17(b), to give 264 mg of the title compound as a powder, melting at 278°–281° C.

Nuclear Magnetic Resonance Spectrum (hexadeuterated dimethyl sulfoxide, 270 MHz), δ ppm: 1.33 (3}{, triplet, J=7.5 Hz); 2.87 (2}{, quartet, J=7.5 Hz); 5.90 (2H, singlet); 6.92 (2H, doublet, J=8 Hz); 7.19 (2H, doublet, J=8 Hz); 7.27 (1H, triplet, J=7 Hz); 7.42 (1H, doublet, J=7 Hz); 7.53 (1H, triplet, J=7 Hz); 7.64–7.70 (3H, multipier); 7.86 (1H, doublet, J=8 Hz).

EXAMPLE 24

2-Ethoxy-1-[(2'-oxalobiphenyl-4-yl)methyl]benzimidazole-7-carboxylic acid (Compound No. 2-44)

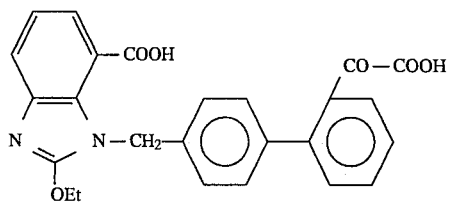

24(a) Ethyl 2-ethoxy-1-[(2'-methoxalylbiphenyl-4-yl)methyl]benzimidazole-7-carboxylate Following a procedure similar to that described in Example 23(b), but using 1.48 g of ethyl 2-{N-t-butoxycarbonyl-N-[(2'-methoxalylbiphenyl-4-yl)methyl]amino}-3-nitrobenzoate [prepared as described in Example 23(a)] and replacing the triethyl orthopropionate with 7 ml of tetraethyl orthocarbonate, 252 mg of the title compound were obtained as a gum.

Nuclear Magnetic Resonance Spectrum (CDCl$_3$, 270 MHz), δ ppm: 1.32 (3H, triplet, J=7.5 Hz); 1.50 (3H, triplet, J=7 Hz); 3.06 (3H, singlet); 4.31 (2H, quartet, J=7 Hz); 4.67 (2H, quartet, J=7.5 Hz); 5.71 (2H, singlet); 7.08 (2H, doublet, J=8 Hz); 7.18 (2H, doublet, J=8 Hz); 7.29–8.19 (7H, multipier).

24(b) 2-Ethoxy-1-[(2'-oxalobiphenyl-4-yl)methyl]benzimidazole-7-carboxylic acid 252 mg of ethyl 2-ethoxy-1-[(2'-methoxalylbiphenyl 4-yl)methyl]benzimidazole-7-carboxylate [prepared as described in step (a) above] were subjected to hydrolysis using 136 mg of lithium hydroxide monohydrate in the same manner as described in Example 17(b), to give 186 mg of the title compound as a powder, melting at 158°–161° C.

Nuclear Magnetic Resonance Spectrum (hexadeuterated dimethyl sulfoxide, 270 MHz), δ ppm: 1.42 (3H, triplet, J=7.5 Hz); 4.61 (2H, quartet, J=7.5 Hz); 5.67 (2H, singlet); 7.04 (2H, doublet, J=8 Hz); 7.10–7.97 (9H, multiplet).

EXAMPLE 25

Ethyl 2-(N-{[2'-(tetrazol-5-ylcarbonyl)biphenyl-4-yl]methyl}-N-propylamino)nicotinate (Compound No. 3-25)

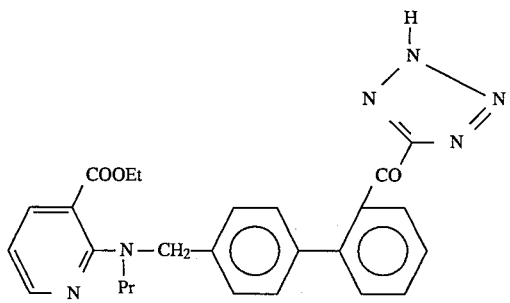

25(a) Ethyl 2-(N-{[2'-(2-trityltetrazol-5-ylcarbonyl)biphenyl-4-yl]methyl}-N-propylamino)nicotinate Following a procedure similar to that described in Example 18(a), but using 640 mg of ethyl 2-propylaminonicotinate, 1.8 g of 4'-bromomethyl-2-(2-trityltetrazol-5-ylcarbonyl)biphenyl (prepared as described in Preparation 13) and 3.69 ml of a 1M solution of lithium bis(trimethylsilyl)amide in tetrahydrofuran, 483 mg of the title compound were obtained as a foamy solid.

Nuclear Magnetic Resonance Spectrum (CDCl$_3$, 270 MHz), δ ppm: 0.73 (3H, triplet, J=7 Hz); 1.33 (3H, triplet, J=7 Hz); 1.48 (2H, sextet, J=7 Hz); 3.13 (2H, triplet, J=7 Hz); 4.30 (2H, quartet, J=7 Hz); 4.63 (2H, singlet); 6.68 (1H, doublet of doublets, J=4.5 & 7.5 Hz); 6.83–6.92 (5H, multipier); 6.96 (2H, doublet, J=8.5 Hz); 7.05 (2H, doublet, J=8.5 Hz); 7.23–7.44 (12H, multipier); 7.58 (1H, triplet, J=7.5 Hz); 7.71 (1H, doublet, J=6.5 Hz); 7.91 (1H, doublet of doublets, J=2 & 8 Hz); 8.20 (1H, doublet of doublets, J=2 & 4.5 Hz).

25(b) Ethyl 2-(N-{[2'-(tetrazol-5-ylcarbonyl)biphenyl-4-yl]methyl}-N-propylamino)nicotinate 483 mg of ethyl 2-(N-{[2'-(2-trityltetrazol-5-ylcarbonyl)biphenyl-4-yl]methyl}-N-propylamino)nicotinate [prepared as described in step (a) above] were subjected to detritylation in the same manner as described in Example 7(b), to give 320 mg of the title compound as a gum.

Nuclear Magnetic Resonance Spectrum (CDCl$_3$, 270 MHz), δ ppm: 0.79 (3H, triplet, J=7 Hz); 1.39 (3H, triplet, J=7 Hz); 1.54 (2H, sextet, J=7 Hz); 3.15 (2H, triplet, J=7 Hz); 4.37 (2H, quartet, J=7 Hz); 4.58 (2H, singlet); 6.80 (1H, doublet of doublets, J=5.5 & 7.5 Hz); 7.06 (2H, doublet, J=8.5 Hz); 7.16 (2H, doublet, J=8.5 Hz); 7.44–7.52 (2H, multipier); 7.61 (1H, triplet, J=7 Hz); 7.85 (1H, doublet, J=7 Hz); 8.03 (1H, doublet of doublets, J=2 & 7.5 Hz); 8.25 (1H, doublet of doublets, J=2 & 5 Hz).

EXAMPLE 26

2-(N-{[2'-(Tetrazol-5-ylcarbonyl)biphenyl-4-yl]methyl}-N-propylamino)nicotinic acid (Compound No. 3-20)

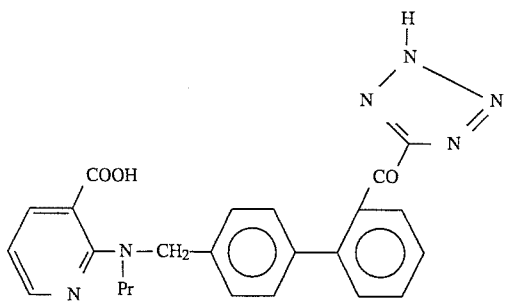

310 mg of ethyl 2-(N-{[2'-(tetrazol-5-ylcarbonyl)biphenyl-4-yl]methyl}-N-propylamino)nicotinate [prepared as described in Example 25(b)] were subjected to hydrolysis using 6 ml of a 1N aqueous solution of sodium hydroxide, to give 128 mg of the title compound as an amorphous powder, softening at 107°–109° C.

Nuclear Magnetic Resonance Spectrum (hexadeuterated dimethyl sulfoxide, 270 MHz), δ ppm: 0.74 (3H, triplet, J=7 Hz); 1.44 (2H, sextet, J=7 Hz); 3.12 (2H, triplet, J=7 Hz); 4.59 (2H, singlet); 7.81 (1H, doublet of doublets, J=4.5 & 8 Hz); 7.13 (2H, doublet, J=8.5 Hz); 7.19 (2H, doublet, J=8.5 Hz); 7.54–7.61 (2H, multipier); 7.74 (1H, triplet, J=7.5 Hz); 7.80 (1H, doublet, J=8 Hz); 7.89 (1H, doublet of doublets, J=2 & 8 Hz); 8.22 (1H, doublet of doublets, J=2 & 5 Hz).

PREPARATION 1

4'-Methylbiphenyl-2-carbaldehyde

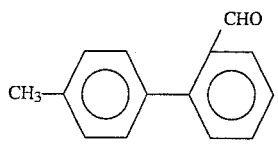

118 ml of a 1.5M solution of diisobutyl aluminum hydride dissolved in toluene were added dropwise at between –30° C. and –20° C. and under an atmosphere of nitrogen gas to a solution of 22.8 g of 4'-methylbiphenyl-2-carbonitrile dissolved in 200 ml of toluene, and then the mixture was stirred at room temperature for 2 hours. At the end of this time, the reaction mixture was ice-cooled, and then 200 ml of ethyl acetate and 60 ml of 6N aqueous hydrochloric acid were added to the mixture, in that order. The ethyl acetate layer was then separated, washed with a saturated aqueous solution of sodium chloride and dried over anhydrous magnesium sulfate. The solvent was then removed by distillation under reduced pressure, to give 23.1 g of the title compound as an oil.

Nuclear Magnetic Resonance Spectrum (CDCl$_3$, 60 MHz), δ ppm: 2.39 (3H, singlet); 7.2–7.7 (7H, multipier); 7.95–8.15 (1H, multipier); 10.07 (1H, singlet).

PREPARATION 2

α-Hydroxy-(4'-methylbiphenyl-2-yl)acetonitrile

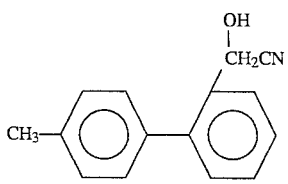

18 ml of trimethylsilyl cyanide were added dropwise to a solution of 23.1 g of 4'-methylbiphenyl-2-carbaldehyde (prepared as described in Preparation 1) dissolved in 250 ml of methylene chloride, after which 0.2 g of zinc iodide was added to the mixture. The resulting mixture was stirred at 30° C. for 3 hours and then at 50° C. for 2 hours, after which the solvent was removed by distillation under reduced pressure. The resulting residue was dissolved in ethyl acetate, washed with an aqueous solution of sodium hydrogencarbonate and then with a saturated aqueous solution of aqueous sodium chloride and dried over anhydrous sodium sulfate. The solvent was removed by distillation under reduced pressure, to give 35.0 g of the N-trimethylsilyl derivative of the title compound as an oil.

Nuclear Magnetic Resonance Spectrum (CDCl$_3$, 270 MHz), δ ppm: 0.09 (9H, singlet); 2.43 (3H, singlet); 5.47 (1H, singlet); 7.20 (2H, doublet, J=7.5 Hz); 7.26 (2H, doublet, J=7.5 Hz); 7.11–7.50 (3H, multipier); 7.79–7.82 (1H, multipier).

The whole of the O-trimethylsilyl derivative of the title compound thus obtained was dissolved in 300 ml of methanol, and then 1.5 g of p-toluenesulfonic acid monohydrate were added to the resulting solution, after which the mixture was stirred at room temperature for 30 minutes. At the end of this time, the reaction mixture was concentrated by evaporation under reduced pressure, and the residue was dissolved in ethyl acetate, washed with an aqueous solution of sodium hydrogencarbonate and with a saturated aqueous solution of sodium chloride, in that order, and dried over anhydrous sodium sulfate. The solvent was removed by distillation under reduced pressure, to give 26.1 g of the title compound as an oil.

Nuclear Magnetic Resonance Spectrum (CDCl$_3$, 270 MHz), δ ppm: 2.41 (3H, singlet); 2.89 (1H, doublet, J=6 Hz); 5.49 (1H, doublet, J=6 Hz); 7.25 (4H, singlet); 7.26–7.33 (1H, multipier); 7.42–7.49 (2H, multipier); 7.78–7.81 (1H, multipier).

PREPARATION 3

α-Hydroxy-(4'-methylbiphenyl-2-yl)acetonitrile

A solution of 6.0 g of potassium cyanide dissolved in 6 ml of water and a solution of 14 g of sodium hydrogensulfite dissolved in 35 ml of water were added dropwise at 0° to 5° C. to a solution of 8.00 g of 4'-methylbiphenyl-2-carbaldehyde (prepared as described in Preparation 1) dissolved in 10 ml of diethyl ether, and the resulting mixture was stirred at 5° to 10° C. for 3 hours and then at 20° C. for 30 minutes. At the end of this time, the product was extracted with ethyl acetate. The extract was washed with water and dried over anhydrous magnesium sulfate, after which the solvent was removed by evaporation under reduced pressure. The resulting residue was subjected to column chromatography through silica gel, using a 1:4 by volume mixture of ethyl acetate and hexane as the eluent, to give 7.7 g of the title compound as an oil.

The nuclear magnetic resonance spectrum of this compound was identical to that of the compound obtained as described in Preparation 2.

PREPARATION 4

Methyl α-hydroxy-(4'-methylbiphenyl-2-yl)acetate

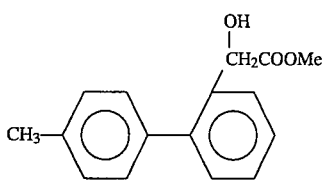

26.1 g of α-hydroxy-(4'-methylbiphenyl-2-yl)acetonitrile (prepared as described in Preparation 2) were added to a mixture of 150 ml of acetic acid and 150 ml of concentrated aqueous hydrochloric acid, with stirring, and the mixture was stirred on an oil bath at 120° C. for 16 hours. At the end of this time, the reaction mixture was concentrated by evaporation under reduced pressure. As much as possible of the residual acetic acid was removed by azeotropic distillation with toluene, and then the product was extracted into a solution of 12 g of sodium hydroxide in 200 ml of water. The resulting aqueous solution was washed with diethyl ether, and then concentrated aqueous hydrochloric acid was added to the aqueous alkaline solution until it became acidic. The N-hydroxy-(4'-methylbiphenyl-2-yl)acetic acid which then precipitated was extracted with ethyl acetate and dried over anhydrous magnesium sulfate. The solvent was then removed by evaporation under reduced pressure. The resulting residue was dissolved in 300 ml of methanol, and 13 ml of concentrated aqueous sulfuric acid was added to this solution, with ice-cooling. The solution was then left to stand at room temperature for 16 hours. At the end of this time, the reaction mixture was concentrated by evaporation under reduced pressure, and the residue was dissolved in ethyl acetate and water. The organic solvent layer was separated, washed with an aqueous solution of sodium hydrogencarbonate and with water, in that order and dried over anhydrous sodium sulfate. The solvent was then removed by evaporation under reduced pressure. The residue was subjected to column chromatography through silica gel, using a 1:4 by volume mixture of ethyl acetate and hexane as the eluent, to give 19.5 g of the title compound as crystals, melting at 74°–76° C.

Nuclear Magnetic Resonance Spectrum (CDCl$_3$, 270 MHz), δ ppm: 2.40 (3H, singlet); 3.38 (1H, doublet, J=4 Hz); 3.69 (3H, singlet); 5.26 (1H, doublet, J=4 Hz); 7.23 (2H, doublet, J=7 Hz); 7.31–7.37 (6H, multipier).

PREPARATION 5

Methyl (4'-methylbiphenyl-2-yl)glyoxylate

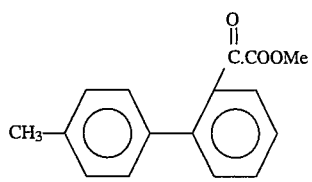

40 g of manganese dioxide were added to a solution of 10.6 g of methyl N-hydroxy-(4'-methylbiphenyl-2-yl)acetate (prepared as described in Preparation 4) dissolved in 200 ml of methylene chloride. The resulting mixture was stirred at room temperature for 16 hours, after which the insolubles were removed by filtration, and the filtrate was concentrated by evaporation under reduced pressure, to give 9.16 g of the title compound as crystals, melting at 81°–84° C.

Nuclear Magnetic Resonance Spectrum (CDCl$_3$, 270 MHz), δ ppm: 2.46 (3H, singlet); 3.39 (3H, singlet); 7.24–7.32 (4H, multipier); 7.50–7.58 (2H, multipier); 7.70 (1H, triplet, J=8 Hz); 7.89 (1H, doublet, J=8 Hz).

PREPARATION 6

(4'-Methylbiphenyl-2-yl)glyoxylic acid

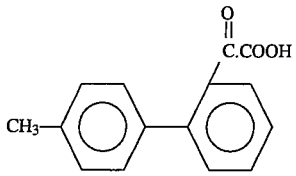

A solution of 1.73 g of sodium hydroxide dissolved in 90 ml of water was added to a solution of 9.16 g of methyl (4'-methylbiphenyl-2-yl)glyoxylate (prepared as described in Preparation 5) dissolved in 90 ml of methanol, and the resulting mixture was stirred at room temperature for 2 hours. At the end of this time, the methanol was removed by evaporation under reduced pressure, and 14.4 ml of 3N aqueous hydrochloric acid was added to the residual aqueous solution to adjust the pH of the mixture to a value of 2. The title compound which was thus precipitated was extracted with ethyl acetate, and the extract was dried over anhydrous magnesium sulfate. The solvent was then removed by evaporation under reduced pressure, to give 8.75 g of the title compound as crystals, melting at 111°–112° C.

Nuclear Magnetic Resonance Spectrum (CDCl$_3$, 270 MHz), δ ppm: 2.36 (3H, singlet); 7.13–7.22 (4H, multipier); 7.46–7.52 (2H, multipier); 7.65 (1H, triplet, J=7 Hz); 7.80 (1H, doublet, J=7 Hz).

PREPARATION 7 t-Butyl (4'-methylbiphenyl-2-yl)glyoxylate

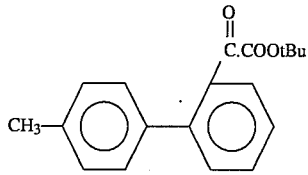

2 drops of dimethylformamide were added to a solution of 6.35 g of (4'-methylbiphenyl-2-yl)glyoxylic acid (prepared as described in Preparation 6) dissolved in 40 ml of methylene chloride, after which 15 ml of oxalyl chloride were added dropwise at room temperature. The resulting mixture was stirred at room temperature for 1 hour and then at 35° C. for 3 hours, after which it was concentrated by evaporation under reduced pressure. The residue was mixed with benzene, and then the mixture was concentrated by evaporation under reduced pressure. This procedure was repeated once more, and then the crystalline residue was dissolved in 30 ml of tetrahydrofuran. A solution of 4.00 g of potassium t-butoxide dissolved in 60 ml of tetrahydrofuran was then added dropwise at −40° to −30° C. to the resulting solution, and the mixture was stirred at room temperature for 2 hours. At the end of this time, water and a 2:1 by volume mixture of diethyl ether and hexane were added to the reaction mixture, and the organic solvent layer was separated. This extract was washed with water and dried over anhydrous magnesium sulfate, and then the solvent was removed by distillation under reduced pressure. The residue was subjected to column chromatography through silica gel, using a 1:9 by volume mixture of ethyl acetate and hexane as the eluent, to give 5.06 g of the title compound as an oil. The product thus obtained crystallized when left to stand at room temperature, giving crystals of the title compound, melting at 50°–51° C.

Nuclear Magnetic Resonance Spectrum (CDCl$_3$, 270 MHz), δ ppm: 1.16 (9H, singlet); 2.38 (3H, singlet); 7.20–7.26 (4H, multipier); 7.39–7.45 (2H, multipier); 7.47–7.61 (1H, multipier); 7.73–7.68 (1H, multipier).

PREPARATION 8

Methyl (4'-bromomethylbiphenyl-2-yl)glyoxylate

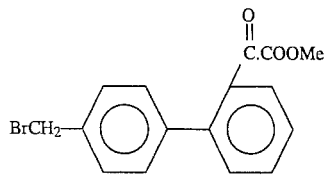

A suspension of 3.66 g of methyl (4'-methylbiphenyl-2-yl)glyoxylate (prepared as described in Preparation 2.56 g of N-bromosuccinimide and 0.1 g of benzoyl peroxide in 100 ml of carbon tetrachloride was stirred under reflux for 3 hours under irradiation from a 200 Watt tungsten lamp. At the end of this time, the reaction mixture was washed with an aqueous solution of sodium hydrogencarbonate and with a saturated aqueous solution of sodium chloride, in that order and dried over anhydrous magnesium sulfate. The solvent was then removed by evaporation under reduced pressure, and the crystalline residue was washed with diisopropyl ether, to give 3.68 g of the title compound, melting at 93°–96° C.

Nuclear Magnetic Resonance Spectrum (CDCl$_3$, 270 MHz), δ ppm: 3.36 (3H, singlet); 4.53 (2H, singlet); 7.29 (2H, doublet, J=7 Hz); 7.44–7.55 (4H, multipier); 7.62–7.68 (1H, multipier); 7.84 (1H, doublet, J=6.5 Hz).

PREPARATION 9 t-Butyl (4'-bromomethylbiphenyl-2-yl)glyoxylate

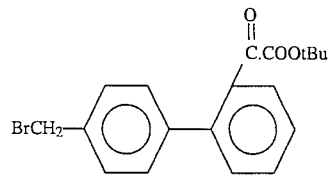

A suspension of 1.78 g of t-butyl (4'-methylbiphenyl-2-yl)glyoxylate (prepared as described in preparation 7), 1.12 g of N-bromosuccinimide and 50 mg of benzoyl peroxide in 50 ml of carbon tetrachloride was treated in the same manner as described in Preparation 8, to give 2.25 g of the title compound as a syrup. The product thus obtained crystallized when left to stand at room temperature, giving crystals of the title compound, melting at 100°–102° C.

Nuclear Magnetic Resonance Spectrum (CDCl$_3$, 270 MHz), δ ppm: 1.18 (3H, singlet); 4.52 (2H, singlet); 7.27 (1H, doublet, J=7 Hz); 7.32 (1H, doublet, J=7 Hz); 7.41–7.52 (4H, multipier); 7.62 (1H, triplet, J=7 Hz); 7.73 (1H, doublet, J=7 Hz).

PREPARATION 10

4'-Methyl-2-{α-hydroxy (tetrazol-5-yl)]methyl}biphenyl

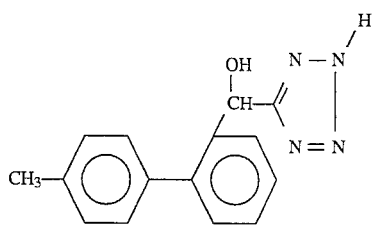

A solution of 4.73 g of α-hydroxy-(4'-methylbiphenyl-2-yl)acetonitrile (prepared as described in Preparation 2) and 20.8 g of tributyltin azide dissolved in 60 ml of toluene was stirred at 100° C. for 20 hours. At the end of this time, a solution of 4.05 g of sodium hydroxide in 200 ml of water was added to the reaction mixture, and the resulting mixture was stirred at room temperature for 1 hour. It was then washed with hexane three times. 8.5 ml of concentrated aqueous hydrochloric acid were added to the aqueous alkaline solution to make the mixture acidic. The compound which precipitated was extracted with ethyl acetate. The extract was dried over anhydrous sodium sulfate, and the solvent was removed by evaporation under reduced pressure, to give 3.57 g of the title compound as an amorphous solid. The compound thus obtained was used in the next reaction step (Preparation 11) without further purification.

PREPARATION 11

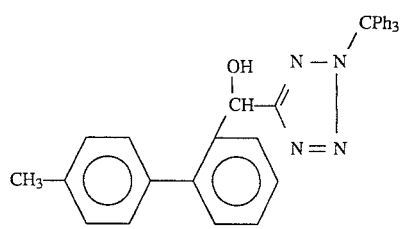

4'-Methyl-2-[α-hydroxy-(2-trityltetrazol-5-yl)methyl]biphenyl

A solution of 5.62 g of 4'-methyl-2-{α-hydroxy(tetrazol-5-yl)]methyl}biphenyl (prepared as described in preparation 10) and 3.92 g of trityl chloride dissolved in 100 ml of pyridine was stirred at 100° C. for 4.5 hours. At the end of this time, the reaction mixture was concentrated by evaporation under reduced pressure, and the resulting residue was dissolved in ethyl acetate. This solution was washed with water, with a 0.5% w/v aqueous solution of potassium carbonate and with a saturated aqueous solution of sodium chloride, in that order, after which it was dried over anhydrous sodium sulfate. The solvent was then removed by evaporation under reduced pressure. The resulting residue was subjected to column chromatography through silica gel, using a 2:1 by volume mixture of hexane and ethyl acetate as the eluent, to give 2.68 g of the title compound as an amorphous solid.

Nuclear Magnetic Resonance Spectrum (CDCl$_3$, 270 MHz), δ ppm: 2.37 (3H, singlet); 6.20 (1H, singlet); 7.05–7.38 (22H, multiplet); 7.55–7.59 (1H, multiplet).

PREPARATION 12

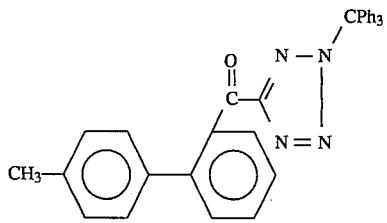

4'-Methyl-2-(2-trityltetrazol-5-ylcarbonyl)biphenyl 8 g of manganese dioxide were added to a solution of 2.48 g of 4'-methyl-2-[α-hydroxy-(2-trityltetrazol-5-yl)methyl] biphenyl (prepared as described in Preparation 11) dissolved in 50 ml of methylene chloride, and the resulting mixture was stirred at room temperature for 16 hours. At the end of this time, the insolubles were removed by filtration, and the filtrate was concentrated by evaporation under reduced pressure. The resulting residue was subjected to column chromatography through silica gel, using a 3:1 by volume mixture of hexane and ethyl acetate as the eluent, to give 1.20 g of the title compound as crystals, melting at 145°–147° C. (with decomposition).

Nuclear Magnetic Resonance Spectrum (CDCl$_3$, 270 MHz), δ ppm: 2.25 (3H, singlet); 6.82–6.92 (9H, multiple,); 7.24–7.40 (11H, multiple,); 7.46 (1H, triplet, J=7.5 Hz); 7.59 (1H, triplet, J=7.5 Hz); 7.74 (1H, doublet, J=8.5 Hz).

PREPARATION 13

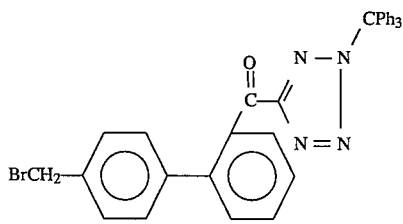

4'-Bromomethyl-2-(2-trityltetrazol-5-ylcarbonyl)biphenyl 400 mg of 4'-methyl-2-(2-trityltetrazol-5-ylcarbonyl)biphenyl (prepared as described in Preparation 12), 150 mg of N-bromosuccinimide and 20 mg of benzoyl peroxide were treated in the same manner as described in Preparation 8, to give 465 mg of the title compound as a crystalline powder, melting at 161°–163° C. (with decomposition).

Nuclear Magnetic Resonance Spectrum (CDCl$_3$, 270 MHz), δ ppm: 4.34 (2H, singlet); 6.84–6.87 (5H, multipier); 6.98 (2H, doublet, J=8.0 Hz); 7.10 (2H, doublet, J=8.0 Hz); 7.24–7.39 (11H, multipier); 7.48 (1H, triplet, J=7.5 Hz); 7.61 (1H, triplet, J=7.5 Hz); 7.74 (1H, doublet, J=6.0 Hz).

We claim:

1. A compound of formula (I):

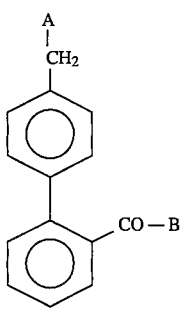

wherein:

A represents a group (IIa), (IIb) or (IIc);

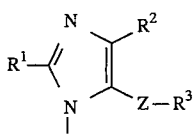

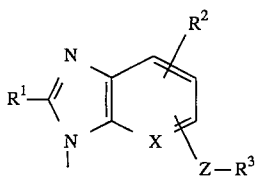

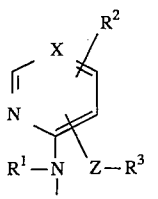

$R^1$ represents an alkyl group having from 1 to 6 carbon atoms, an alkenyl group having from 2 to 6 carbon atoms, a cycloalkyl group having from 3 to 8 ring carbon atoms or a group of formula $R^4$—Y—$R^5$—, where:

$R^4$ represents a hydrogen atom, an alkyl group having from 1 to 6 carbon atoms, or a cycloalkyl group having from 3 to 8 ring carbon atoms, $R^5$ represents a single bond or an alkylene group having from 1 to 4 carbon atoms, and Y represents an oxygen atom, a sulfur atom or an imino group (>NH);

$R^2$ represents a hydrogen atom, a halogen atom, an unsubstituted alkyl group having from 1 to 6 carbon atoms, an unsubstituted alkenyl group having from 2 to 6 carbon atoms, an unsubstituted cycloalkyl group having from 3 to 8 carbon atoms, a hydroxy group, an amino group, an alkylamino group having from 1 to 6 carbon atoms, a dialkylamino group in which each alkyl part has from 1 to 6 carbon atoms, a formyl group, an alkylcarbonyl group having from 2 to 7 carbon atoms, an alkoxy group having from 1 to 6 carbon atoms, an alkylthio group having from 1 to 6 carbon atoms, a cyano group, a nitro group, a substituted alkyl group which has from 1 to 6 carbon atoms and which is substituted by at least one substituent selected from the group consisting of substituents α defined below, a substituted alkenyl group which has from 2 to 6 carbon atoms and which is substituted by at least one substituent selected from the group consisting of substituents α defined below, or a substituted cycloalkyl group which has from 3 to 8 carbon atoms and which is substituted by at least one substituent selected from the group consisting of substituents α defined below;

$R^3$ represents a hydrogen atom, an alkyl group having from 1 to 6 carbon atoms, a carboxy group, a protected carboxy group, a carbamoyl group or a tetrazol-5-yl group;

X represents a group of formula —CH=, —N= or —C(COOR$^6$)=, where $R^6$ represents a hydrogen atom or a carboxy-protecting group;

Z represents a single bond, an alkylene group having from 1 to 4 carbon atoms or a vinylene group; and B represents a carboxy group, a protected carboxy group or a tetrazol-5-yl group;

said substituents α are selected from the group consisting of halogen atoms, hydroxy groups, amino groups, alkylamino groups having from 1 to 6 carbon atoms, dialkylamino groups in which each alkyl part has from 1 to 6 carbon atoms, formyl groups, alkylcarbonyl groups having from 2 to 7 carbon atoms, alkoxy groups having from 1 to 6 carbon atoms, alkylthio groups having from 1 to 6 carbon atoms, cyano groups and nitro groups;

and pharmaceutically acceptable salts and esters thereof.

2. The compound of claim 1, wherein A represents a group of formula (IIa), and $R^1$ represents an alkyl group having from 2 to 4 carbon atoms, an alkenyl group having from 3 to 5 carbon atoms, an alkoxyalkyl group in which the alkoxy part has from 1 to 3 carbon atoms and the alkyl part has 1 or 2 carbon atoms, an alkylthioalkyl group in which the alkylthio part has from 1 to 3 carbon atoms and the alkyl part has 1 or 2 carbon atoms, or an alkylthio group having from 1 to 3 carbon atoms.

3. The compound of claim 1, wherein A represents a group of formula (IIa), and $R^2$ represents a hydrogen atom, a halogen atom, an alkyl group having from 1 to 6 carbon atoms, an alkenyl group having from 3 to 6 carbon atoms or a substituted alkyl group which has from 1 to 6 carbon atoms and which is substituted by a halogen atom or a hydroxy group.

4. The compound of claim 1, wherein A represents a group of formula (IIa), and $R^3$ represents a carboxy group, a protected carboxy group, a carbamoyl group or a tetrazol-5-yl group.

5. The compound of claim 1, wherein A represents a group of formula (IIa), and Z represents a single bond, a methylene group or a vinylene group.

6. The compound of claim 1, wherein A represents a group of formula (IIa), and:

$R^1$ represents an alkyl group having from 2 to 4 carbon atoms, an alkenyl group having from 3 to 5 carbon atoms, an alkoxyalkyl group in which the alkoxy part has from 1 to 3 carbon atoms and the alkyl part has 1 or 2 carbon atoms, an alkylthioalkyl group in which the alkylthio part has from 1 to 3 carbon atoms and the alkyl part has 1 or 2 carbon atoms, or an alkylthio group having from 1 to 3 carbon atoms;

$R^2$ represents a hydrogen atom, a halogen atom, an alkyl group having from 1 to 6 carbon atoms, an alkenyl group having from 3 to 6 carbon atoms or a substituted alkyl group which has from 1 to 6 carbon atoms and which is substituted by a halogen atom or a hydroxyl group;

$R^3$ represents a carboxy group, a protected carboxy group, a carbamoyl group or a tetrazol-5-yl group; and Z represents a single bond, a methylene group or a vinylene group.

7. The compound of claim 1, wherein A represents a group of formula (IIb), and $R^1$ represents an alkyl group having from 2 to 4 carbon atoms, a cyclopropyl group, an alkoxyalkyl group in which the alkoxy part has from 1 to 3 carbon atoms and the alkyl part has 1 or 2 carbon atoms, an alkylthioalkyl group in which the alkylthio part has from 1 to 3 carbon atoms and the alkyl part has 1 or 2 carbon atoms, an alkoxy group having from 1 to 3 carbon atoms or an alkylthio group having from 1 to 3 carbon atoms.

8. The compound of claim 1, wherein A represents a group of formula (IIb), and $R^2$ represents a hydrogen atom, a halogen atom or an alkyl group having from 1 to 4 carbon atoms.

9. The compound of claim 1, wherein A represents a group of formula (IIb), and $R^3$ represents a hydrogen atom, an alkyl group having from 1 to 4 carbon atoms, a carboxy group, a protected carboxy group or a tetrazol-5-yl group.

10. The compound of claim 1, wherein A represents a group of formula (IIb), and Z represents a single bond, a methylene group or a vinylene group.

11. The compound of claim 1, wherein A represents a group of formula (IIb), and:

$R^1$ represents an alkyl group having from 2 to 4 carbon atoms, a cyclopropyl group, an alkoxyalkyl group in which the alkoxy part has from 1 to 3 carbon atoms and the alkyl part has 1 or 2 carbon atoms, an alkylthioalkyl group in which the alkylthio part has from 1 to 3 carbon atoms and the alkyl part has 1 or 2 carbon atoms, an alkoxy group having from 1 to 3 carbon atoms or an alkylthio group having from 1 to 3 carbon atoms;

$R^2$ represents a hydrogen atom, a halogen atom or an alkyl group having from 1 to 4 carbon atoms;

$R^3$ represents a hydrogen atom, an alkyl group having from 1 to 4 carbon atoms, a carboxy group, a protected carboxy group or a tetrazol-5-yl group;

X represents a group of formula —CH=, a group of formula —N= or a group of formula —C(COOR$^6$)=, wherein $R^6$ represents a hydrogen atom or a carboxy-protecting group; and Z represents a single bond, a methylene group or a vinylene group.

12. The compound of claim 1, wherein A represents a group of formula (IIc), and $R^1$ represents an alkyl group having from 2 to 4 carbon atoms, an alkoxyethyl group in which the alkoxy part has from 1 to 3 carbon atoms or an alkylthioethyl group in which the alkylthio part has from 1 to 3 carbon atoms.

13. The compound of claim 1, wherein A represents a group of formula (IIc), and $R^2$ represents a hydrogen atom, a halogen atom or an alkyl group having from 1 to 4 carbon atoms.

14. The compound of claim 1, wherein A represents a group of formula (IIc), and $R^3$ represents a hydrogen atom, an alkyl group having from 1 to 4 carbon atoms, a carboxy group, a protected carboxy group or a tetrazol-5-yl group.

15. The compound of claim 1, wherein A represents a group of formula (IIc), and X represents a group of formula —CH= or a group of formula —N=.

16. The compound of claim 1, wherein A represents a group of formula (IIc), and Z represents a single bond, a methylene group or a vinylene group.

17. The compound of claim 1, wherein A represents a group of formula (IIc), and:

R$^1$ represents an alkyl group having from 2 to 4 carbon atoms, an alkoxyethyl group in which the alkoxy part has from 1 to 3 carbon atoms or an alkylthioethyl group in which the alkylthio part has from 1 to 3 carbon atoms;

R$^2$ represents a hydrogen atom, a halogen atom or an alkyl group having from 1 to 4 carbon atoms;

R$^3$ represents a hydrogen atom, an alkyl group having from 1 to 4 carbon atoms, a carboxy group, a protected carboxy group or a tetrazol-5-yl group;

X represents a group of formula —CH= or a group of formula —N=; and

Z represents a single bond, a methylene group or a vinylene group.

18. The compound of claim 1, wherein R$^3$ or B represents a protected carboxy group or R$^6$ represents a carboxy-protecting group, and the protecting group is: an alkanoyloxyalkyl group in which the alkanoyl part has from 2 to 5 carbon atoms and the alkyl part has 1 or 2 carbon atoms; an alkoxycarbonyloxyalkyl group in which the alkoxy part has from 1 to 4 carbon atoms and the alkyl part has 1 or 2 carbon atoms; a cycloalkoxycarbonyloxyalkyl group in which the cycloalkane part has 5 or 6 carbon atoms and the alkyl part has 1 or 2 carbon atoms; or a (5-methyl-2-oxo-1,3-dioxolen-4-yl)methyl group.

19. The compound of claim 1, wherein B represents a carboxy group or a tetrazol-5-yl group.

20. The compound of claim 1, wherein A represents a group of formula (IIa), and R$^1$ represents an ethyl, propyl, butyl, 1-propenyl, 1-butenyl, 2-butenyl, methoxymethyl, ethoxymethyl, methylthiomethyl, ethylthiomethyl, methylthio or ethylthio group.

21. The compound of claim 1, wherein A represents a group of formula (IIa), and R$^2$ represents a chlorine atom, a bromine atom, or a methyl, ethyl, isopropyl, isopropenyl, trifluoromethyl, pentafluoroethyl, hydroxymethyl, 1-hydroxyethyl, 1-hydroxy-1-methylethyl, 1-hydroxypropyl, 1-hydroxy-1-methylpropyl, 1-hydroxy-2-methylpropyl or 1-hydroxy-2,2-dimethylpropyl group.

22. The compound of claim 1, wherein A represents a group of formula (IIa), and Z represents a single bond or a methylene group.

23. The compound of claim 1, wherein A represents a group of formula (IIa), and:

R$^1$ represents an ethyl, propyl, butyl, 1-propenyl, 1-butenyl, 2-butenyl, methoxymethyl, ethoxymethyl, methylthiomethyl, ethylthiomethyl, methylthio or ethylthio group;

R$^2$ represents a chlorine atom, a bromine atom, or a methyl, ethyl, isopropyl, isopropenyl, trifluoromethyl, pentafluoroethyl, hydroxymethyl, 1-hydroxyethyl, 1-hydroxy-1-methylethyl, 1-hydroxypropyl, 1-hydroxy-1-methylpropyl, 1-hydroxy-2-methylpropyl or 1-hydroxy-2,2-dimethylpropyl group;

R$^3$ represents a carboxy group, a protected carboxy group, a carbamoyl group or a tetrazol-5-yl group; and Z represents a single bond or a methylene group.

24. The compound of claim 1, wherein A represents a group of formula (IIb), and R$^1$ represents an ethyl, propyl, cyclopropyl, methoxy, ethoxy, propoxy, methylthio or ethylthio group.

25. The compound of claim 1, wherein A represents a group of formula (IIb), and R$^2$ represents a hydrogen atom, a fluorine atom, a chlorine atom, or a methyl, ethyl or isopropyl group.

26. The compound of claim 1, wherein A represents a group of formula (IIb), and R$^3$ represents a hydrogen atom, or a methyl, ethyl, carboxy, protected carboxy or tetrazol-5-yl group.

27. The compound of claim 1, wherein A represents a group of formula (IIb), and:

R$^1$ represents an ethyl, propyl, cyclopropyl, methoxy, ethoxy, propoxy, methylthio or ethylthio group;

R$^2$ represents a hydrogen atom, a fluorine atom, a chlorine atom, or a methyl, ethyl or isopropyl group;

R$^3$ represents a hydrogen atom, or a methyl, ethyl, carboxy, protected carboxy or tetrazol-5-yl group;

X represents a group of formula —CH=, a group of formula —N= or a group of formula —C(COOR$^6$)=, wherein R$^6$ represents a hydrogen atom or a carboxy-protecting group; and Z represents a single bond or a methylene group.

28. The compound of claim 1, wherein A represents a group of formula (IIc), and R$^1$ represents an ethyl, propyl, butyl, 2-methoxyethyl or 2-methylthioethyl group.

29. The compound of claim 1, wherein A represents a group of formula (IIc), and R$^2$ represents a hydrogen atom, a fluorine atom, a chlorine atom, or a methyl, ethyl or isopropyl group.

30. The compound of claim 1, wherein A represents a group of formula (IIc), and R$^3$ represents a hydrogen atom, or a methyl, ethyl, carboxy, protected carboxy or tetrazol-5-yl group.

31. The compound of claim 1, wherein A represents a group of formula (IIc), and:

R$^1$ represents an ethyl, propyl, butyl, 2-methoxyethyl or 2-methylthioethyl group;

R$^2$ represents a hydrogen atom, a fluorine atom, a chlorine atom, or a methyl, ethyl or isopropyl group;

R$^3$ represents a hydrogen atom, or a methyl, ethyl, carboxy, protected carboxy or tetrazol-5-yl group;

X represents a group of formula —CH= or a group of formula —N=; and

Z represents a single bond or a methylene group.

32. The compound of claim 1, wherein R$^3$ or B represents a protected carboxy group or R$^6$ represents a carboxy-protecting group, and the protecting group is: an acetoxymethyl, pivaloyloxymethyl, ethoxycarbonyloxymethyl, isopropoxycarbonyloxymethyl, 1-ethoxycarbonyloxyethyl, 1-isopropoxycarbonyloxyethyl, cyclohexyloxycarbonyloxymethyl, 1-cyclohexyloxycarbonyloxyethyl or (5-methyl-2-oxo-1,3-dioxolen-4-yl)methyl group.

33. The compound of claim 1, wherein A represents a group of formula (IIa), and R$^1$ represents an ethyl, propyl or butyl group.

34. The compound of claim 1, wherein A represents a group of formula (IIa), and R$^2$ represents a chlorine atom, or an isopropyl, isopropenyl, trifluoromethyl, pentafluoroethyl, 1-hydroxyethyl or 1-hydroxy-1-methylethyl group; and R$^3$ represents a carboxy group, a protected carboxy group or a tetrazol-5-yl group.

35. The compound of claim 1, wherein A represents a group of formula (IIa), and R$^2$ represents a 1-hydroxy-2-methylpropyl or 1-hydroxy-2,2-dimethylpropyl group, and R$^3$ represents a carbamoyl group.

36. The compound of claim 1, wherein A represents a group of formula (IIa), and Z represents a single bond.

37. The compound of claim 1, wherein A represents a group of formula (IIa), and:

R$^1$ represents an ethyl, propyl or butyl group;

$R^2$ represents a chlorine atom, or an isopropyl, isopropenyl, trifluoromethyl, pentafluoroethyl, 1-hydroxyethyl or 1-hydroxy-1-methylethyl group;

$R^3$ represents a carboxy group, a protected carboxy group or a tetrazol-5-yl group; and Z represents a single bond.

38. The compound of claim 1, wherein A represents a group of formula (IIa), and:

$R^1$ represents an ethyl, propyl or butyl group;

$R^2$ represents a 1-hydroxy-2-methylpropyl or 1-hydroxy-2,2-dimethylpropyl group;

$R^3$ represents a carbamoyl group; and

Z represents a single bond.

39. The compound of claim 1, wherein A represents a group of formula (IIb), and $R^1$ represents an ethyl, propyl, cyclopropyl, ethoxy, methylthio or ethylthio group.

40. The compound of claim 1, wherein A represents a group of formula (IIb), and $R^2$ represents a hydrogen atom or a methyl group.

41. The compound of claim 1, wherein A represents a group of formula (IIb), and $R^3$ represents a hydrogen atom, or a methyl, carboxy, protected carboxy or tetrazol-5-yl group.

42. The compound of claim 1, wherein A represents a group of formula (IIb), and Z represents a single bond.

43. The compound of claim 1, wherein A represents a group of formula (IIb), and:

$R^1$ represents an ethyl, propyl, cyclopropyl, ethoxy, methylthio or ethylthio group;

$R^2$ represents a hydrogen atom or a methyl group;

$R^3$ represents a hydrogen atom, or a methyl, carboxy, protected carboxy or tetrazol-5-yl group;

X represents a group of formula —CH=, a group of formula —N= or a group of formula —C(COOR$^6$)=, wherein $R^6$ represents a hydrogen atom or a carboxy-protecting group; and Z represents a single bond.

44. The compound of claim 1, wherein A represents a group of formula (IIc), and R represents an ethyl, propyl, butyl, 2-methoxyethyl or 2-methylthioethyl group.

45. The compound of claim 1, wherein A represents a group of formula (IIc), and $R^2$ represents a hydrogen atom or a methyl group.

46. The compound of claim 1, wherein A represents a group of formula (IIc), and $R^3$ represents a carboxy, protected carboxy or tetrazol-5-yl group.

47. The compound of claim 1, wherein A represents a group of formula (IIc), and X represents a group of formula —CH=.

48. The compound of claim 1, wherein A represents a group of formula (IIc), and:

$R^1$ represents an ethyl, propyl, butyl, 2-methoxyethyl or 2-methylthioethyl group;

$R^2$ represents a hydrogen atom or a methyl group;

$R^3$ represents a carboxy, protected carboxy or tetrazol-5-yl group;

X represents a group of formula —CH=; and

Z represents a single bond.

49. The compound of claim 1, wherein $R^3$ or B represents a protected carboxy group or $R^6$ represents a carboxy-protecting group, and the protecting group is an acetoxymethyl, pivaloyloxymethyl, ethoxycarbonyloxymethyl, isopropoxycarbonyloxymethyl, 1-ethoxycarbonyloxyethyl, 1-isopropoxycarbonyloxyethyl, cyclohexyloxycarbonyloxymethyl, 1-cyclohexyloxycarbonyloxyethyl or (5-methyl-2-oxo-1,3-dioxolen-4-yl)methyl group.

50. The compound of claim 1, selected from the group consisting of 4-(1-hydroxy-1-methylethyl)-1-[(2'-oxalobiphenyl-4-yl)methyl]-2-propylimidazole-5-carboxylic acid and pharmaceutically acceptable salts and esters thereof.

51. The compound of claim 1, selected from the group consisting of 4-(1-hydroxyethyl)-1-[(2'-oxalobiphenyl-4-yl)methyl]-2-propylimidazole-5-carboxylic acid and pharmaceutically acceptable salts and esters thereof.

52. The compound of claim 1, selected from the group consisting of 4-isopropyl-1-[(2'-oxalobiphenyl-4-yl)methyl]-2-propylimidazole-5-carboxylic acid and pharmaceutically acceptable salts and esters thereof.

53. The compound of claim 1, selected from the group consisting of 4-(1-hydroxy-2-methylpropyl)-1-[(2'-oxalobiphenyl-4-yl)-methyl]-2-propylimidazole-5-carboxamide and pharmaceutically acceptable salts and esters thereof.

54. The compound of claim 1, selected from the group consisting of 4-(1-hydroxy-2,2-dimethylpropyl)-1-[(2'-oxalobiphenyl-4-yl)methyl]-2-propylimidazole-5-carboxamide and pharmaceutically acceptable salts and esters thereof.

55. The compound of claim 1, selected from the group consisting of pivaloyloxymethyl 4-(1-hydroxy-1-methylethyl)-1-[(2'-oxalobiphenyl-4-yl)methyl]-2-propylimidazole- 5-carboxylate and pharmaceutically acceptable salts and esters thereof.

56. The compound of claim 1, selected from the group consisting of(5-methyl-2-oxo-1,3-dioxolen-4-yl)methyl 4-(1-hydroxy-1-methylethyl)-1-[(2'-oxalobiphenyl-4-yl)methyl]- 2-propylimidazole-5-carboxylate and pharmaceutically acceptable salts and esters thereof.

57. The compound of claim 1, selected from the group consisting of {4'-[4-(1-hydroxy-1-methylethyl)-2-propyl-5-(tetrazol-5-yl)imidazol-1-ylmethyl]biphenyl-2-yl}glyoxylic acid and pharmaceutically acceptable salts and esters thereof.

58. The compound of claim 1, selected from the group consisting of 2-ethyl-5,7-dimethyl-3-(2'-oxalobiphenyl-4-yl)methyl-3H-imidazo[4,5-b]pyridine and pharmaceutically acceptable salts and esters thereof.

59. The compound of claim 1, selected from the group consisting of 5,7-dimethyl-3-(2'-oxalobiphenyl-4-yl)methyl-2-propyl-3H-imidazo[4,5-b]pyridine and pharmaceutically acceptable salts and esters thereof.

60. The compound of claim 1, selected from the group consisting of 2-ethyl-1-[(2'-oxalobiphenyl-4-yl)methyl]benzimidazole-7-carboxylic acid and pharmaceutically acceptable salts and esters thereof.

61. The compound of claim 1, selected from the group consisting of pivaloyloxymethyl 2-ethyl-1-[(2'-oxalobiphenyl-4-yl)methyl]benzimidazole-7-carboxylate and pharmaceutically acceptable salts and esters thereof.

62. The compound of claim 1, selected from the group consisting of (5-methyl-2-oxo-1,3-dioxolen-4-yl)methyl 2-ethyl-1-[(2'-oxalobiphenyl-4-yl) methyl]benzimidazole 7-carboxylate and pharmaceutically acceptable salts and esters thereof.

63. The compound of claim 1, selected from the group consisting of 2-ethoxy-1-[(2'-oxalobiphenyl-4-yl)methyl] benzimidazole-7-carboxylic acid and pharmaceutically acceptable salts and esters thereof.

64. The compound of claim 1, selected from the group consisting of pivaloyloxymethyl 2-ethoxy-1-[(2'-oxalobiphenyl-4-yl)methyl]benzimidazole-7-carboxylate and pharmaceutically acceptable salts and esters thereof.

65. The compound of claim 1, selected from the group consisting of (5-methyl-2-oxo-1,3-dioxolen-4-yl)methyl 2-ethoxy-1-[(2'-oxalobiphenyl-4-yl)methyl]benzimidazole-7-carboxylate and pharmaceutically acceptable salts and esters thereof.

66. The compound of claim 1, selected from the group consisting of 2-{N-[(2'-oxalobiphenyl-4-yl)methyl]-N-propylamino}nicotinic acid and pharmaceutically acceptable salts and esters thereof.

67. The compound of claim 1, selected from the group consisting of (N-propyl-N-{4'-[3-(tetrazol-5-yl)pyrid-2-yl]aminomethyl]biphenyl-2-yl)glyoxylic acid and pharmaceutically acceptable salts and esters thereof.

68. A pharmaceutical composition for the treatment or prophylaxis of hypertension or of a cardiovascular disease, which comprises an effective amount of an anti-hypertensive agent in admixture with a pharmaceutically acceptable carrier or diluent, wherein the anti-hypertensive agent is selected from the group consisting of compounds of formula (I) and pharmaceutically acceptable salts and esters thereof, as claimed in claim 1.

69. The composition of claim 68, wherein A represents a group of formula (IIa), and:
   $R^1$ represents an alkyl group having from 2 to 4 carbon atoms, an alkenyl group having from 3 to 5 carbon atoms, an alkoxyalkyl group in which the alkoxy part has from 1 to 3 carbon atoms and the alkyl part has 1 or 2 carbon atoms, an alkylthioalkyl group in which the alkylthio part has from 1 to 3 carbon atoms and the alkyl part has 1 or 2 carbon atoms, or an alkylthio group having from 1 to 3 carbon atoms;
   $R^2$ represents a hydrogen atom, a halogen atom, an alkyl group having from 1 to 6 carbon atoms, an alkenyl group having from 3 to 6 carbon atoms or a substituted alkyl group which has from 1 to 6 carbon atoms and which is substituted by a halogen atom or a hydroxyl group;
   $R^3$ represents a carboxy group, a protected carboxy group, a carbamoyl group or a tetrazol-5-yl group; and
   Z represents a single bond, a methylene group or a vinylene group.

70. The composition of claim 68, wherein A represents a group of formula (IIb), and:
   $R^1$ represents an alkyl group having from 2 to 4 carbon atoms, a cyclopropyl group, an alkoxyalkyl group in which the alkoxy part has from 1 to 3 carbon atoms and the alkyl part has 1 or 2 carbon atoms, an alkylthioalkyl group in which the alkylthio part has from 1 to 3 carbon atoms and the alkyl part has 1 or 2 carbon atoms, an alkoxy group having from 1 to 3 carbon atoms or an alkylthio group having from 1 to 3 carbon atoms;
   $R^2$ represents a hydrogen atom, a halogen atom or an alkyl group having from 1 to 4 carbon atoms;
   $R^3$ represents a hydrogen atom, an alkyl group having from 1 to 4 carbon atoms, a carboxy group, a protected carboxy group or a tetrazol-5-yl group;
   X represents a group of formula —CH=, a group of formula —N= or a group of formula —C(COOR$^6$)=, wherein $R^6$ represents a hydrogen atom or a carboxy-protecting group; and
   Z represents a single bond, a methylene group or a vinylene group.

71. The composition of claim 68, wherein A represents a group of formula (IIc), and:
   $R^1$ represents an alkyl group having from 2 to 4 carbon atoms, an alkoxyethyl group in which the alkoxy part has from 1 to 3 carbon atoms or an alkylthioethyl group in which the alkylthio part has from 1 to 3 carbon atoms;
   $R^2$ represents a hydrogen atom, a halogen atom or an alkyl group having from 1 to 4 carbon atoms;
   $R^3$ represents a hydrogen atom, an alkyl group having from 1 to 4 carbon atoms, a carboxy group, a protected carboxy group or a tetrazol-5-yl group;
   X represents a group of formula —CH= or a group of formula —N=; and
   Z represents a single bond, a methylene group or a vinylene group.

72. The composition of claim 68, wherein $R^3$ or B represents a protected carboxy group or $R^6$ represents a carboxy-protecting group, and the protecting group is: an alkanoyloxyalkyl group in which the alkanoyl part has from 2 to 5 carbon atoms and the alkyl part has 1 or 2 carbon atoms; an alkoxycarbonyloxyalkyl group in which the alkoxy part has from 1 to 4 carbon atoms and the alkyl part has 1 or 2 carbon atoms; a cycloalkoxycarbonyloxyalkyl group in which the cycloalkane part has 5 or 6 carbon atoms and the alkyl part has 1 or 2 carbon atoms; or a (5-methyl-2-oxo-1,3-dioxolen-4-yl)methyl group.

73. The composition of claim 68, wherein B represents a carboxy group or a tetrazol-5-yl group.

74. The composition of claim 68, wherein A represents a group of formula (IIa), and:
   $R^1$ represents an ethyl, propyl, butyl, 1-propenyl, 1-butenyl, 2-butenyl, methoxymethyl, ethoxymethyl, methylthiomethyl, ethylthiomethyl, methylthio or ethylthio group;
   $R^2$ represents a chlorine atom, a bromine atom, or a methyl, ethyl, isopropyl, isopropenyl, trifluoromethyl, pentafluoroethyl, hydroxymethyl, 1-hydroxyethyl, 1-hydroxy-1-methylethyl, 1-hydroxypropyl, 1-hydroxy-1-methylpropyl, 1-hydroxy-2-methylpropyl or 1-hydroxy-2,2-dimethylpropyl group;
   $R^3$ represents a carboxy group, a protected carboxy group, a carbamoyl group or a tetrazol-5-yl group; and
   Z represents a single bond or a methylene group.

75. The composition of claim 68, wherein A represents a group of formula (IIb), and:
   $R^1$ represents an ethyl, propyl, cyclopropyl, methoxy, ethoxy, propoxy, methylthio or ethylthio group;
   $R^2$ represents a hydrogen atom, a fluorine atom, a chlorine atom, or a methyl, ethyl or isopropyl group;
   $R^3$ represents a hydrogen atom, or a methyl, ethyl, carboxy, protected carboxy or tetrazol-5-yl group;
   X represents a group of formula —CH=, a group of formula —N= or a group of formula —C(COOR$^6$)=, wherein $R^6$ represents a hydrogen atom or a carboxy-protecting group; and
   Z represents a single bond or a methylene group.

76. The composition of claim 68, wherein A represents a group of formula (IIc), and:
   $R^1$ represents an ethyl, propyl, butyl, 2-methoxyethyl or 2-methylthioethyl group;
   $R^2$ represents a hydrogen atom, a fluorine atom, a chlorine atom, or a methyl, ethyl or isopropyl group;
   $R^3$ represents a hydrogen atom, or a methyl, ethyl, carboxy, protected carboxy or tetrazol-5-yl group;
   X represents a group of formula —CH= or a group of formula —N=; and
   Z represents a single bond or a methylene group.

77. The composition of claim 68, wherein $R^3$ or B represents a protected carboxy group or $R^6$ represents a carboxy-protecting group, and the protecting group is: an acetoxymethyl, pivaloyloxymethyl, ethoxycarbonyloxymethyl, isopropoxycarbonyloxymethyl, 1-ethoxycarbonyloxyethyl, 1-isopropoxycarbonyloxyethyl, cyclohexyloxycarbonyloxymethyl, 1-cyclohexyloxycarbonyloxyethyl or (5-methyl-2-oxo-1,3-dioxolen-4-yl)methyl group.

78. The composition of claim 68, wherein A represents a group of formula (IIa), and:

$R^1$ represents an ethyl, propyl or butyl group;

$R^2$ represents a chlorine atom, or an isopropyl, isopropenyl, trifluoromethyl, pentafluoroethyl, 1-hydroxyethyl or 1-hydroxy-1-methylethyl group;

$R^3$ represents a carboxy group, a protected carboxy group or a tetrazol-5-yl group; and Z represents a single bond.

79. The composition of claim 68, wherein A represents a group of formula (IIa), and:

$R^1$ represents an ethyl, propyl or butyl group;

$R^2$ represents a 1-hydroxy-2-methylpropyl or 1-hydroxy-2,2-dimethylpropyl group;

$R^3$ represents a carbamoyl group; and

Z represents a single bond.

80. The composition of claim 68, wherein A represents a group of formula (IIb), and:

$R^1$ represents an ethyl, propyl, cyclopropyl, ethoxy, methylthio or ethylthio group;

$R^2$ represents a hydrogen atom or a methyl group;

$R^3$ represents a hydrogen atom, or a methyl, carboxy, protected carboxy or tetrazol-5-yl group;

X represents a group of formula —CH=, a group of formula —N= or a group of formula —C(COOR$^6$)=, wherein $R^6$ represents a hydrogen atom or a carboxy-protecting group; and Z represents a single bond.

81. The composition of claim 68, wherein A represents a group of formula (IIc), and:

$R^1$ represents an ethyl, propyl, butyl, 2-methoxyethyl or 2-methylthioethyl group;

$R^2$ represents a hydrogen atom or a methyl group;

$R^3$ represents a carboxy, protected carboxy or tetrazol-5-yl group;

X represents a group of formula —CH=; and

Z represents a single bond.

82. The composition of claim 68, wherein $R^3$ or B represents a protected carboxy group or $R^6$ represents a carboxy-protecting group, and the protecting group is an acetoxymethyl, pivaloyloxymethyl, ethoxycarbonyloxymethyl, isopropoxycarbonyloxymethyl, 1-ethoxycarbonyloxyethyl, 1-isopropoxycarbonyloxyethyl, cyclohexyloxycarbonyloxymethyl, 1-cyclohexyloxycarbonyloxyethyl or (5-methyl-2-oxo-1,3-dioxolen-4-yl)methyl group.

83. The composition of claim 68, wherein the anti-hypertensive agent is selected from the group consisting of:
4-(1-hydroxy-1-methylethyl)-1-[(2'-oxalobiphenyl-4-yl)methyl]-2-propylimidazole-5-carboxylic acid;
4-(1-hydroxyethyl)-1-[(2'-oxalobiphenyl-4-yl)methyl]-2-propylimidazole-5-carboxylic acid;
4-isopropyl-1-[(2'-oxalobiphenyl-4-yl)methyl]-2-propylimidazole-5-carboxylic acid;
4-(1-hydroxy-2-methylpropyl)-1-[(2'-oxalobiphenyl-4-yl)methyl]-2-propylimidazole-5-carboxamide;
4-(1-hydroxy-2,2-dimethylpropyl)-1-[(2'-oxalobiphenyl-4-yl)methyl]-2-propylimidazole-5-carboxamide;
pivaloyloxymethyl 4-(1-hydroxy-1-methylethyl)-1-[(2'-oxalobiphenyl-4-yl)methyl]-2-propylimidazole-5-carboxylate;
(5-methyl-2-oxo-1,3-dioxolen-4-yl)methyl 4-(1-hydroxy-1-methylethyl)-1-[(2'-oxalobiphenyl-4-yl)methyl]-2-propylimidazole-5-carboxylate;
{4'-[4-(1-hydroxy-1-methylethyl)-2-propyl-5-(tetrazol-5-yl)imidazol-1-ylmethyl]biphenyl-2-yl}glyoxylic acid;
2-ethyl-5,7-dimethyl-3-(2'-oxalobiphenyl-4-yl)methyl-3H-imidazo[4,5-b]pyridine;
5,7-dimethyl-3-(2'-oxalobiphenyl-4-yl)methyl-2-propyl-3H-imidazo[4,5-b]pyridine;
2-ethyl-1-[(2'-oxalobiphenyl-4-yl)methyl]benzimidazole-7-carboxylic acid;
pivaloyloxymethyl 2-ethyl-1-[(2'-oxalobiphenyl-4-yl)methyl]benzimidazole-7-carboxylate;
(5-methyl-2-oxo-1,3-dioxolen-4-yl)methyl 2-ethyl-1-[(2'-oxalobiphenyl-4-yl)methyl]benzimidazole-7-carboxylate;
2-ethoxy-1-[(2'-oxalobiphenyl-4-yl)methyl]benzimidazole-7-carboxylic acid;
pivaloyloxymethyl 2-ethoxy-1-[(2'-oxalobiphenyl-4-yl)methyl]benzimidazole-7-carboxylate;
(5-methyl-2-oxo-1,3-dioxolen-4-yl)methyl 2-ethoxy-1-[(2'-oxalobiphenyl-4-yl)methyl]benzimidazole-7-carboxylate;
2-{N-[(2'-oxalobiphenyl-4-yl)methyl]-N-propylamino}nicotinic acid; and
(N-propyl-N-{4'-[3-(tetrazol-5-yl)pyrid-2-yl}aminomethyl]biphenyl-2-yl)glyoxylic acid;
and pharmaceutically acceptable salts and esters thereof.

84. A method for the treatment or prophylaxis of hypertension or of a cardiovascular disease in a mammal, e.g. a human being, which comprises administering an effective amount of an anti-hypertensive agent to said mammal, wherein the anti-hypertensive agent is selected from the group consisting of compounds of formula (I) and pharmaceutically acceptable salts and esters thereof, as claimed in claim 1.

85. The method of claim 84, wherein A represents a group of formula (IIa), and:

$R^1$ represents an alkyl group having from 2 to 4 carbon atoms, an alkenyl group having from 3 to 5 carbon atoms, an alkoxyalkyl group in which the alkoxy part has from 1 to 3 carbon atoms and the alkyl part has 1 or 2 carbon atoms, an alkylthioalkyl group in which the alkylthio part has from 1 to 3 carbon atoms and the alkyl part has 1 or 2 carbon atoms, or an alkylthio group having from 1 to 3 carbon atoms;

$R^2$ represents a hydrogen atom, a halogen atom, an alkyl group having from 1 to 6 carbon atoms, an alkenyl group having from 3 to 6 carbon atoms or a substituted alkyl group which has from 1 to 6 carbon atoms and which is substituted by a halogen atom or a hydroxyl group;

$R^3$ represents a carboxy group, a protected carboxy group, a carbamoyl group or a tetrazol-5-yl group; and Z represents a single bond, a methylene group or a vinylene group.

86. The method of claim 84, wherein A represents a group of formula (IIb), and:

$R^1$ represents an alkyl group having from 2 to 4 carbon atoms, a cyclopropyl group, an alkoxyalkyl group in which the alkoxy part has from 1 to 3 carbon atoms and the alkyl part has 1 or 2 carbon atoms, an alkylthioalkyl group in which the alkylthio part has from 1 to 3 carbon atoms and the alkyl part has 1 or 2 carbon atoms, an alkoxy group having from 1 to 3 carbon atoms or an alkylthio group having from 1 to 3 carbon atoms;

$R^2$ represents a hydrogen atom, a halogen atom or an alkyl group having from 1 to 4 carbon atoms;

$R^3$ represents a hydrogen atom, an alkyl group having from 1 to 4 carbon atoms, a carboxy group, a protected carboxy group or a tetrazol-5-yl group;

X represents a group of formula —CH=, a group of formula —N= or a group of formula —C(COOR$^6$)=, wherein $R^6$ represents a hydrogen atom or a carboxy-protecting group; and Z represents a single bond, a methylene group or a vinylene group.

87. The method of claim 84, wherein A represents a group of formula (IIc), and:

$R^1$ represents an alkyl group having from 2 to 4 carbon atoms, an alkoxyethyl group in which the alkoxy part has from 1 to 3 carbon atoms or an alkylthioethyl group in which the alkylthio part has from 1 to 3 carbon atoms;

$R^2$ represents a hydrogen atom, a halogen atom or an alkyl group having from 1 to 4 carbon atoms;

$R^3$ represents a hydrogen atom, an alkyl group having from 1 to 4 carbon atoms, a carboxy group, a protected carboxy group or a tetrazol-5-yl group;

X represents a group of formula —CH= or a group of formula —N=; and

Z represents a single bond, a methylene group or a vinylene group.

88. The method of claim 84, wherein $R^3$ or B represents a protected carboxy group or $R^6$ represents a carboxy-protecting group, and the protecting group is: an alkanoyloxyalkyl group in which the alkanoyl part has from 2 to 5 carbon atoms and the alkyl part has 1 or 2 carbon atoms; an alkoxycarbonyloxyalkyl group in which the alkoxy part has from 1 to 4 carbon atoms and the alkyl part has 1 or 2 carbon atoms; a cycloalkoxycarbonyloxyalkyl group in which the cycloalkane part has 5 or 6 carbon atoms and the alkyl part has 1 or 2 carbon atoms; or a (5-methyl-2-oxo-1,3-dioxolen-4-yl)methyl group.

89. The method of claim 84, wherein B represents a carboxy group or a tetrazol-5-yl group.

90. The method of claim 84, wherein A represents a group of formula (IIa), and:

$R^1$ represents an ethyl, propyl, butyl, 1-propenyl, 1-butenyl, 2-butenyl, methoxymethyl, ethoxymethyl, methylthiomethyl, ethylthiomethyl, methylthio or ethylthio group;

$R^2$ represents a chlorine atom, a bromine atom, or a methyl, ethyl, isopropyl, isopropenyl, trifluoromethyl, pentafluoroethyl, hydroxymethyl, 1-hydroxyethyl, 1-hydroxy-1-methylethyl, 1-hydroxypropyl, 1-hydroxy-1-methylpropyl, 1-hydroxy-2-methylpropyl or 1-hydroxy-2,2-dimethylpropyl group;

$R^3$ represents a carboxy group, a protected carboxy group, a carbamoyl group or a tetrazol-5-yl group; and Z represents a single bond or a methylene group.

91. The method of claim 84, wherein A represents a group of formula (IIb), and:

$R^1$ represents an ethyl, propyl, cyclopropyl, methoxy, ethoxy, propoxy, methylthio or ethylthio group;

$R^2$ represents a hydrogen atom, a fluorine atom, a chlorine atom, or a methyl, ethyl or isopropyl group;

$R^3$ represents a hydrogen atom, or a methyl, ethyl, carboxy, protected carboxy or tetrazol-5-yl group;

X represents a group of formula —CH=, a group of formula —N= or a group of formula —C(COOR$^6$)=, wherein $R^6$ represents a hydrogen atom or a carboxy-protecting group; and Z represents a single bond or a methylene group.

92. The method of claim 84, wherein A represents a group of formula (IIc), and:

$R^1$ represents an ethyl, propyl, butyl, 2-methoxyethyl or 2-methylthioethyl group;

$R^2$ represents a hydrogen atom, a fluorine atom, a chlorine atom, or a methyl, ethyl or isopropyl group;

$R^3$ represents a hydrogen atom, or a methyl, ethyl, carboxy, protected carboxy or tetrazol-5-yl group;

X represents a group of formula —CH= or a group of formula —N=; and

Z represents a single bond or a methylene group.

93. The method of claim 84, wherein $R^3$ or B represents a protected carboxy group or $R^6$ represents a carboxy-protecting group, and the protecting group is: an acetoxymethyl, pivaloyloxymethyl, ethoxycarbonyloxymethyl, isopropoxycarbonyloxymethyl, 1-ethoxycarbonyloxyethyl, 1-isopropoxycarbonyloxyethyl, cyclohexyloxycarbonyloxymethyl, 1-cyclohexyloxycarbonyloxyethyl or (5-methyl-2-oxo-1,3-dioxolen-4-yl)methyl group.

94. The method of claim 84, wherein A represents a group of formula (IIa), and:

$R^1$ represents an ethyl, propyl or butyl group;

$R^2$ represents a chlorine atom, or an isopropyl, isopropenyl, trifluoromethyl, pentafluoroethyl, 1-hydroxyethyl or 1-hydroxy-1-methylethyl group;

$R^3$ represents a carboxy group, a protected carboxy group or a tetrazol-5-yl group; and Z represents a single bond.

95. The method of claim 84, wherein A represents a group of formula (IIa), and:

$R^1$ represents an ethyl, propyl or butyl group;

$R^2$ represents a 1-hydroxy-2-methylpropyl or 1-hydroxy-2,2-dimethylpropyl group;

$R^3$ represents a carbamoyl group; and

Z represents a single bond.

96. The method of claim 84, wherein A represents a group of formula (IIb), and:

$R^1$ represents an ethyl, propyl, cyclopropyl, ethoxy, methylthio or ethylthio group;

$R^2$ represents a hydrogen atom or a methyl group;

$R^3$ represents a hydrogen atom, or a methyl, carboxy, protected carboxy or tetrazol-5-yl group;

X represents a group of formula —CH=, a group of formula —N= or a group of formula —C(COOR$^6$)=, wherein $R^6$ represents a hydrogen atom or a carboxy-protecting group; and Z represents a single bond.

97. The method of claim 84, wherein A represents a group of formula (IIc), and:

$R^1$ represents an ethyl, propyl, butyl, 2-methoxyethyl or 2-methylthioethyl group;

$R^2$ represents a hydrogen atom or a methyl group;

$R^3$ represents a carboxy, protected carboxy or tetrazol-5-yl group;

X represents a group of formula —CH=; and

Z represents a single bond.

98. The method of claim 84, wherein $R^3$ or B represents a protected carboxy group or $R^6$ represents a carboxy-protecting group, and the protecting group is an acetoxymethyl, pivaloyloxymethyl, ethoxycarbonyloxymethyl, isopropoxycarbonyloxymethyl, 1-ethoxycarbonyloxyethyl, 1-isopropoxycarbonyloxyethyl, cyclohexyloxycarbonyloxymethyl, 1-cyclohexyloxycarbonyloxyethyl or (5-methyl-2-oxo-1,3-dioxolen-4-yl)methyl group.

99. The method of claim 84, wherein the anti-hypertensive agent is selected from the group consisting of:

4-(1-hydroxy-1-methylethyl)-1-[(2'-oxalobiphenyl-4-yl)methyl]-2-propylimidazole-5-carboxylic acid;

4-(1-hydroxyethyl)-1-[(2'-oxalobiphenyl-4-yl)methyl]-2-propylimidazole-5-carboxylic acid;

4-isopropyl-1-[(2'-oxalobiphenyl-4-yl)methyl]-2-propylimidazole-5-carboxylic acid;

4-(1-hydroxy-2-methylpropyl)-1-[(2'-oxalobiphenyl-4-yl)methyl]- 2-propylimidazole-5-carboxamide;

4-(1-hydroxy-2,2-dimethylpropyl)-1-[(2'-oxalobiphenyl-4-yl)methyl]- 2-propylimidazole-5-carboxamide;

pivaloyloxymethyl 4-(1-hydroxy-1-methylethyl)-1-[(2'-oxalobiphenyl-4-yl)methyl]-2-propylimidazole-5-carboxylate;

(5-methyl-2-oxo-1,3-dioxolen-4-yl)methyl 4-(1-hydroxy-1-methylethyl)-1-[(2'-oxalobiphenyl-4-yl)methyl]-2-propylimidazole-5-carboxylate;

{4'-[4-(1-hydroxy-1-methylethyl)-2-propyl-5-(tetrazol-5-yl)imidazol-1-ylmethyl]biphenyl-2-yl}glyoxylic acid;

2-ethyl-5,7-dimethyl-3-(2'-oxalobiphenyl-4-yl)methyl-3H-imidazo[4,5-b]pyridine;

5,7-dimethyl-3-(2'-oxalobiphenyl-4-yl)methyl-2-propyl-3H-imidazo[4,5-b]pyridine;

2-ethyl-1-[(2'-oxalobiphenyl-4-yl)methyl]benzimidazole-7-carboxylic acid;

pivaloyloxymethyl 2-ethyl-1-[(2'-oxalobiphenyl-4-yl)methyl]benzimidazole-7-carboxylate;

(5-methyl-2-oxo-1,3-dioxolen-4-yl)methyl 2-ethyl-1-[(2'-oxalobiphenyl-4-yl)methyl]benzimidazole-7-carboxylate;

2-ethoxy-1-[(2'-oxalobiphenyl-4-yl)methyl]benzimidazole-7-carboxylic acid;

pivaloyloxymethyl 2-ethoxy-1-[(2'-oxalobiphenyl-4-yl)methyl]benzimidazole-7-carboxylate;

(5-methyl-2-oxo-1,3-dioxolen-4-yl)methyl 2-ethoxy-1-[(2'-oxalobiphenyl-4-yl)methyl]benzimidazole-7-carboxylate;

2-{N-[(2'-oxalobiphenyl-4-yl)methyl]-N-propylamino}nicotinic acid; and (N-propyl-N-{4'-[3-(tetrazol-5-yl)pyrid-2-yl}aminomethyl]biphenyl-2-yl)glyoxylic acid;

and pharmaceutically acceptable salts and esters thereof.

* * * * *

UNITED STATES PATENT AND TRADEMARK OFFICE
CERTIFICATE OF CORRECTION

PATENT NO. : 5,459,148
DATED : October 17, 1995
INVENTOR(S) : YANAGISAWA et al

It is certified that error appears in the above-indentified patent and that said Letters Patent is hereby corrected as shown below:

```
Title page, left column, [56] References Cited, U.S.
PATENT DOCUMENTS:  delete "4,335,040" and insert
--4,355,040--.
Column 3, line 35:  after "from" delete "i" and
insert --1--.
Column 12, line 23:  "3(i)." should begin a new
paragraph.
Column 15, lines 30-43, delete in entirety and replace
with the following:

--Bu      butyl
  tBu     t-butyl
  Et      ethyl
  cHx     cyclohexyl
  Me      methyl
  Mod     (5-methyl-2-oxo-1,3-dioxolen-4-yl)methyl
  Pom     pivaloyloxymethyl
  Pr      propyl
  cPr     cyclopropyl
  iPr     isopropyl
  Tz      tetrazol-5-yl--.
```

Signed and Sealed this

Eleventh Day of February, 1997

Attest:

BRUCE LEHMAN

Attesting Officer

Commissioner of Patents and Trademarks